(12) United States Patent
Kraus et al.

(10) Patent No.: US 9,926,340 B2
(45) Date of Patent: Mar. 27, 2018

(54) NAD ANALOGS AND METHODS OF USING SAID NAD ANALOGS IN DETERMINING RIBOSYLATION OF PROTEINS WITH PARP MUTANTS

(71) Applicants: The Board of Regents of the University of Texas System, Austin, TX (US); Biolog Life Science Institute Forschungslabor und Biochemica-Vertrieb GmbH, Bremen (DE); Cornell University, Ithaca, NY (US)

(72) Inventors: W. Lee Kraus, Coppell, TX (US); Bryan A. Gibson, Dallas, TX (US); Frank Schwede, Bremen (DE); Hening Lin, Ithaca, NY (US)

(73) Assignees: The Board of Regents of the University of Texas System, Austin, TX (US); Biolog Life Science Institute Forshungslabor und Biochemica-Vertrieb GmbH, Bremen (DE); Cornell University, Ithica, NY (US)

( * ) Notice: Subject to any disclaimer, the term of this patent is extended or adjusted under 35 U.S.C. 154(b) by 0 days.

(21) Appl. No.: 15/088,561

(22) Filed: Apr. 1, 2016

(65) Prior Publication Data
US 2016/0299141 A1    Oct. 13, 2016

Related U.S. Application Data

(60) Provisional application No. 62/144,711, filed on Apr. 8, 2015.

(51) Int. Cl.
| | | |
|---|---|---|
| G01N 33/573 | (2006.01) | |
| C07H 21/02 | (2006.01) | |
| C12Q 1/48 | (2006.01) | |

(52) U.S. Cl.
CPC ............... C07H 21/02 (2013.01); C12Q 1/48 (2013.01); G01N 2333/91142 (2013.01); G01N 2440/40 (2013.01); G01N 2458/00 (2013.01)

(58) Field of Classification Search
CPC  C07H 21/02; C12Q 1/48; G01N 2333/91142; G01N 2440/40; G01N 2458/00
(Continued)

(56) References Cited

U.S. PATENT DOCUMENTS 4,336,188 A * 6/1982 Zappelli ............... C07D 473/34
427/301

OTHER PUBLICATIONS

Lee; Journal of Solid Phase Biochemistry, 1977, 2, 213-224.*
(Continued)

*Primary Examiner* — Daniel R Carcanague
(74) *Attorney, Agent, or Firm* — Parker Highlander PLLC

(57) ABSTRACT

The present disclosure provides NAD analogs of the formula:

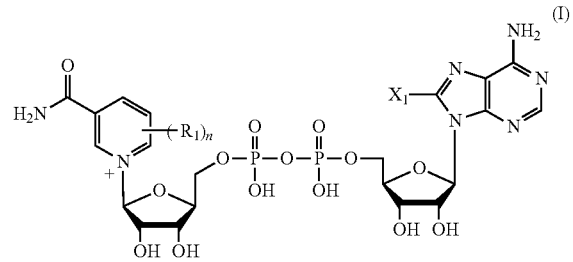

wherein $R_1$, n, and $X_1$ are defined herein, useful for the identification of PARP target proteins and the amino acid sequence wherein the ribose group is attached to the target protein. Also, provided herein are methods of (Continued)

identifying target protein and amino acid sequences. Additionally, the present disclosure provides methods of identifying DNA sequences associated with specific chromatin proteins.

22 Claims, 16 Drawing Sheets

(58) Field of Classification Search
USPC ...................................................... 546/284.4
See application file for complete search history.

(56) References Cited

OTHER PUBLICATIONS

Moreau; Org. Biomol. Chem., 2011, 9, 278-290.*
LePage; J. Biol. Chem. 1947, 168, 623-628.*
Huang; Archives of Biochemistry and Biophysics 1997, 348, 207-218.*
Du; Biochemistry, 2009, 48 (13), 2878-2890, with Supporting Information.*
Panza; Tetrahedron 2002, 58, 4091-4104.*
Zhang; Biochemistry 1993, 32, 2228-2233.*
Riva; Enzyme Microb. Technol., 1986, 9, 556-560.*
Amblard et al., "Cu(I)-catalyzed Huisgen azide-alkyne 1,3-dipolar cycloaddition reaction in nucleoside, nucleotide, and oligonucleotide chemistry," *Chem Rev*, 109:4207-4220, 2009.
Amé et al., "The PARP superfamily," *Bioessays*, 26:882-893, 2004.
Carter-O'Connell et al., "Engineering the substrate specificity of ADP-ribosyltransferases for identifying direct protein targets," *Journal of the American Chemical Society*, 136:5201-5204, 2014.
D'Amours et al., "Poly(ADP-ribosyl)ation reactions in the regulation of nuclear functions," *Biochem J*, 342(Part 2):249-268, 1999.
Gagné et al., "Proteome-wide identification of poly(ADP-ribose) binding proteins and poly(ADP-ribose)-associated protein complexes," *Nucleic Acids Res*, 36:6959-6976, 2008.

Gibson et al., "Chemical genetic discovery of PARP targets reveals a role for PARP-1 in transcription elongation," *Science*, 353(6294):45-50, 2016.
Gibson et al., "Clickable NAD+ analogs and analog-sensitive mutations of PARPs: a new approach for studying PARylation," Abstract, Cold Spring Harbor Laboratory Meeting, 2014.
Gibson, "Clickable NAD+ analogs and analog-sensitive PARPs: a new tool for studying PARylation," Cold Spring Harbor Laboratory Meeting—The PARP Family & Friends: Gene Regulation & Beyond, Apr. 11, 2014.
Hassa and Hottiger, "The diverse biological roles of mammalian PARPS, a small but powerful family of poly-ADP-ribose polymerases," *Front Biosci*, 13:3046-3082, 2008.
Kalesh et al., "The use of click chemistry in the emerging field of catalomics," *Org Biomol Chem*, 8:1749-1762, 2010.
Kim et al., "Poly(ADP-ribosyl)ation by PARP-1: 'PAR-laying' NAD+ into a nuclear signal," *Genes Dev*, 19:1951-1967, 2005.
Koch and Hauf, "Strategies for the identification of kinase substrates using analog-sensitive kinases," *Eur J Cell Biol*, 89:184-193, 2010.
Kraus et al., "The role of PARP-1 in chromatin-mediated gene regulation: control of cellular signaling and differentiation programs," Abstract, Cold Spring Harbor Laboratory Meeting—The PARP Family & Friends: Gene Regulation & Beyond, Apr. 9-12, 2014.
Kraus, "Transcriptional control by PARP-1: chromatin modulation, enhancer-binding, coregulation, and insulation," *Curr Opin Cell Biol*, 20:294-302, 2008.
Krishnakumar and Kraus, "The PARP side of the nucleus: molecular actions, physiological outcomes, and clinical targets," *Mol Cell*, 39:8-24, 2010.
Liang et al., "Kdm2b promotes induced pluripotent stem cell generation by facilitating gene activation early in reprogramming," *Nature Cell Biology*, 14:457-466, 2012.
Shokat and Velleca, "Novel chemical genetic approaches to the discovery of signal transduction inhibitors," *Drug Discov Today*, 7:872-879, 2002.

* cited by examiner wtPARP or asPARP 5 min ↓ + sssDNA 5 min ↓ + HeLa S3 N.E.

15 min ↓ + 8-Bu(3-yne)T-NAD⁺

Click to Azide-Fluor

FIG. 3

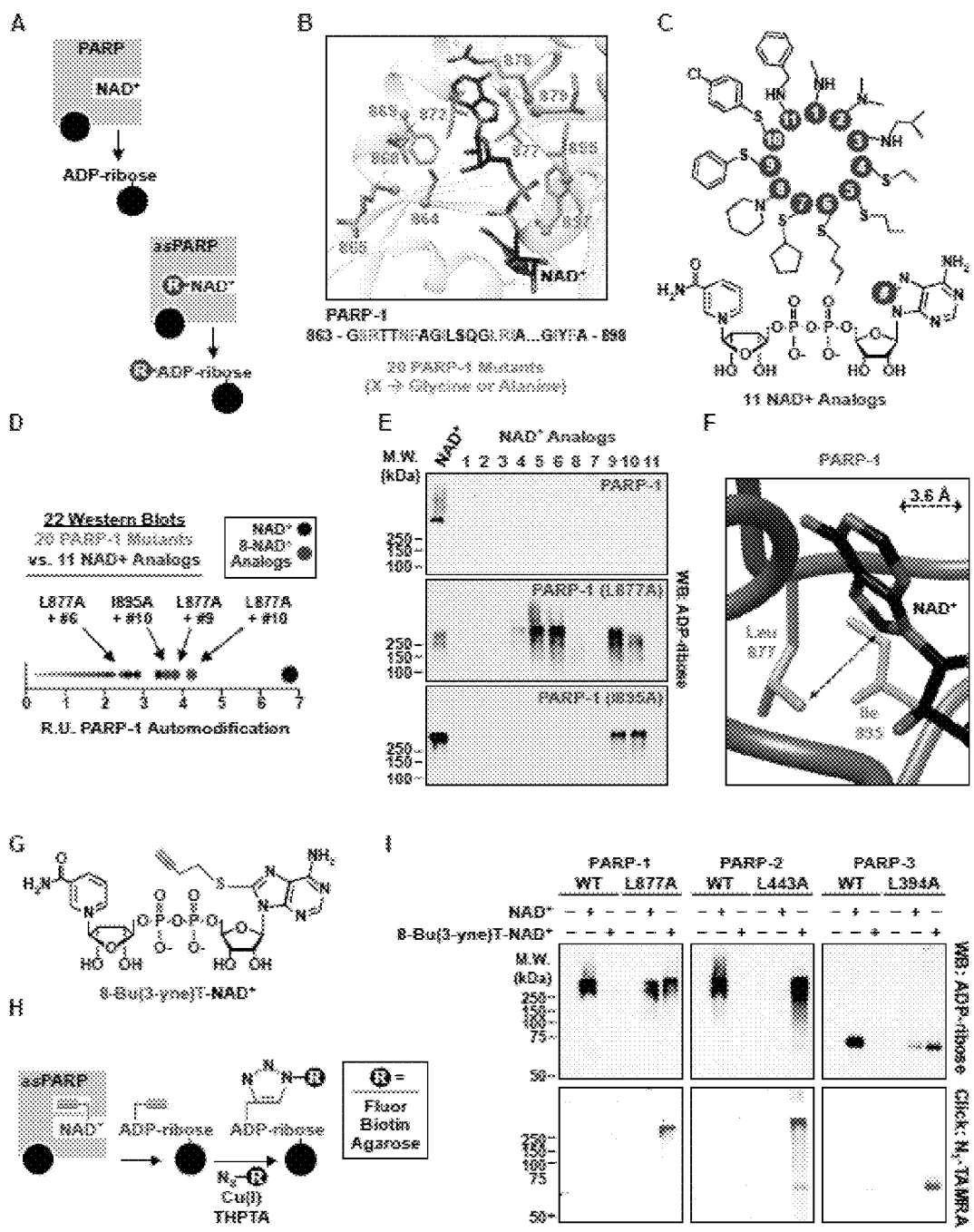
FIGS. 5A-I

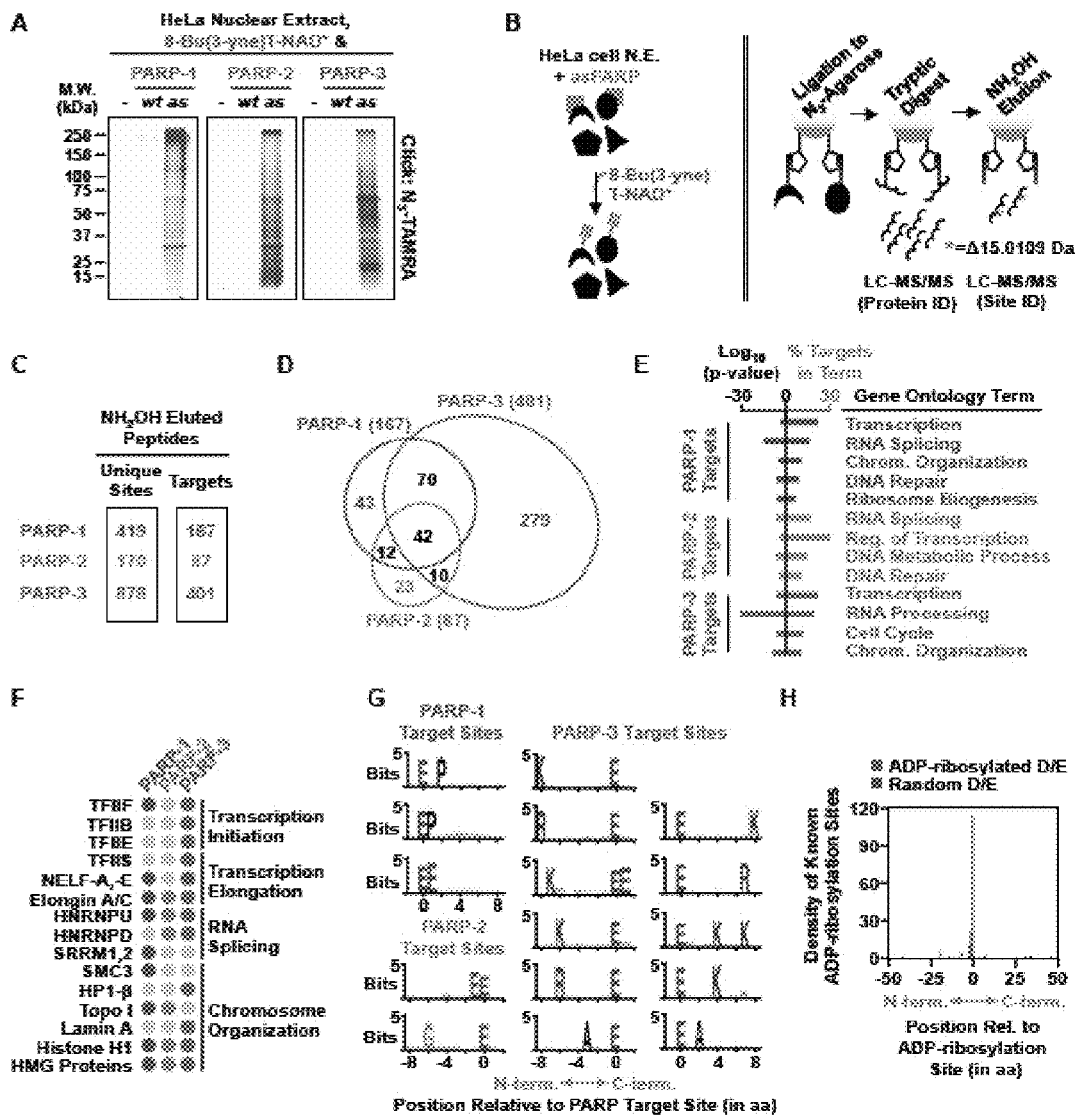
FIGS. 6A-H

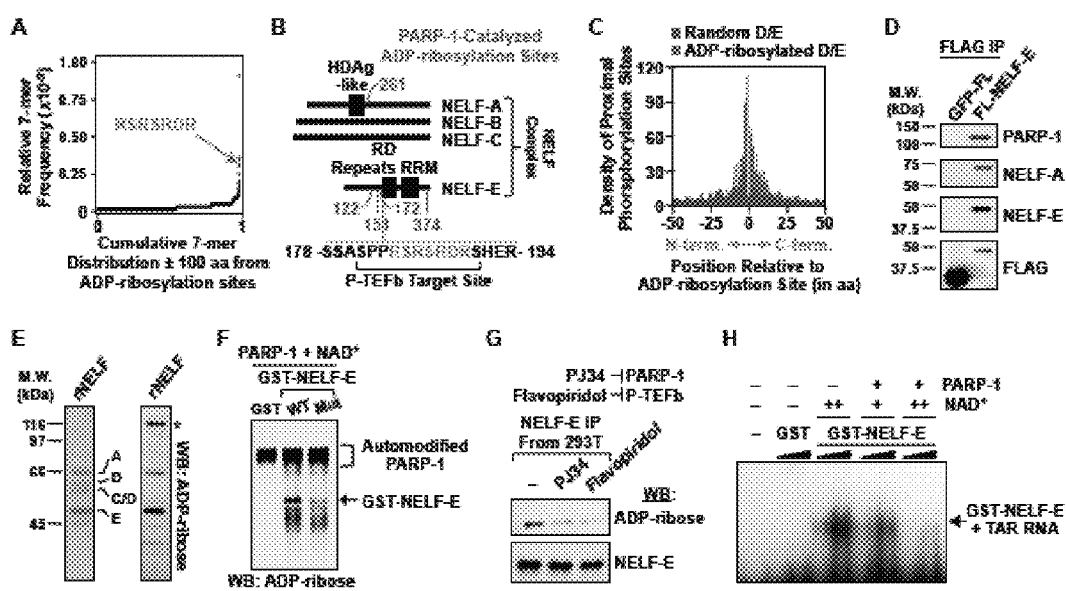
FIGS. 7A-H

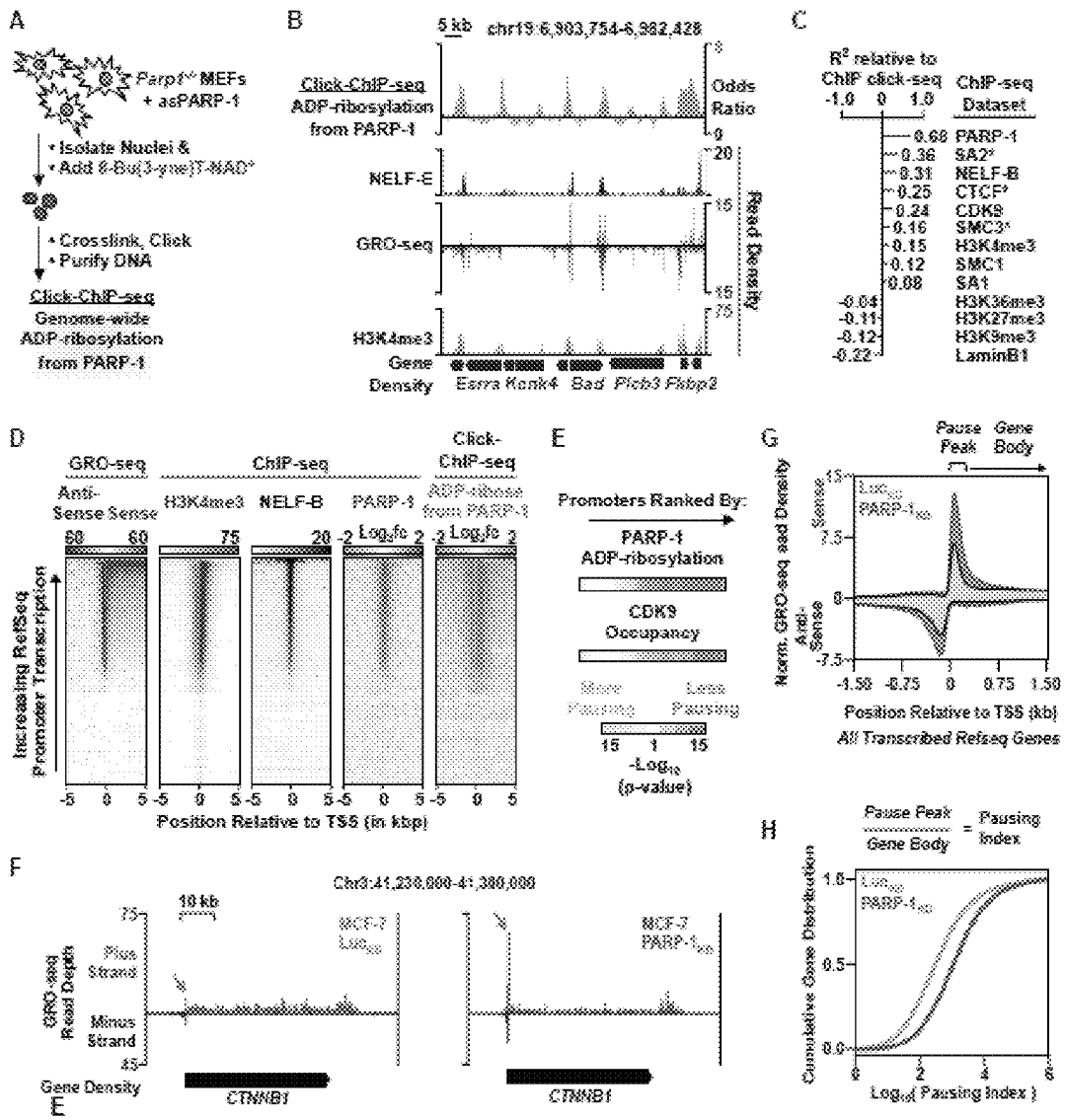
FIGS. 8A-H

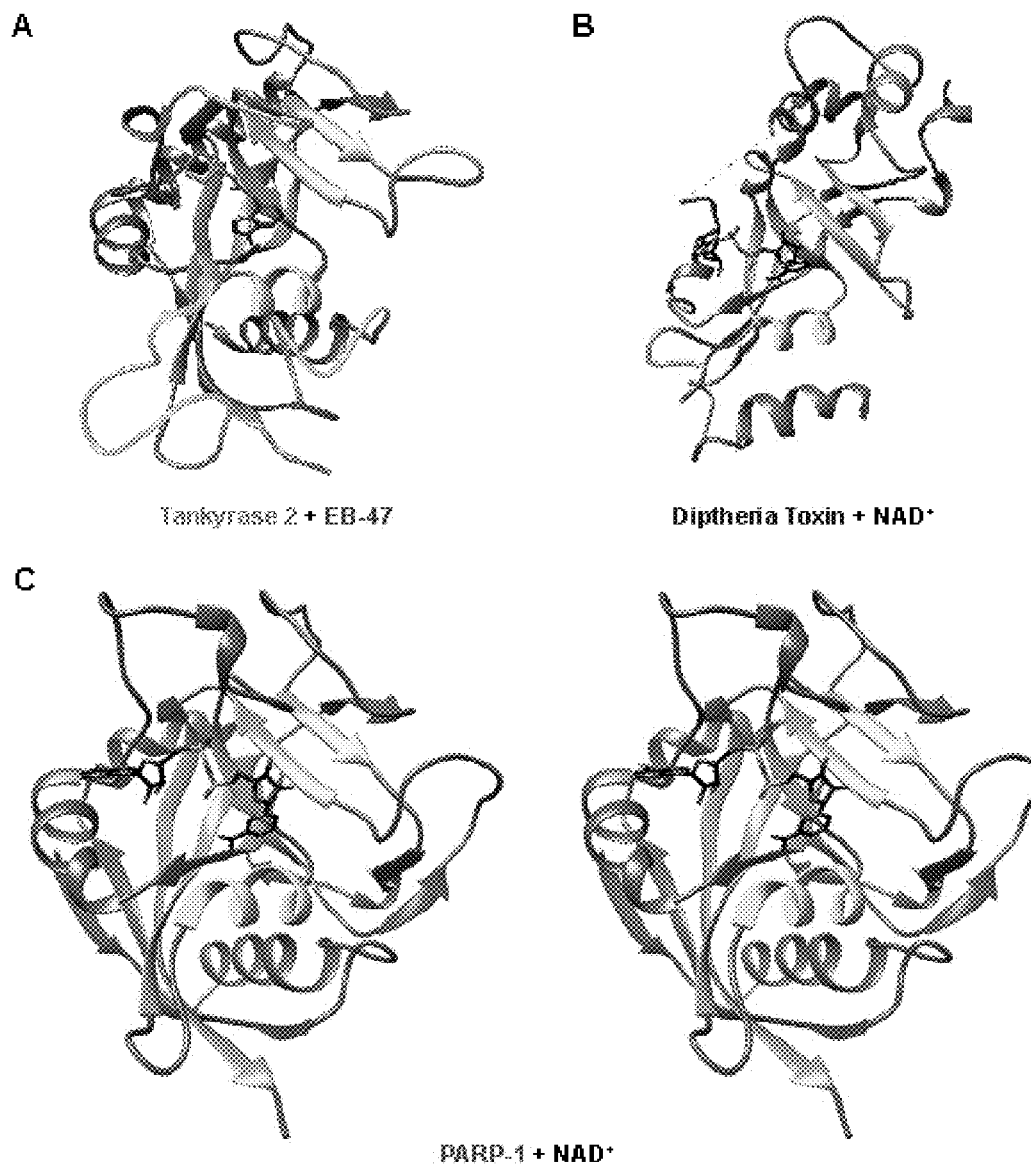
FIGS. 9A-C

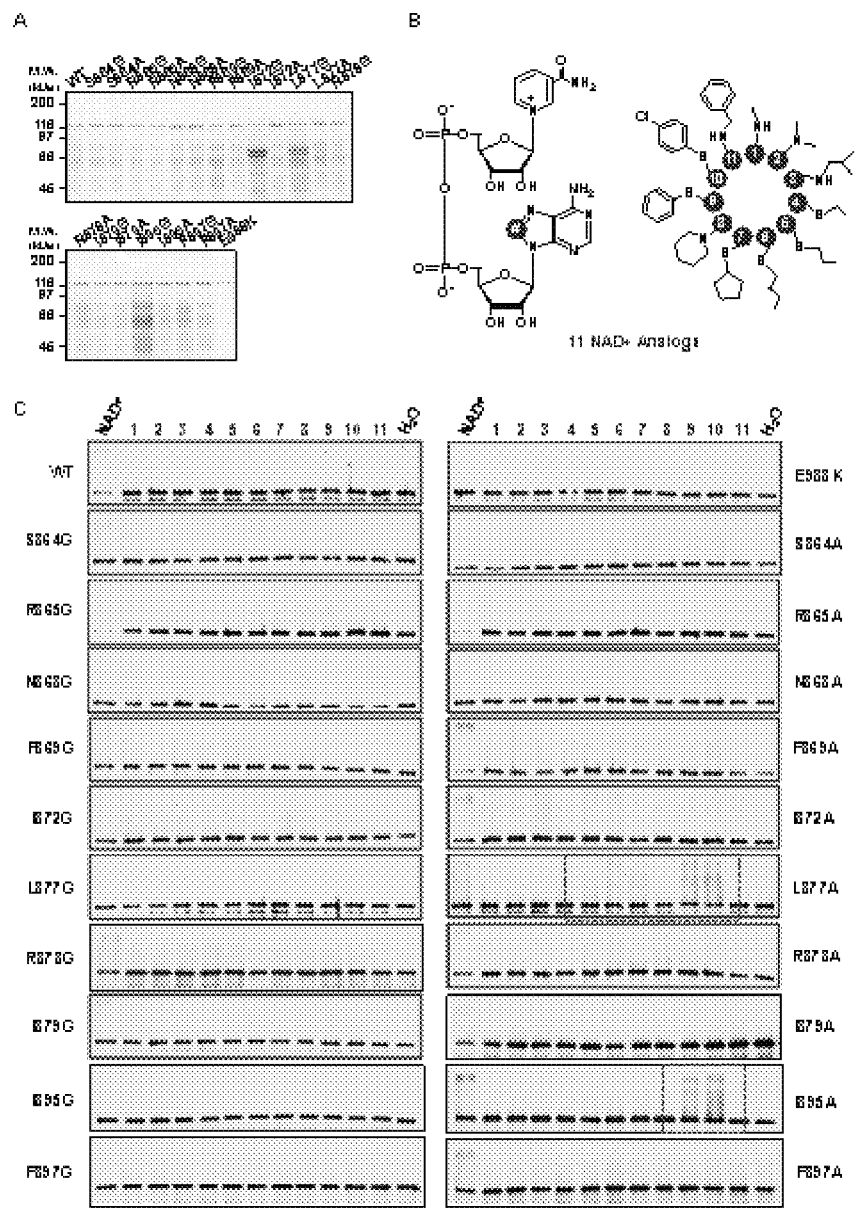
FIGS. 10A-C

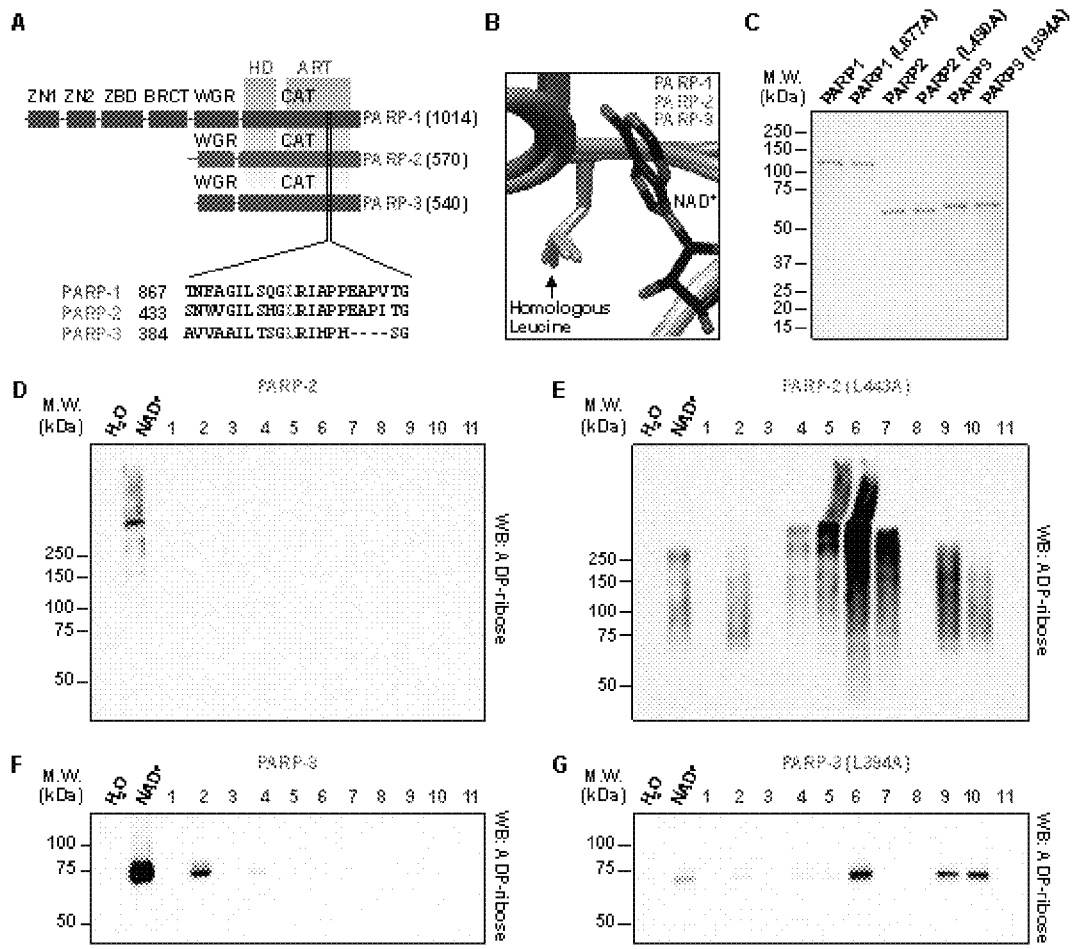
FIGS. 11A-G

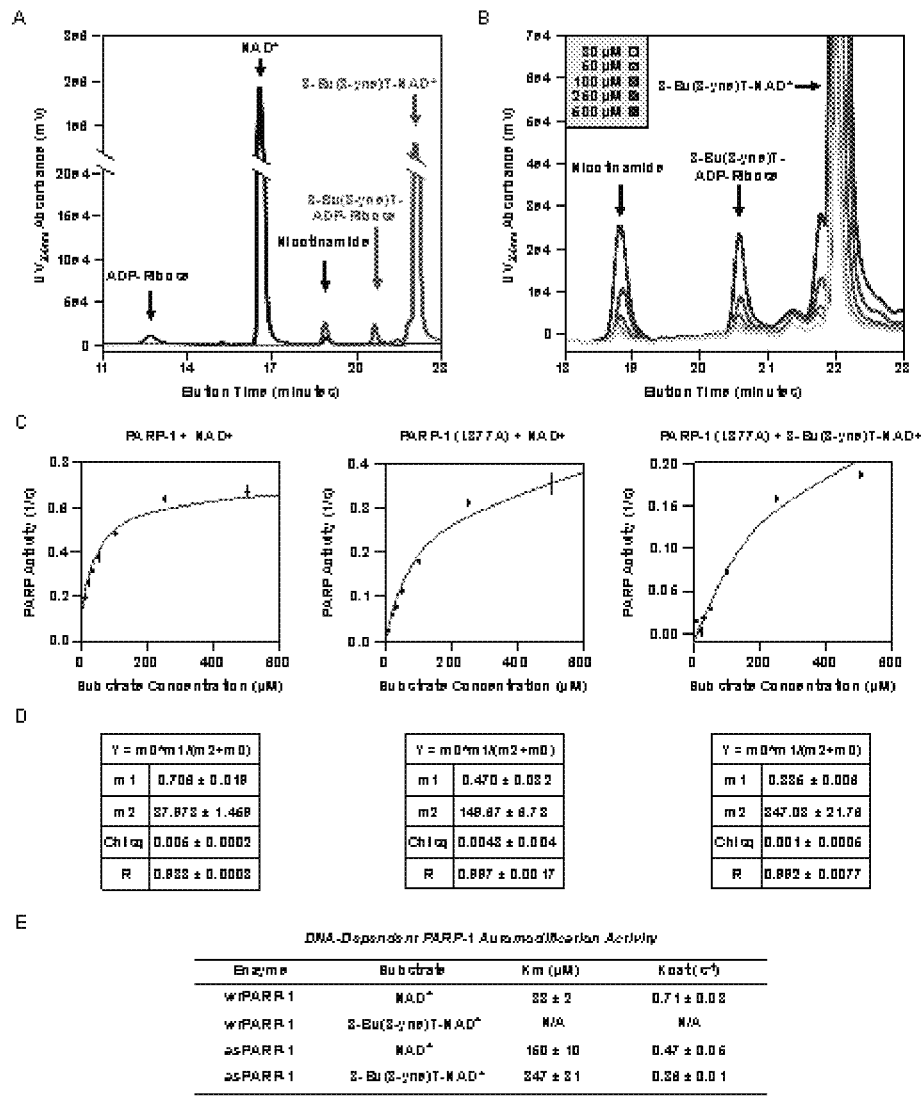
FIGS. 12A-E

FIGS. 15A-D

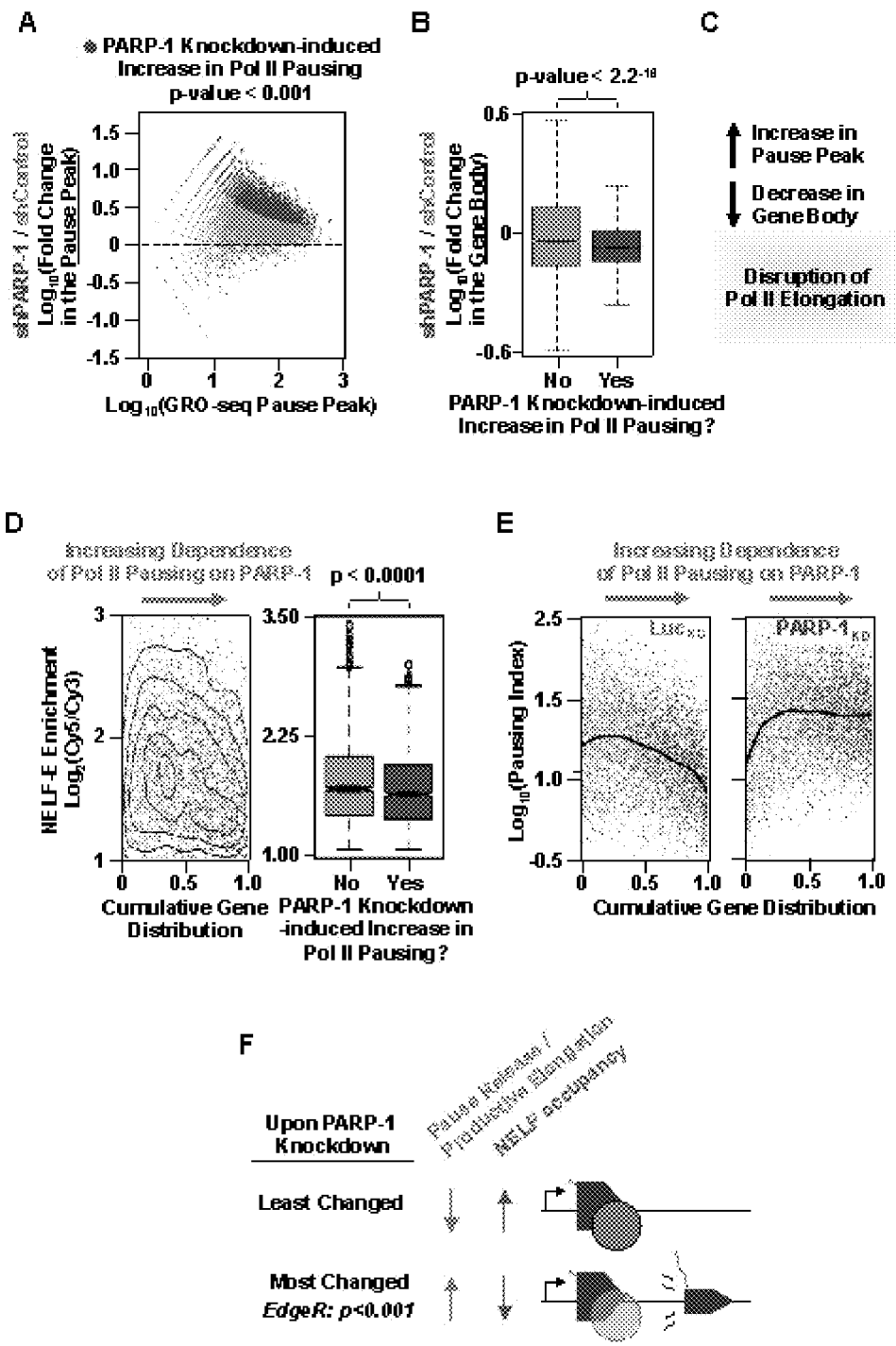
FIGS. 17A-F

NAD ANALOGS AND METHODS OF USING SAID NAD ANALOGS IN DETERMINING RIBOSYLATION OF PROTEINS WITH PARP MUTANTS

PRIORITY CLAIM

This application claims benefit of priority to U.S. Provisional Application Ser. No. 62/144,711, filed Apr. 8, 2015, the entire contents of which are hereby incorporated by reference.

This invention was made with government support under grant number R01 DK069710 ("The Role of PARP-1 in Hormone-Regulated Transcription") awarded by the National Institutes of Health/National Institute of Diabetes and Digestive and Kidney Diseases and grant number GM086703 awarded by the National Institutes of Health. The government has certain rights in the invention.

BACKGROUND

1. Field

This application relates to new chemical compounds, PARP-1 mutants and methods of use therewith. In some aspects, the present disclosure provides NAD analogs which may be used to determine the protein identity and the amino acid sequence wherein the ribosylation occurred.

2. Related Art

ADP-ribose is a naturally-occurring small molecule with a variety of functions. It is commonly found linked to proteins as a post-translational modification. Mono-ADP-ribose (MAR) and poly-ADP-ribose (PAR) transferase enzymes (generally known as PARP enzymes) catalyse the transfer (and in the case of PAR transferase enzymes, polymerization) of ADP-ribose units from $NAD^+$, which can be covalently linked glutamate, aspartate, and lysine residues of acceptor proteins. DNA-strand breakage has been considered the main trigger of MAR and PAR synthesis, leading either to repair of the damaged site and cell survival, or cell death, depending on the cellular context and on the intensity of the DNA insult. However, other cellular components (e.g., interacting proteins, nucleosomes, posttranslational modifications, etc.) may also stimulate MAR and PAR synthesis and the size and branching of PAR synthesized under normal conditions is still unclear.

There are at present 18 PARP family members, and it remains to be determined whether all PARP family members can effectively synthesize MAR and/or PAR and, if so, whether the enzymes produce structures comparable to that synthesized by PARP1. Some PARP family members appear to lack conserved residues crucial for polymer elongation and may instead be mono(ADP-ribose) transferases. A detailed biochemical characterization of each PARP family member is necessary to answer the numerous questions that remain regarding PAR synthesis, transfer, function and degradation but mechanisms and methods to do so are still lacking. Thus, new compounds and methods to determine information about the activity of each PARP enzyme are needed.

SUMMARY

In some aspects, the present disclosure provides NAD analogs which may be used to determine the target protein of PARP protein. In other aspects, the NAD analogs may be used to identify the amino acid sequence ribosylated.

In another aspect, the present disclosure provides compounds of the formula:

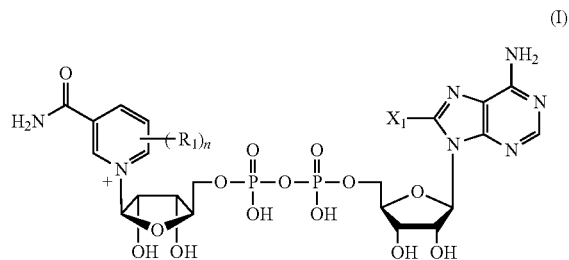

(I)

wherein:
  $X_1$ is $-A_1-Y_1$, wherein:
    $A_1$ is $-O-$, $-S-$, or $-NR_2-$;
      wherein: $R_2$ is hydrogen, $alkyl_{(C \le 6)}$, or substituted $alkyl_{(C \le 6)}$; and
    $Y_1$ is $alkyl_{(C \le 12)}$, $alkenyl_{(C \le 12)}$, $alkynyl_{(C \le 12)}$, $aryl_{(C \le 12)}$, $aralkyl_{(C \le 12)}$, $heteroaryl_{(C \le 12)}$, $acyl_{(C \le 12)}$, $alkoxy_{(C \le 12)}$, or a substituted version of any of these groups; or
    $R_2$ and $Y_1$ are taken together and are $alkanediyl_{(C \le 8)}$, $alkoxydiyl_{(C \le 8)}$, $alkylaminodiyl_{(C \le 8)}$, or a substituted version of any of these groups;
  $X_1$ is $-A_2-L_1-Y_2$, wherein:
    $A_2$ is $-O-$, $-S-$, or $-NR_3-$;
      wherein: $R_3$ is hydrogen, $alkyl_{(C \le 6)}$, or substituted $alkyl_{(C \le 6)}$;
    $L_1$ is a linker; and
    $Y_2$ is a solid support, a biotin, a fluorophore, a protein, an enzyme, a DNA sequence, or an antibody;
  $R_1$ is amino, aminosulfonyl, carboxy, cyano, halo, hydroxy, hydroxysulfonyl, hydroxyamino, mercapto, nitro, or
  $alkyl_{(C \le 6)}$, $alkoxy_{(C \le 6)}$, $acyloxy_{(C \le 6)}$, $alkylamino_{(C \le 6)}$, $dialkylamino_{(C \le 6)}$, $amido_{(C \le 6)}$, or a substituted version of any of these groups; and
  n is 0, 1, 2, 3, or 4;
or a salt, a reduced form, or tautomer thereof. In some embodiments, the compound is further defined as:

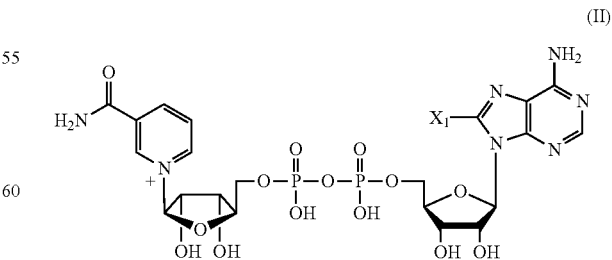

(II)

wherein: $X_1$ is as defined above or a salt, a reduced form, or tautomer thereof. In some embodiments, the compound is further defined as:

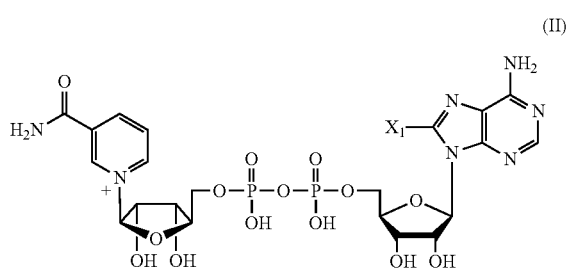

(II)

wherein:
X₁ is -A₁-Y₁, wherein:
A₁ is —O—, —S—, or —NR₂—;
wherein: R₂ is hydrogen, alkyl$_{(C\leq 6)}$, or substituted alkyl$_{(C\leq 6)}$; and
Y₁ is alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, acyl$_{(C\leq 12)}$, alkoxy$_{(C\leq 12)}$, or a substituted version of any of these groups; or
R₂ and Y₁ are taken together and are alkanediyl$_{(C\leq 8)}$, alkoxydiyl$_{(C\leq 8)}$, alkylaminodiyl$_{(C\leq 8)}$, or a substituted version of any of these groups;
or a salt, a reduced form, or tautomer thereof.

In some embodiments, A is —S—. In other embodiments, A is —NH—. In some embodiments, Y₁ is alkyl$_{(C\leq 12)}$ or substituted alkyl$_{(C\leq 12)}$. In other embodiments, Y₁ is alkynyl$_{(C\leq 12)}$ or substituted alkynyl$_{(C\leq 12)}$. In some embodiments, Y₁ is 3-butynyl (i.e. 3-butyn-1-yl). In other embodiments, Y₁ is aryl$_{(C\leq 12)}$ or substituted aryl$_{(C\leq 12)}$. In other embodiments, Y₁ is alkoxy$_{(C\leq 12)}$ or substituted alkoxy$_{(C\leq 12)}$. In some embodiments, n is 0. In other embodiments, the compound is further defined as:

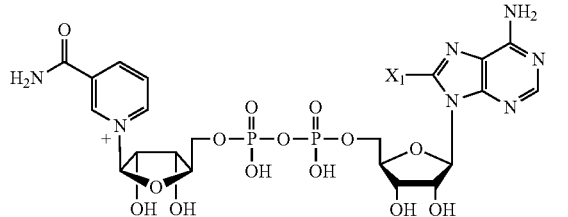

(II)

wherein:
X₁ is -A₂-L₁-Y₂, wherein:
A₂ is —O—, —S—, or —NR₃—;
wherein: R₃ is hydrogen, alkyl$_{(C\leq 6)}$, or substituted alkyl$_{(C\leq 6)}$;
L₁ is a linker; and
Y₂ is a solid support, a biotin molecule, a fluorophore, a protein, an enzyme, a DNA sequence, or an antibody;
or a salt, a reduced form, or tautomer thereof.

In some embodiments, A is —S—. In other embodiments, A is —NH—. In some embodiments, L₁ is a linker which comprises a 1,2,3-triazole. In some embodiments, L₁ is a linker which comprises the group:

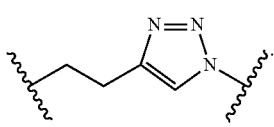 [SMILES: *CCc1cn(*)nn1]

In some embodiments, Y₂ is a protein. In other embodiments, Y₂ is biotin. In other embodiments, Y₂ is a fluorophore. In some embodiments, the compound is further defined as:

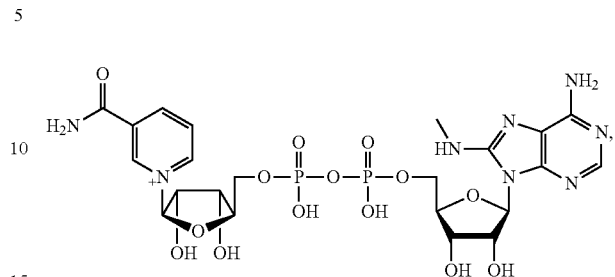

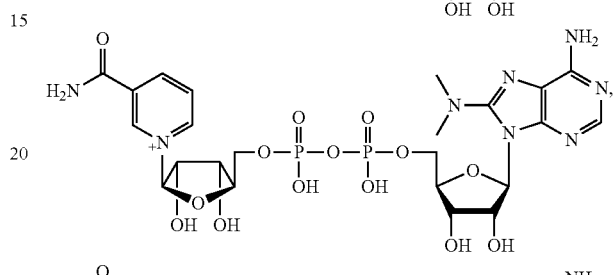

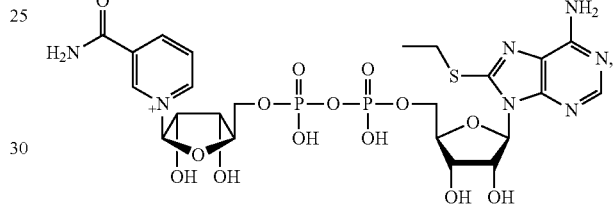

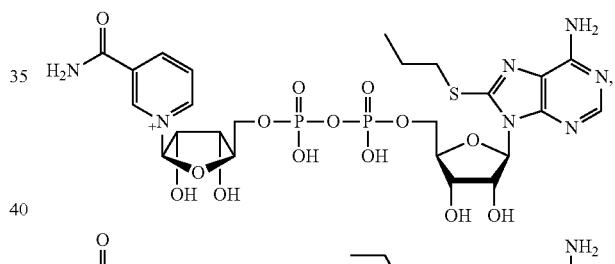

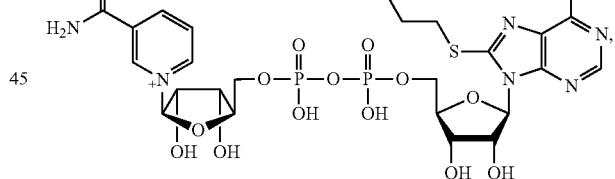

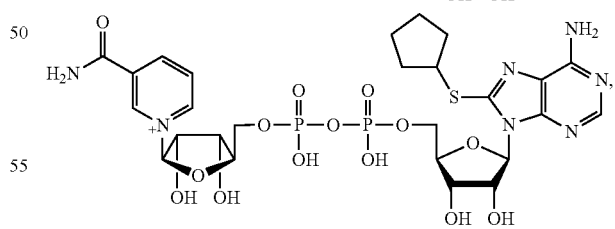

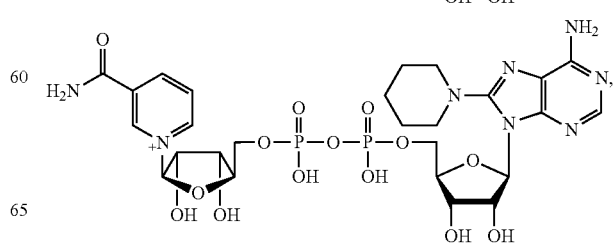

-continued

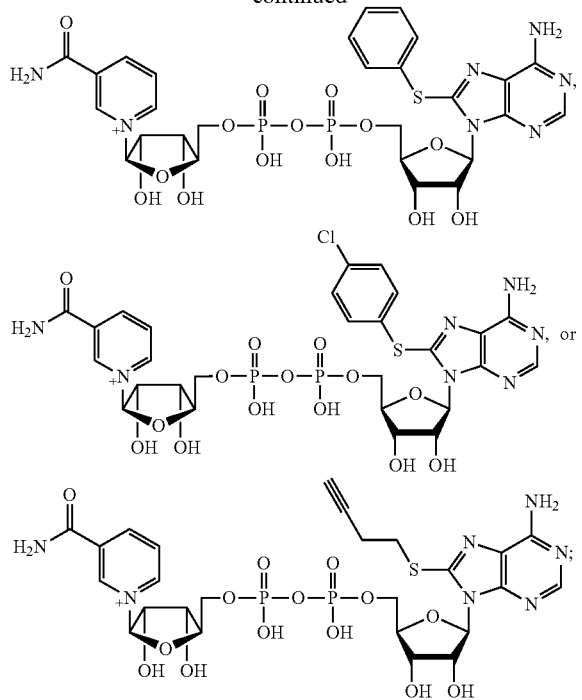

or a salt, a reduced form, or tautomer thereof. In some embodiments, the compound is further defined as:

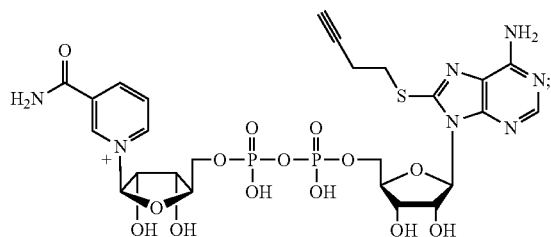

or a salt, a reduced form, or tautomer thereof. In some embodiments, the salt comprises a cation selected from the group consisting of a Group 1 metal cation, Group 2 metal cation, and a compound comprising a protonated ammonium, a protonated monoalkylammonium, a protonated dialkylammonium, a protonated trialkylammonium, or a tetraalkylammonium. In some embodiments, the cation is sodium, potassium, lithium, magnesium, calcium, ammonium, tetramethylammonium, choline, or a protonated amino acid.

In still another aspect, the present disclosure provides methods of identifying a target protein wherein an amino acid on the target protein is ribosylated by a PARP protein comprising:
(A) providing a PARP protein comprising a mutation in the NAD binding site;
(B) incubating the PARP protein with an NAD analog described herein and a cell or a cellular extract under conditions sufficient to ribosylate the target protein; and
(C) identifying the target protein ribosylated with the NAD analog.

In some embodiments, the PARP protein is PARP-1, PARP-2, PARP-3, vPARP, Tankyrase 1, Tankyrase 2, TiPARP, PARP12, PARP13, PARP9, PARP14, PARP15, PARP10, PARP11, PARP6, PARP8, or PARP16. In some embodiments, the PARP protein is PARP-1, PARP-2, or PARP-3. In some embodiments, the PARP protein is a mammalian PARP protein. In some embodiments, the PARP protein is a mouse or human PARP protein. In some embodiments, the mutation is a mutation of a conserved leucine or isoleucine residue in the NAD binding site to an alanine. In some embodiments, the mutation in PARP-1 is L877A or I895A. In some embodiments, the mutation in the NAD binding site allows the PARP protein to carry out ribosylation with the NAD analog. In some embodiments, the PARP protein is expressed in the cell.

In some embodiments, the methods further comprise incubating the NAD analog, the PARP protein, and the cellular extract with a polynucleotide. In some embodiments, the polynucleotide is genomic DNA that has been sheared and digested to generate free ends or a short synthetic double stranded DNA.

In some embodiments, step (B) further comprises:
(D) isolating the target protein having a portion of the NAD analog with the adenine moiety attached thereto.

In some embodiments, the methods further comprise reacting the NAD analog with an azide containing biotin molecule to form a biotin containing NAD analog after step (B). In some embodiments, the target protein ribosylated with the NAD analog is immobilized with streptavidin during step (C). In some embodiments, the methods further comprises isolating the target protein by reacting the NAD analog with an azide containing solid support. In some embodiments, isolating the target protein further comprises reacting the NAD analog with an azide containing fluorophore. In some embodiments, the target protein is isolated using immobilization, gel electrophoresis, protein extraction, or immunoprecipitation. In some embodiments, the target protein is identified by mass spectroscopy, nuclear magnetic resonance, or immunological detection methods.

In some embodiments, the methods further comprise:
(E) digesting the target protein with a protease;
(F) identifying the amino acid on the target protein ribosylated by the PARP protein.

In some embodiments, the protease is an endoproteinase. In some embodiments, the protease is trypsin, chymotrypsin, Glu-C endoproteinase, or Lys-C endoproteinase. In some embodiments, the amino acid is identified using mass spectroscopy, nuclear magnetic resonance imaging, Edman degradation, thin layer chromatography, or immulogical methods.

In some embodiments, the target protein is ribosylated once. In some embodiments, the target protein is ribosylated two or more times. In some embodiments, the methods are performed in vitro. In some embodiments, the methods are performed in an isolated nucleus. In some embodiments, the cellular extract is a nuclear extract. In some embodiments, the methods are performed in a whole or intact cell.

In still yet another aspect, the present disclosure provides methods of identifying a DNA sequence in a chromatin complex, wherein the chromatin complex contains a protein which is ribosylated by a PARP protein, comprising:
(A) obtaining a cellular extract comprising a chromatin complex having a DNA strand and one or more proteins;
(B) incubating the chromatin with a mutated PARP protein and an NAD analog described herein under conditions sufficient to ribosylate the protein in the chromatin complex;

(C) separating the chromatin complex from the cellular extract comprising immobilizing the ribosylated protein on a support and eluting away the cellular extract;
(D) isolating the DNA from the chromatin complex; and
(E) identifying the DNA sequence.

In some embodiments, the cellular extract is from a cell expressing a mutated PARP protein. In some embodiments, the DNA sequence is identified by sequencing or hybridization. In some embodiments, the sequencing is qPCR or deep sequencing.

In some embodiments, the methods further comprise reversibly crosslinking the DNA and the ribosylated protein after step (B). In some embodiments, the DNA and the ribosylated protein are crosslinked with formaldehyde. In some embodiments, the cellular extract is an extract of the cell's nucleus. In some embodiments, the mutated PARP protein contains a mutation to allow the incorporation of the NAD analog onto the protein.

In some embodiments, immobilizing the ribosylated protein to a support comprises:
(A) attaching a biotin molecule to the ribosylated protein by a chemical moiety on a portion of the NAD analog; and
(B) exposing the chromatin complex to an avidin containing support.

In yet another aspect, the present disclosure provides methods of identifying an amino acid ribosylated on a target protein by a PARP protein comprising:
(A) providing a PARP protein comprising a mutation in the NAD binding site;
(B) incubating the PARP protein with an NAD analog described herein and a cell or a cellular extract under conditions sufficient to ribosylate the target protein to form a ribosylated target protein;
(C) immobilizing the ribosylated target protein by reacting the NAD analog with an immobilizing agent;
(D) digesting the ribosylated target protein with a protease; and
(E) analyzing a digest of the ribosylated target protein to identify the ribosylated amino acid.

It is contemplated that any method or composition described herein can be implemented with respect to any other method or composition described herein.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

(FIG. 1A) The PARP family of proteins has 18 members which are defined by a conserved PARP catalytic domain (shown in dark gray) (Hakmé et al., 2008). (FIG. 1B) Determining which PARP family members are responsible for ADP-ribosylation events in a cell can be very difficult due to their overlapping substrate usage and end-product. (FIG. 1C) PARPs may perform mono-ADP-ribosylation (MARylation), oligo-ADP-ribosylation (OARylation), or poly-ADP-ribosylation (PARylation). Some PARP proteins are thought to be enzymatically inactive (PARPs 9, 13, and TPT1).

FIG. 3—ADP-ribosylation of HeLa cell nuclear extract proteins by analog-sensitive PARP-1, PARP-2, and PARP-3 mutants in the presence of 8-Bu(3-yne)T-NAD$^+$: Schematic of the experimental set-up for NAD$^+$ analog-sensitive-dependent 8-Bu(3-yne)T-ADP-ribosylation of proteins in a HeLa cell nuclear extract.

(FIG. 4A) Schematic of the experimental approach for asPARP-dependent labeling of proteins in intact nuclei. (FIG. 4B) Nuclei from Parp1$^{-/-}$ MEFs with ectopic expression of wild-type PARP-1 (Wt) or asPARP-1 (L877A) were incubated with 8-Bu(3-yne)T-NAD$^+$. The 8-Bu(3-yne)T-ADP-ribosylated nuclear proteins were extracted, run on a 10% PAGE-SDS resolving gel, and analyzed by in-gel fluorescence (ex: 532 nm, em: 605 nm) following copper-catalyzed cycloaddition to azido-rhodamine. A Western blot for β-actin (bottom) from the same samples serves as a loading control. The molecular weights (MW) in kilodaltons (kDa) of marker proteins run on the same gels are shown.

FIGS. 5A-I—Structure-based engineering of an NAD+ analog-sensitive PARP-1 (asPARP-1) mutant: (FIG. 5A) Schematic illustrating the logic of engineering NAD+ analog-sensitivity in PARP proteins. (FIG. 5B) Depiction of residues in PARP-1, in orange, within the PARP-1 active site (top) and in the context of the PARP-1 amino acid sequence (bottom) selected for mutation to glycine or alanine for discovery of a gatekeeper position which might confer NAD+ analog-sensitivity. (FIG. 5C) Chemical structures of the 11 NAD+ analogs used in screening for analog-sensitive PARP-1 activity. (FIG. 5D) Comparison of relative automodification activity of purified wild-type and mutant PARP-1 proteins with NAD+ and NAD+ analogs (in black and purple, respectively). The PARP-1 automodification signals (in relative units; R.U.) were determined by densitometry of ADPribosylation-induced shifts of PARP-1 mobility in Western blot assays. (FIG. 5E) Western blot for ADP-ribose from automodification reactions containing PARP-1 or PARP-1 mutants (L877A and I895A) and NAD+ or NAD+ analogs. WB=Western blot. (FIG. 5F) Depiction of the spatial relationship between position 8 of the adenine ring in NAD+ and the gatekeeper residues from a structural model of the PARP-1 catalytic domain with NAD+ aligned in its active site (see details in FIGS. 9A-C). The dashed arrow indicates the distance, in angstroms (Å), between the position 8 and the indicated Cγ of Leucine 877. (FIG. 5G) Chemical structure of the bi-functional NAD+ analog 8-Bu (3-yne)T-NAD+ with the clickable analog sensitivity-inducing, alkyne-containing R group highlighted in red. (FIG. 5H) Schematic illustrating asPARP activity-dependent, click chemistry-mediated covalent attachment of fluorophores, biotin, or agarose resin to 8-Bu(3-yne)T-ADP-ribosylated proteins. (FIG. 5I) Automodification reactions with wild-type or analog-sensitive PARP-1, PARP-2, and PARP-3 analyzed by Western blotting for ADP-ribose (top) or in-gel fluorescence (excitation: 532 nm, emission: 605 nm) following copper-catalyzed cycloaddition to azido-rhodamine (bottom).

FIGS. 6A-H—Using analog-sensitive PARP-1 mutants to unambiguously identify the ADPribosylation targets of DNA-dependent PARPs: (FIG. 6A) In-gel fluorescence (ex: 532 nm, em: 605 nm) of HeLa cell nuclear extract proteins conjugated to azido-TAMRA using copper-catalyzed cycloaddition following 8-Bu(3-yne)TADP-ribosylation reactions with 8-Bu(3-yne)T-NAD+ in the presence of wild-type (wt) or analog-sensitive (as) PARP-1, PARP-2, or PARP-3. (FIG. 6B) Depiction of the strategy for LC-MS/MS detection of PARP-specific ADP-ribosylation sites. HeLa cell nuclear extract (N.E.) is incubated with a single purified recombinant analog sensitive PARP (asPARP) in the presence of 8-Bu(3-yne)T-NAD+. Following in vitro modification, the extract proteins are covalently linked to azido-agarose beads via copper-catalyzed cycloaddition. The conjugated beads are washed, trypsinized to release peptides for protein identification, and then washed again. The remaining peptides containing ADP-ribosylation sites are eluted from the resin using hydroxylamine ($NH_2OH$). The cleaved modification produces a 15.0109 Dalton increase in mass yielding a signature m/z change during LC-MS/MS identifying the specific site of glutamate or aspartate modification. Both the tryptic digest and hydroxylamine eluate are subjected to LC-MS/MS analysis. (FIG. 6C) The number of unique ADP-ribosylation sites and protein targets identified for PARP-1, PARP-2, and PARP-3 using the LC-MS/MS approach illustrated in FIG. 6B. (FIG. 6D) Venn diagram depicting the overlap of the protein targets of PARP-1, PARP-2 and PARP-3. (FIG. 6E) Gene ontology terms enriched for the sets of PARP-1, PARP-2 and PARP-3 targets, with both the p-value and percent of total targets included for selected enriched GO terms. (FIG. 6F) Selected targets of PARP-specific ADP-ribosylation identified using asPARP-1, asPARP-2, and asPARP-3. (FIG. 6G) Enriched amino acid sequences±8 residues on either side of identified PARP-1, PARP-2, and PARP-3 ADP-ribosylation sites. aa=amino acids. (FIG. 6H) Histogram of the two-dimensional relationship between previously identified PARylation sites (7) and ADP-ribosylation sites identified using the PARP-specific LC-MS/MS approach described herein.

FIGS. 7A-H—P-TEFb-dependent ADP-ribosylation of NELF by PARP-1: (FIG. 7A) Cumulative distribution of enriched 7-mer amino acid sequences±50 residues from PARP-1, 2, and 3 ADP-ribosylation sites. The PARP-1 target-predictive sequence RSRSRDR is highlighted. (FIG. 7B) Schematic showing the distribution of PARP-1 ADP-ribosylation sites, P-TEFb phosphorylation sites, and the PARP target-enriched 7-mer RSRSRDR on proteins in the NELF complex. (FIG. 7C) Histogram of the two-dimensional relationship between ADP-ribosylation sites identified herein and the nearest incidence of known phosphorylation modifications on PARP target proteins. (FIG. 7D) Western blot analysis of immunoprecipitated FLAG-tagged NELF-E or GFP from 293T cells. (FIG. 7E) Silver stained SDS-PAGE gel (left) and ADP-ribose Western blot (right) of immunopurified NELF complex showing ADP-ribosylated proteins migrating at the expected molecular weights of NELF-E and NELF-A. The asterisk indicates an ADP-ribosylated protein migrating at the expected molecular weight of PARP-1. (FIG. 7F) Western blot for ADP-ribose of in vitro modification reactions containing GST, GST-tagged wild-type NELF-E, or GST-tagged ADP-ribosylation site point mutant NELF-E, PARP-1, and NAD+ as indicated. (FIG. 7G) Western blot analysis of immunoprecipitated FLAG-tagged NELF-E from 293T cells treated with vehicle, the PARP inhibitor PJ34, or the P-TEFb/CDK9 inhibitor flavopiridol. (FIG. 7H) NELF-E/TAR RNA electrophoretic mobility shift assay with or without PARP-1-mediated ADP-ribosylation. GST or GST-NELF-E was titrated between 0.1 to 1.0 µM and NAD+ was added at 25 µM (+) or 100 µM (++) during the ADP-ribosylation reaction.

FIGS. 8A-H—Functional links between PARP-1-catalyzed ADP-ribosylation, NELF binding, and RNA polymerase II pausing genome-wide: (FIG. 8A) Schematic representation of Click-ChIP-seq, an asPARP-1-based method for identifying the genome-wide distribution of PARP-1-catalyzed ADP-ribosylation. (FIG. 8B) Genome browser view of a multi-gene locus of the mouse genome showing PARP-1-catalyzed ADP-ribosylation (from Click-ChIP-seq), NELF-E and H3K4me3 enrichment (from ChIP-seq), and transcription (from GRO-seq). (FIG. 8C) Genome-wide correlations between the enrichment of chromatin- and transcription-related proteins, histone modifications, and PARP-1-catalyzed ADP-ribosylation. Asterisks indicate proteins with previously reported physical or genetic interactions with PARP-1 (Yu et al., 2004, O'Neil et al., 2013 and Bailey et al., 2014). (FIG. 8D) Heatmap representations showing PARP-1-catalyzed ADP-ribosylation (from Click-ChIPseq), NELF-E, PARP-1, and H3K4me3 enrichment (from ChIP-seq), and transcription (from GRO-seq) at the promoters of all RefSeq genes [±5 kb on either side of the annotated transcription start sites (TSSs)]. The data, which are from MEF cells, are ordered bottom to top based on increasing transcription. (FIG. 8E) Heatmap representation of RNA polymerase II pausing indices at RefSeq promoters ranked by PARP-1 activity or CDK9 occupancy. (FIG. 8F) Genome browser view of a representative locus of the human genome containing the gene CTNNB1, showing normalized GRO-seq read density from MCF-7 cells subjected to shRNA-mediated knockdown with either control/luciferase (LucKD, left) or PARP-1 (PARP-1KD, right) shRNAs. Pink arrows indicate the location of the altered peak of paused Pol II. (FIG. 8G) Metagene of GRO-seq read density at the promoters of all expressed RefSeq genes from MCF-7 cells subjected to shRNA-mediated knockdown with either control/luciferase or PARP-1 shRNAs. (FIG. 8H) RNA polymerase II pausing indices at the promoters of all transcribed RefSeq genes from MCF-7 cells subjected to shRNA-mediated knockdown with either control/luciferase or PARP-1 shRNAs.

FIGS. 9A-C. Structure-based alignment of $NAD^+$ in the catalytic domain of PARP-1. (FIG. 9A) Structure of the Tankyrase 2 catalytic domain with EB-47 (PDBID:4BJ9), a PARP inhibitor that has a chemical structure related to $NAD^+$. Tankyrase 2 and EB-47 are in grey and purple, respectively. The beta-sheets and alpha-helical folds in the conserved ADP-ribosyltransferase secondary structure are colored in orange and yellow, respectively. (FIG. 9B) Structure of Diptheria toxin with $NAD^+$ (PDBID:1TOX) in blue and black, respectively. The conserved ADP-ribosyltransferase secondary structure colored as in FIG. 17A. (FIG. 9C) Alignment of $NAD^+$ into the catalytic domain of PARP-1, based on 1TOX and 4BJ9, as well as a structure of PARP-1 with the inhibitor 3-methoxybenzamide (PDBID:3PAX), shown in a stereoscopic view. The $NAD^+$ and PARP-1 are colored in black and green, respectively, with the conserved ADP-ribosyltransferase secondary structure colored as in FIG. 9A.

FIGS. 10A-C. Screening for an $NAD^+$ analog-sensitive PARP-1 mutant using an activity-based screen. (FIG. 10A) Recombinant PARP-1 proteins used in the analog-sensitive PARP-1 activity screen. Expression of $His_{10}$-tagged wild-type PARP-1 and 21 PARP-1 site-specific mutants in E. coli and purification using nickel-NTA affinity chromatography. The mutants were designed around the adenine ring of $NAD^+$. Coomassie stained SDS-PAGE gel of the purified proteins. Molecular weight (M.W.) markers in kilodaltons (kDa) are shown. (FIG. 10B) Chemical structures of the 11 $NAD^+$ analogs used in screening for analog-sensitive PARP-1 (asPARP-1) activity. The R groups, which are shown in the "wheel" on the right, are linked at position 8 of the adenine ring of $NAD^+$ (#). (FIG. 10C) Western blot analyses of the asPARP-1 mutant automodification reactions performed with $NAD^+$ or the $NAD^+$ analogs shown in FIG. 10B using an anti-PARP-1 antibody. Dashed red boxes highlight positive hits from the screen as indicated by an auto PARylation-induced migration shift of PARP-1 with the $NAD^+$ analog.

FIGS. 11A-G. Transfer of $NAD^+$ analog sensitivity to other PARP family members. (FIG. 11A) Schematic of the domain structures of PARP-1, PARP-2, and PARP-3 aligned based on the catalytic domain (CAT) (top). Amino acid sequences flanking the homologous gatekeeper residue (L, in orange) in PARP-1, PARP-2, and PARP-3 (bottom). PARP-1, PARP-2, and PARP-3 are colored in green, pink, and blue, respectively. ZN1, zinc finger 1; ZN2, zinc finger 2; ZBD; zinc binding domain; WGR, WGR repeat domain; CAT, catalytic domain; HD, helical domain; ART; ADP-ribosyltransferase domain. (FIG. 11B) Depiction of the binding site for $NAD^+$ (black), which was modeled into PARP-1 (green), PARP-2 (pink), and PARP-3 (blue). The homologous leucine gatekeeper residues within the PARP-1, PARP-2, and PARP-3 catalytic domains are indicated. (FIG. 11C) SDS-PAGE analysis, with subsequent staining using Coomassie blue, of purified FLAG-tagged PARP-1, PARP-1 (L877A), PARP-2, PARP-2 (L443A), PARP-3, and PARP-3 (L394A) expressed in Sf9 insect cells. Molecular weight (M.W.) markers in kilodaltons (kDa) are shown. (FIGS. 11D-G) Western blot analyses of wild-type and analog-sensitive PARP-2 and PARP-3 automodification reactions performed with $NAD^+$ or the $NAD^+$ analogs shown in FIG. 10B using an ADP-ribose detection reagent. (FIG. 11D) PARP-2, (FIG. 11E) PARP-2 (L443A), (FIG. 11F) PARP-3, and (FIG. 11G) PARP-3 (L394A).

FIGS. 12A-E. Enzyme kinetics of asPARP-1 with 8-Bu (3-yne)T-$NAD^+$. (FIG. 12A) LC-HPLC traces of $NAD^+$- or 8-Bu(3-yne)T-$NAD^+$-derived small molecules from automodification reactions containing PARP-1 with 500 μM $NAD^+$ (black traces) or PARP-1 (L877A) with 100 μM 8-Bu(3-yne)T-$NAD^+$. (red traces). (FIG. 12B) LC-HPLC traces showing 8-Bu(3-yne)T-$NAD^+$ concentration-dependent production of small molecules produced from an automodification reaction containing PARP-1 (L877A) with the $NAD^+$ analog. (FIG. 12C) Saturation curves for PARylation activity with PARP-1 and $NAD^+$ (left), PARP-1 (L877A) and $NAD^+$ (middle), and PARP-1 (L877A) and 8-Bu(3-yne) T-$NAD^+$ (right). No saturation was detectable for PARP-1 and 8-Bu(3-yne)T-$NAD^+$ (data not shown). (FIG. 12D) Quantification of Michaelis-Menten enzyme kinetics parameters from the saturation curves shown in FIG. 12C for PARP-1 and $NAD^+$ (left), PARP-1 (L877A) and $NAD^+$ (middle), and PARP-1 (L877A) and 8-Bu(3-yne)T-$NAD^+$ (right). (FIG. 12E) Summary of Michaelis-Menten enzyme kinetics parameters for PARP-1 and PARP-1 (L877A) with $NAD^+$ and 8-Bu(3-yne)T-$NAD^+$.

(FIG. 15A) Re-expression of PARP-1 in $Parp1^{-/-}$ MEFs. Western blot analyses of PARP-1 expression in PARP-1 knockout MEFs expressing a GFP control, wild-type PARP-1, or analog-sensitive PARP-1. (FIG. 15B) Confocal fluorescence microscopy of PARP-1-mediated ADP-ribosylation in intact nuclei from the $Parp1^{-/-}$ MEFs expressing wtPARP-1 or asPARP-1 described in FIG. 15A following addition of 8-Bu(3-yne)T-$NAD^+$. (FIG. 15C) Streptavidin-HRP-based dot blot of nuclear proteins (top) and ethidium bromide-stained agarose gel of streptavidin-purified genomic DNA (bottom) from azido-biotin clicked nuclear samples following a reaction with 8-Bu(3-yne)T-$NAD^+$ in $Parp1^{-/-}$ MEFs expressing wtPARP-1 or asPARP-1. (FIG. 15D) Quantitative PCR (qPCR) analysis of streptavidin-purified genomic DNA from Click-ChIP assaying for the proximal promoter regions of two expressed genes (Fkbp5 and Cebpa) in $Parp1^{-/-}$ MEFs expressing wtPARP-1 or asPARP-1.

FIGS. 17A-F. PARP-1 modulates the levels of RNA polymerase II pausing levels genome-wide in cells. (FIG. 17A) MA plot highlighting statistically significant changes (p-value <0.001; red dots) in normalized pause peak read counts (first 250 bp of gene) of RNA Polymerase II transcribed genes between replicates of control or PARP-1 knockdown MCF-7 cells as determined from GRO-seq data using edgeR (4). (FIG. 17B) $Log_{10}$ (-fold change) of normalized GRO-seq gene body read counts (for a region spanning 1-13 kb downstream of the TSS) between control and PARP-1 knockdown MCF-7 cells for genes that show (red; "Yes") or do not show (grey; "No") significant (p-value <0.001) differential read counts in the Pol II pause peak region of a transcribed gene. (FIG. 17C) Graphical representation of the relationship between Pol II pause peak and gene body read counts between control and PARP-1 knockdown cells. (FIG. 17D) Intensity of NELF-E enrichment at NELF-E ChIP peaks from a ChIP-chip microarray experiment in MCF-7 cells (5) across promoters (1) ordered by the extent of dependence of RNA polymerase II pausing on PARP-1 (red, genes that show increased Pol II pausing upon knockdown of PARP-1, p-value <0.001; grey, genes that do not show an increase in Pol II pausing upon knockdown of PARP-1) (left) or (2) segregated for genes that show (red; "Yes") or do not show (grey; "No") significant (p-value <0.001) differences in RNA polymerase II pausing (right). (FIG. 17E) Absolute value of the pausing indices for promoters ordered by the extent of dependence of RNA polymerase II pausing on PARP-1 for control (LucKD, left) or PARP-1 (PARP-1$_{KD}$, right) knockdown MCF-7 cells. Red, genes that show increased Pol II pausing upon knockdown of PARP-1, p-value <0.001; grey, genes that do not show an increase in Pol II pausing upon knockdown of PARP-1. (FIG. 17F) Schematic diagram summarizing the relationship between the extent of dependence of RNA polymerase II pausing on PARP-1, pausing index values, and NELF occupancy upon PARP-1 knockdown in MCF-7 cells.

DESCRIPTION OF ILLUSTRATIVE EMBODIMENTS

In some aspects, the present disclosure provides new NAD analogs which may be used with PARP enzymes to ribosylate a protein with the ADP-ribose group of the NAD analog. These NAD analogs may be used in methods to identify the protein ribosylated by a particular PARP enzyme. In some embodiments, the NAD analogs contain groups which contain reactive groups that can be used to selectively immobilize or identify the target protein. In some aspects, the NAD analogs may be used in methods to identify the DNA sequence bound to a protein within a specific chromatin protein.

I. ADP-RIBOSE

A. Structure

Adenosine diphosphate ribose (ADP-ribose) is a diphosphate ester between two ribose sugar units with a terminal adenosine moiety as shown in the structure below:

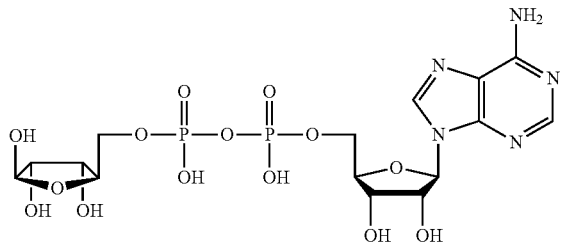

The ADP-ribose may be attached to a protein by PARP enzymatic activity. In some embodiments, the ADP-ribose exists in monomeric, oligomeric (2-10 units), and polymeric (11 to >200 units) forms or is attached to a protein in monomeric, oligomeric, or polymeric form. The molecules may be found in a free state or linked covalently through the free ribose moiety to proteins via a glutamic acid residue. PARP proteins may be used to catalyze the transfer of this ADP-ribose unit from an nicotinamide adenine dinucleotide (NAD) molecule. NAD has the structure:

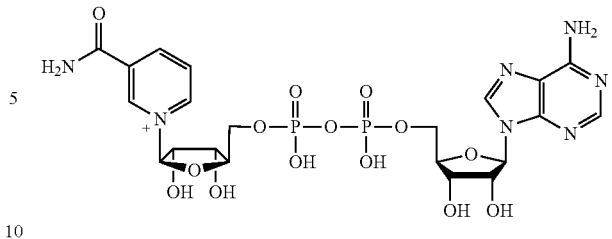

B. Function

Figures 1A, 1B, 1C:
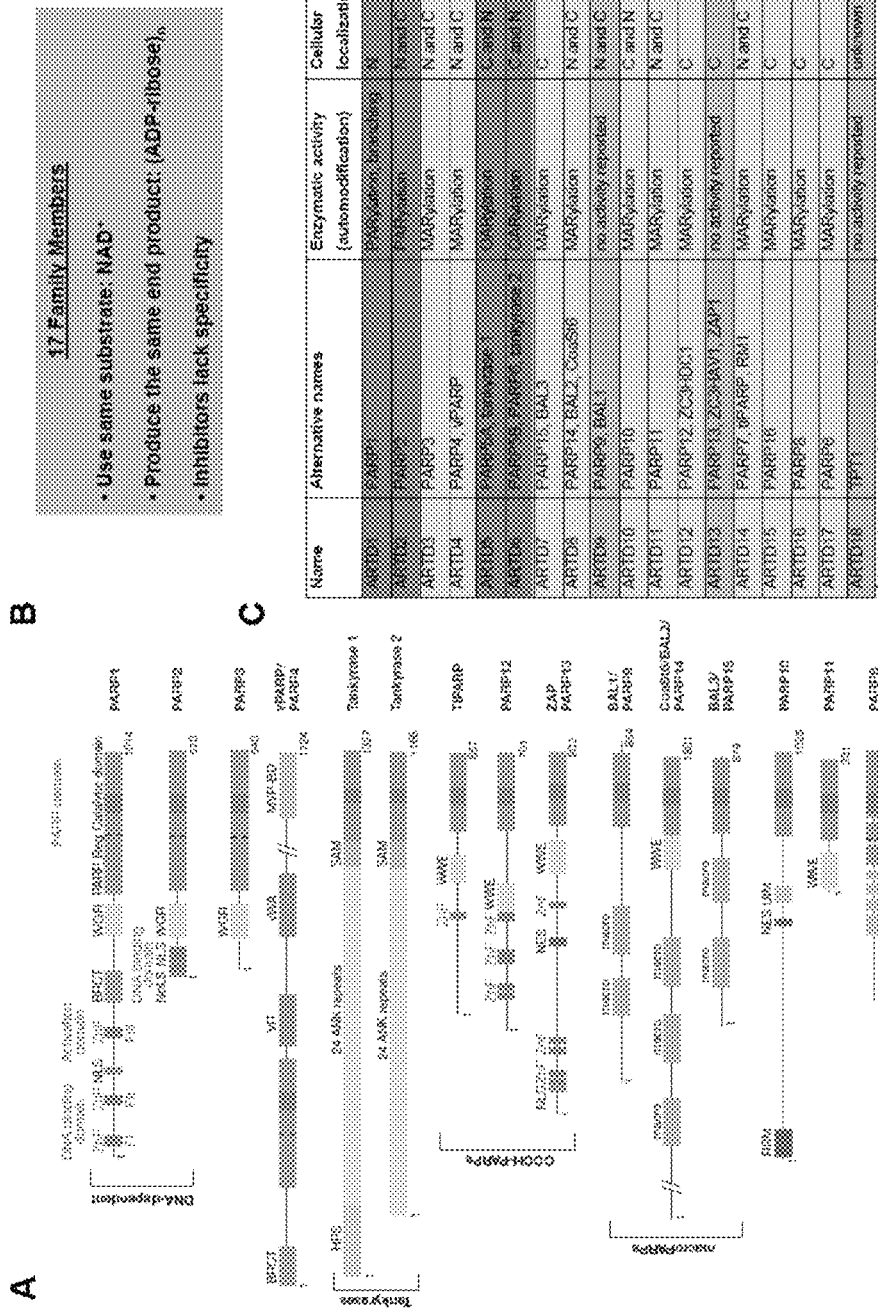
FIGS. 1A-1C—The PARP family of proteins.

The PARP family of proteins has 18 members, which are defined by a conserved PARP catalytic domain (shown in dark gray) (FIG. 1A). Determining which PARP family members are responsible for ADP-ribosylation events in a cell can be very difficult due to their overlapping substrate usage and end-product (FIG. 1B). PARPs may perform mono-ADP-ribosylation (MARylation), oligo-ADP-ribosylation (OARylation), or poly-ADP-ribosylation (PARylation) (FIG. 1C). Some PARP proteins are thought to be enzymatically inactive (PARPs 9, 13, and TPT1) (FIG. 1C).

Poly(ADP-ribosyl)ation modulates protein function by regulating either enzymatic activities or macromolecular interactions with proteins, DNA or RNA. On the other hand, PAR molecules can also regulate protein activity and function through non-covalent binding. This is illustrated by the growing list of protein-protein, protein-DNA and protein-RNA interactions that either require or are prevented by PAR. A number of modules (specific amino acid structures that form distinct structures) in proteins have been found to bind various forms of ADP-ribose. This include: (1) a somewhat conserved 20 amino-acid PAR-binding motif (PBM), which was initially established from the analysis of several DNA-repair and checkpoint proteins (Pleschke et al., 2000); (2) some macro domains, such as those found in macroH2A1.1, PARP9, or in a viral protein from the SARS coronavirus 3 (3) a $C_2H_2$ zinc-finger, known as the PBZ; and (4) the WWE domain, which have all been shown to bind to MAR or PAR in vitro (Ahel et al., 2008; Egloff et al., 2006; Karras et al., 2005). In some cases, a single protein target can bind to PAR non-covalently and also be an acceptor for poly(ADP-ribosyl)ation. These processes can involve such divergent actions as recruitment to a site where PAR is produced, and modification of the activity of the recruited protein. Whether the effect of PAR is due to steric hindrance or to electrostatic repulsion generated by the negatively-charged polymers is still unknown. Differences in the length and branching of PAR may add another level of regulation allowing different functional outcomes (Fahrer et al., 2007).

Among the other roles proposed for PAR is as a local supply of ATP molecules, important in conditions of ATP shortage. PARP1 activation in response to DNA breaks could supply the ATP necessary for ligation, the final step of single-strand break repair (SSBR). Converting PAR into ATP requires pyrophosphate, which occurs during DNA-repair synthesis (Petermann et al., 2003). AMPK, which is activated when the ATP concentration is limiting, phosphorylates PARP1, thereby enhancing its automodification (Walker et al., 2006).

A role for PAR and/or ADP-ribose as a signalling molecule is another possible role. Indeed, an essential function for PAR is during initiation of caspase-independent cell-death pathway. In addition, ADP-ribose acts as a second messenger that activates the TRPM2 channel, allowing $Ca^{2+}$ influx in response to oxidative stress. A direct involvement of PARP1/PARG in producing these ADP-ribose molecules was recently revealed (Buelow et al., 2008).

C. PARP Uses

Identifying the targets of a particular PARP protein may find use in the treatment of cancer or other hyperproliferative diseases. In some embodiments, PARP proteins act as signal modulators for cellular activity associated with the hyperproliferation of a cell. Identifying an enzymatic target for a specific PARP protein allows for the development of inhibitors which are selective for the combination of target and PARP proteins. Developing such inhibitors, in some embodiments, can tailor the effects of the inhibitors so as to reduce side effects and/or increase the efficacy of the compound. Additionally, the PARP proteins and their targets may be used to identify protein pathways and inhibitors thereof implicated in a variety of other disease states, such as stroke, myocardial infarction, and long-term neurodegenerative diseases such as Alzheimer's disease, Parkinson's disease, Huntington's disease, or amyotrophic lateral sclerosis (ALS). As such, the methods provided herein may be used to identify and optimize compounds useful in the treatment of these disease states.

Additionally, the identification of DNA sequence within a chromatin complex upregulated by a PARP protein may be used to treat cancer or another hyperproliferative disease. The transcription and translation of the DNA sequence within the chromatin complex may be upregulated by the activity of the PARP protein and thus identifying the specific PARP protein responsible may be used to develop compounds which inhibit the upregulation of these sequences. The methods described herein may be used to identify and develop methods for the prevention and treatment of cancer or hyperproliferative diseases.

II. COMPOUNDS

The compounds provided by the present disclosure are shown, for example, above in the summary of the disclosure section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent compounds of the disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

It should be recognized that the particular anion or cation forming a part of any salt form of a compound provided herein is not critical, so long as the salt, as a whole, is soluble in the desired solvent, such as water.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

III. CHEMICAL DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxylsulfonyl" means —SO$_2$OH; "aminosulfonyl" means —SO$_2$NH$_2$ and "sulfinyl" means —S(O)—.

In the context of chemical formulas, the symbol "-" means a single bond, "=" means a double bond, and "-" means triple bond. The symbol "----" represents an optional bond, which if present is either single or double. The symbol "⚌" represents a single bond or a double bond. Thus, for example, the formula

includes

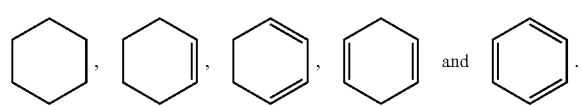

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "〰", when drawn perpendicularly across a bond (e.g.,

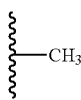

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦙⦙⦙⦙" means a single bond where the group attached to the thick end of the wedge is "into the page". The symbol "∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

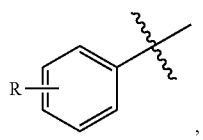

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

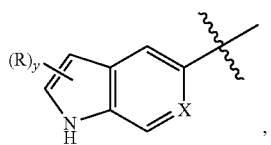

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and compound classes below, the number of carbon atoms in the group is as indicated as follows: "Cn" defines the exact number (n) of carbon atoms in the group/ class. "C≤n" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. Also compare "phosphine$_{(C≤10)}$", which designates phosphine groups having from 0 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin$_{(C5)}$", and "olefin$_{C5}$" are all synonymous. When any group or compound class below is used with the term "substituted", any carbon atoms of the chemical group replacing the hydrogen atom do not count towards the total carbon atom limit for that group or compound class.

The term "saturated" when used to modify a compound or an atom means the compound or atom has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —N$_3$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

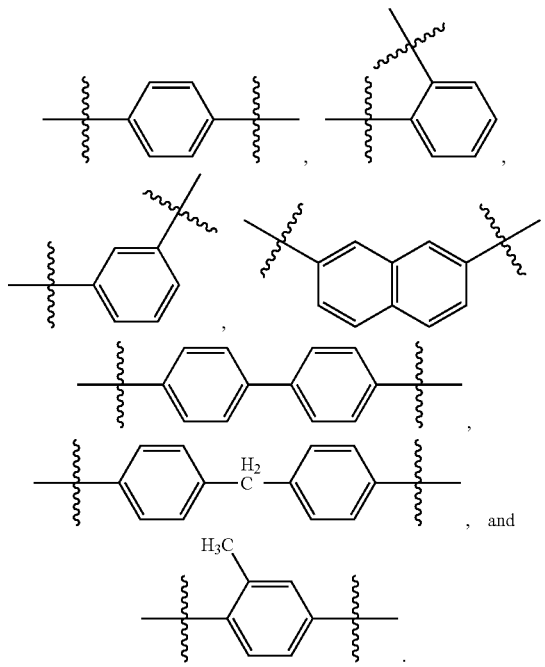

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkylamino" when used without the "substituted" modifier refers to the group —NHR, in which R is an alkyl, as that term is defined above. Non-limiting examples include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂ and —N(CH₃)(CH₂CH₃). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom attached to a carbon atom has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups —NHC(O)OCH₃ and —NHC(O)NHCH₃ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. In some aspects, the term "about" may be used to represent a difference of plus or minus 5%.

The term "adenosine moiety" represents the chemical group:

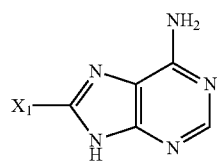

wherein X₁ is hydrogen or as defined herein. In some aspects, the adenosine moiety is attached with other chemical groups, specifically, the riboses and/or phosphate groups of the NAD analog or through the riboses and/or phosphate groups to a protein. As used throughout this application, this term "ribosylation" refers to the transfer of one or both of the ribose sugar, one or both of the phosphate groups, and the adenine moiety from the NAD analog onto a side chain of one or more amino acids of a protein.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. The term, "effective amount," when used in the context of administering to a subject or patient a compound means an amount that is sufficient to effect such induce a specific activity.

As used herein, the term "IC₅₀" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods

1. Synthesis of Selected NAD Analogs
General Reagents and Synthetic Methods.

All reagents were of analytical grade or the best grade available from commercial suppliers. Dimethyl sulfoxide (DMSO) was stored over activated molecular sieves (3 Å) for at least two weeks before use. Nucleotides were quantified and aliquoted using their extinction coefficient at $\lambda_{max}$ at pH 7. Determination of extinction coefficients was performed with a cyanide assay according to Colowick, et al., 1951, updated by Oppenheimer, 2011. 8-Br-NAD$^+$ (Abdallah et al., 1975) and 8-SH-NAD$^+$ (Kumar and Colman, 1994) were synthesized as described.

Synthesis of 8-Bu(3-yne)T-NAD$^+$.

60 µmoles of 8-SH-NAD+, triethylammonium salt, were dissolved in 1200 µL dried DMSO in a 3 mL polypropylene reaction tube with screw cap. After the addition of 468.8 µmoles (44 µL, 7.8 equivalents) 4-bromo-1-butyne and 120 µmoles (20.4 µL, 2 eq.) diisopropylethylamine, the reaction mixture was shaken under an argon atmosphere in a MHL 20 thermomixer (HLC Biotech, Bovenden, Germany), set at 25° C. and 500 rpm. After 8 hours no further reaction progress was detected by use by analytical HPLC performed with a LaChrom Elite instrument using an L-2130 pump, a L-2420 variable wavelength UV/Vis detector, a L-2350 column oven (set at 30° C.), and EZChrom software version 3.3.1 SP1 (all VWR-Hitachi, Hannover, Germany) with YMC ODS-A 12 nm, S-11 µm (YMC, Dinslaken, Germany) resin packed in a 250×4.6 mm stainless steel column. HPLC was run with a mobile phase of 25 mM sodium dihydrogen phosphate, pH 6.8, 10% acetonitrile, 4 mM tributylammonium hydrogensulfate). The reaction was quenched by addition of 1200 µL 1M sodium dihydrogen phosphate buffer, pH 4.7, and frozen at −70° C. for 1 hour. All volatile components of the reaction mixture were evaporated in a speedvac concentrator centrifuge under reduced pressure with oil pump vacuum overnight. The residue was dissolved in water (~30 mL), filtered through a filter membrane (regenerated cellulose, 0.45 µm), and purified by preparative MPLC at room temperature using a C-605 pump (Büchi, Essen, Germany), a preparative K 2001 UV-detector (Knauer, Berlin, Germany) and a L$_{200}$E analog recorder (Linseis, Selb, Germany) with Merck LiChroprep® RP-18 6 nm, 15-25 µm (Merck-Hitachi) resin packed in a 435×25 mm glass column (Kronlab, Dinslaken, Germany). The column was equilibrated with 20 mM triethylammonium formate (TEAF), pH 7. The reaction mixture was applied to the column, initially washed with the same buffer, followed by elution with 100% water. Product-containing fractions with a purity >98% (by HPLC) were changed to sodium salt via cation exchange MPLC with Toyopearl™ SP-650M, 65 m, sodium form (Tosoh Bioscience, Stuttgart, Germany) resin packed in a 125×35 mm glass column (Kronlab). All purified fractions were carefully evaporated in vacuo to yield 36.6 µmoles 8-Bu(3-yne)T-NAD$^+$ as a sodium salt.

Synthesis of 8-BuT-NAD$^+$.

Synthesis was performed in parallel reactions with 3×100 µmoles 8-Br-NAD$^+$, sodium salt. 100 µmoles of the starting material were dissolved in 1280 µL H$_2$O in a 10 mL polypropylene vial with screw cap. After addition of 2560 µL 100 mM sodium tetraborate buffer, pH 9, 1280 µL CH$_3$CN, 580 µL butyl mercaptan (5 mmol/50 eq.) and 720 µL 2.5 N NaOH (18 eq.), the reaction tube was closed tightly and placed in a thermomixer, set at 50° C. and 500 rpm. After completion of the reactions (~35 min), the solutions were placed in a 500 mL separation funnel, 200 mL water was added and the pH was rapidly titrated to pH 7 with 6 N HCl. The aqueous phase was extracted 3 times with 50 mL dichloromethane, followed by 3×30 mL ethyl acetate. Purification with preparative MPLC as above (product elution with 0.5% isopropanol) and salt change to sodium was performed as described above for 8-Bu(3-yne)T-NAD$^+$. 180.6 µmoles 8-BuT-NAD$^+$, sodium salt was obtained with a purity of 99.8% (by HPLC) (yield: 60%).

Synthesis of 8-PrT-NAD$^+$.

Synthesis and workup was performed with propyl mercaptan as described for 8-BuT-NAD$^+$ in parallel reactions with 3×100 µmoles 8-Br-NAD$^+$, sodium salt. Purification with preparative MPLC (product elution with 0.5% isopropanol), as above, with salt change to sodium performed as described above for 8-Bu(3-yne)T-NAD$^+$. 200.6 µmoles 8-PrT-NAD$^+$, sodium salt was obtained with a purity of 99.7% (by HPLC) (yield: 67%).

Synthesis of 8-Bn-NAD$^+$.

8-bromo-adenosine-5-monophosphate (25 mg, 0.059 mmol, 1.0 eq) was mixed in absolute ethanol (EtOH, 0.206 mL) while under nitrogen, followed by addition of benzylamine (0.128 mL, 1.17 mmol, 20 eq) and calcium carbonate (11.7 mg, 0.117 mmol, 2.0 eq). Reaction was heated to reflux while under nitrogen and reacted overnight. Product formation was detected by LC-MS (260 nm). The reaction was diluted with ethanol and the insoluble calcium salt was separated using centrifugation and the supernatant solvent was evaporated to obtain dry 8-benzylamine-adenosine-5-monophosphate. 8-benzylamine-adenosine-5-monophosphate was then purified by preparative HPLC and coupled to nicotinamide mononucleotide as previously described (Jiang et al., 2010) to obtain β-Nicotinamide-8-Benzylaminoadenine dinucleotide.

Synthesis of 8-Isobutyl-NAD+.

8-bromo-adenosine-5-monophosphate (25 mg, 0.059 mmol, 1.0 eq) was mixed in absolute ethanol (EtOH, 0.206 mL) under nitrogen, followed by the addition of isobutylamine (0.117 mL, 1.18 mmol, 20 eq) and calcium carbonate (11.8 mg, 0.118 mmol, 2.0 eq). The reaction was heated to reflux while under nitrogen and reacted overnight. Product formation was detected by LC-MS (260 nm). The reaction was diluted with ethanol and the insoluble calcium salt was separated using centrifugation and the supernatant solvent was evaporated to obtain dry 8-isobutylamine-adenosine-5-monophosphate. 8-isobutylamine-adenosine-5-monophosphate was then purified by preparative HPLC and coupled to nicotinamide mononucleotide as previously described (Jiang et al., 2010) to obtain β-Nicotinamide-8-isobutylaminoadenine dinucleotide.

2. Expression and Purification of Recombinant PARP Proteins

Mutagenesis of PARP cDNAs and Construction of Expression Vectors.

cDNAs encoding NAD analog-sensitive human or mouse PARP-1, PARP-2, or PARP-3 were generated by standard site-directed mutagenesis. DNA sequences were added to the cDNAs so that the expressed proteins have an affinity tag (6×His) or an epitope tag (Flag). The cDNAs were cloned plasmid (pET19b), bacmid (pFastbac), or lentiviral (pTY-U6) vectors for expression of the cognate proteins in bacteria (*E. coli*), Sf9 insect cells, mammalian cells, respectively.

Purification of PARP-1 Protein Expressed in *E. coli* Cells.

pET19b plasmids encoding PARP-1 or PARP-1 site-specific mutants for analog-sensitivity and gatekeeper residue screen were individually transformed into $CaCl_2$-based chemically-competent *E. coli* strain BL21(DE3) cells using a heat shock approach and these cells were inoculated into 5 mL of Luria Broth supplemented with 100 μg/mL of ampicillin for growth overnight with shaking at 37° C. After overnight growth, separate 1 L cultures of LB supplemented with 100 μg/mL ampicillin were inoculated with 5 mL individual cultures and incubated at 37° C. with shaking until reaching an ocular density of 0.4 OD per milliliter at a wavelength of 595 nm. These cultures were then induced for protein overexpression by addition of Isopropyl β-D-1 thiogalactopyranoside (IPTG) at a final concentration of 1 mM. Cells were grown for 2 hours at 37° C. post-induction followed by harvesting via centrifugation. Harvested bacterial cell pellets were flash frozen in liquid nitrogen and stored at −80° C.

Induced frozen bacterial cell pellets from 1 L of culture were thawed on wet ice until liquid and lysed by sonication for 2 minutes total at 70% amplitude with a Branson S-450 Digital Sonifier in IMAC Lysis Buffer (10 mM Tris.HCl, pH 7.5, 0.5 M NaCl, 0.1 mM EDTA, 0.1% NP-40, 10% Glycerol, 10 mM Imidazole, 1 mM PMSF, 1 mM β-Mercaptoethanol). Lysate was clarified by centrifugation at 15,000 RPM for 30 minutes at 4° C. in an SS34 Rotor. The clarified supernatant was applied to 1 mL bed volume of Ni-NTA Resin (QIAGEN) equilibrated in IMAC Equilibration Buffer (10 mM Tris.HCl, pH 7.5, 0.5 M NaCl, 0.1% NP-40, 10% Glycerol, 10 mM Imidazole) and incubated at 4° C. for 2 hours on a nutator. Ni-NTA agarose beads were washed 4 times in 30 mL of IMAC Wash Buffer (10 mM Tris.HCl, pH 7.5, 1 M NaCl, 0.2% NP-40, 10% Glycerol, 10 mM Imidazole, 1 mM PMSF) with collection by centrifugation. His-tagged proteins were eluted by 3 consecutive washes of IMAC elution buffer (10 mM Tris.HCl, pH 7.5, 0.2 M NaCl, 0.1% NP-40, 10% Glycerol, 500 mM Imidazole, 1 mM PMSF, 1 mM (3-Mercaptoethanol). Eluates were combined and dialyzed overnight in IMAC Dialysis Buffer (10 mM Tris.HCl, pH 7.5, 0.2 M NaCl, 10% Glycerol, 1 mM PMSF, 1 mM (3-Mercaptoethanol). Dialysate containing PARP-1 was collected, spun at maximum speed in a microcentrifuge to remove any debris, and quantified using a Bradford Protein Assay. Final Dialysate concentration was increased to 1 mg/mL using a 3,000 Dalton molecular weight cut-off centrifugal concentrator (Millipore) as needed and proteins were flash frozen in single-use aliquots with liquid $N_2$, and stored at −80° C.

Purification of PARP-1, PARP-2, and PARP-3 Proteins Expressed in Sf9 Insect Cells.

Uninfected serum free Sf9 cells, cultured in SF-II 900 media (Invitrogen) were plated onto 10 cm diameter cell culture plates at a density of $1 \times 10^6$ cells per milliliter of culture. Cells were transfected with 1 μg of bacmid encoding for expression of PARP-1, PARP-$1_{L877A}$, PARP-2, PARP-$2_{L443A}$, PARP-3 or PARP-$3_{L394A}$ using Cellfectin transfection reagent as described by manufacturer (Invitrogen). After 5 hours filter sterilized FBS, Penicillin, and Streptomycin were added to a final concentration of 10%, 100 I.U. per milliliter, and 100 micrograms per milliliter respectively. After three days cell medium containing the desired baculovires was collected. Following two more rounds of infection and collection, a 150 mL culture of Sf9 cells in SF-II 900 media supplemented with 10% FBS in a sterile spinner flask were infected with baculovirus-containing medium for PARP overexpression. Two days after infection, Sf9 cells with PARP proteins expressed were collected by centrifugation, washed once with cold PBS, pelleted into a 50 mL plastic tube, flash frozen with liquid $N_2$, and stored at −80° C. for future use.

PARP-1-, PARP2- or PARP3-expressed frozen Sf9 cell pellet from 150 mL of cell culture was thawed on wet ice. Cells were resuspended in 7 mL of FLAG PARP Lysis Buffer (20 mM HEPES, pH 7.9, 0.5 M NaCl, 4 mM $MgCl_2$, 0.4 mM EDTA, 20% Glycerol, 250 mM Nicotinamide, 2 mM β-mercaptoethanol, 2× protease inhibitor cocktail (Roche)) and dounced 10 times on ice with tight pestle with a dounce homogenizer (Wheaton). Lysate was centrifuged 30 minutes at 15,000 RPM at 4° C. in an SS34 Rotor (Sorvall). Clarified supernatant was removed, mixed with an equal volume of FLAG Dilution Buffer (20 mM HEPES, pH 7.9, 10% Glycerol, 0.02% NP-40), and sonicated with a Branson S-450 Digital Sonifier for 15 seconds at 65% amplitude in a salt ice bath. Lysate was centrifuged once again for 30 minutes at 15,000 RPM at 4° C. in an SS34 Rotor. Clarified lysate was applied to 200 microliters of anti-FLAG M2 agarose resin equilibrated in a 50:50 mix of FLAG PARP Lysis Buffer and FLAG Dilution Buffer without β-mercaptoethanol and incubated at 4° C. for 3 hours on a nutator. Resin was washed twice with 100 volumes of FLAG PARP Wash Buffer #1 (20 mM HEPES, pH 7.9, 150 mM NaCl, 2 mM $MgCl_2$, 0.2 mM EDTA, 15% Glycerol, 0.01% NP-40, 100 mM Nicotinamide, 0.2 mM β-Mercaptoethanol, 1 mM PMSF, 1 μM Aprotinin, 100 μM Leupeptin), twice with FLAG PARP Wash Buffer #2 (20 mM HEPES, pH 7.9, 1 M NaCl, 2 mM $MgCl_2$, 0.2 mM EDTA, 15% Glycerol, 0.01% NP-40, 100 mM Nicotinamide, 0.2 mM β-Mercaptoethanol, 1 mM PMSF, 1 μM Aprotinin, 10 μM Leupeptin), and twice with FLAG PARP Wash Buffer #3 (20 mM HEPES, pH 7.9, 150 mM NaCl, 2 mM $MgCl_2$, 0.2 mM EDTA, 15% Glycerol, 0.01% NP-40, 0.2 mM β-Mercaptoethanol, 1 mM PMSF). PARP proteins were eluted from the M2 Agarose resin by 3 washes with FLAG PARP Wash Buffer #3 with 0.2 mg/mL FLAG peptide (SIGMA). Eluted proteins (~0.5 mg/mL) were distributed in 12 μL aliquots, flash frozen with liquid $N_2$, and stored at −80° C. until use.

Expression of PARP-1 in Mouse Embryo Fibroblast (MEF) Cells.

Lentiviral particles were generated essentially as previously described (Liang et al., 2012). Briefly, 293T cells were co-transfected with transducing plasmids encoding proteins for packaging (Δ8.9) and envelope proteins (VSVG) along with pTY-U6 plasmids containing GFP, mouse PARP-1, or mouse PARP-$1_{L877A}$ sequences. Media was replaced after 24 hours and the 24-72 hour post-transfection medium was collected containing lentivirus. Virus-containing medium was spun 3,000 RCF for 10 minutes at room temperature, the supernatant filtered through a 0.22 μm filter, and incubated for 24 hours on Parp1$^{-/-}$ MEF cells. Virus-containing medium above Parp1$^{-/-}$ cells was removed after 24 hours and replaced with fresh medium. 48 hours post-infection, 2 μg/mL Puromycin was added to select for cells stably expressing GFP, PARP-1, or PARP-1$_{L877A}$. Following complete selection of cells expressing GFP, PARP-1, or PARP-1$_{L877A}$ cells were grown in 1 μg/mL Puromycin, and expression of transduced construct was confirmed via western blotting.

3. In Vitro Assays Automodification Assays with Recombinant PARP Proteins

In vitro automodification reactions. 200 ng PARP Protein was incubated in Automodification Buffer (30 mM HEPES, pH 8.0, 5 mM MgCl$_2$, 5 mM CaCl$_2$, 0.01% NP-40, 1 mM DTT, 100 ng/mL sonicated salmon sperm DNA (Stratagene), 100 ng/mL BSA (SIGMA)) with NAD$^+$ or NAD$^+$ analogs as indicated at 25° C. for 5 (PARP-1 and PARP2) or 30 minutes (PARP3) for Sf9-purified proteins and for 45 minutes for bacterially purified enzymes.

Western Blot Detection and Quantification.

Reactions were stopped by addition of ⅓ reaction volume with 4×SDS-PAGE Loading Buffer (200 mM Tris, pH 6.8, 8% SDS, 40% Glycerol, 4% β-mercaptoethanol, 50 mM EDTA, 0.08% Bromophenol Blue) followed by boiling at 100° C. for 5 minutes. Reaction products in 1×SDS-PAGE buffer were then resolved on a 10% SDS-PAGE gel, transferred to a nitrocellulose membrane and blotted with a polyclonal antibody against PARP-1 or with an antibody-like detection reagent against ADP-ribose (MABE1016, Millipore). Relative quantitation of PARP-1 automodifications was performed by the ratio of PARylation-induced increase in SDS-PAGE mobility relative to un-shifted full length PARP-1 measured by densitometry of anti-PARP-1 western blots.

Detection of Automodification by in-Gel Fluorescence.

Reactions were stopped by methanol:chloroform precipitation (Wessel and Flugge, 1984). The protein pellets were clicked to azido-Rhodamine (Click Chemistry Tools) in Denaturing CC Buffer (100 mM HEPES, pH 8, 4 M Urea, 0.5 M NaCl, 2% CHAPS, 10 μM azido-Rhodamine, 1 mM THPTA (Click Chemistry Tools), 5 mM CuSO$_4$, 5 mM Sodium Ascorbate) with Azido-Rhodamine, THPTA:CuSO$_4$ complex, and Sodium Ascorbate each added sequentially in written order. After 2 hours in dark at room temperature, clicked proteins were isolated by a methanol:chloroform precipitation and resuspended in 1×SDS Loading Buffer (50 mM Tris, pH 6.8, 2% SDS, 10% Glycerol, 1% β-mercaptoethanol, 12.5 mM EDTA, 0.02% Bromophenol Blue) and boiled at 100° C. for 5 minutes in the dark. Clicked proteins in 1×SDS-PAGE buffer were then resolved on a 10% SDS-PAGE gel. The gel was then washed quickly with MilliQ H$_2$O, washed twice with 10% methanol, washed twice with MilliQ H$_2$O and visualized on a Bio-Rad Pharos FX Plus Molecular Imager (excitation: 532 nm, emission: 605 nm).

4. In Vitro ADP-Ribosylation Assays with Recombinant PARP Proteins and Cell Extracts HeLa cell nuclear extract preparation. HeLa Nuclear Extract was prepared essentially as described in Dignam et al., 1983. 5 L of HeLa S3 cells were grown in Spinner flasks to a density of 0.5×10$^6$ cells per milliliter and harvested by centrifugation at 4° C. for 10 minutes at 2000 RPM. Cell pellets were washed in 5 pelleted cell volumes of ice cold PBS and centrifuged 10 minutes at 2000 RPM. Cells were resuspended in 5 pelleted cell volumes of Buffer A (10 mM HEPES, pH 7.9, 1.5 mM MgCl$_2$, 10 mM KCl, 0.5 mM DTT, 1 mM PMSF, 4 mM Benzamidine, 1 μM Aprotinin, 100 μM Leupeptin, 1 μM Pepstatin A) and incubated 10 minutes on ice to facilitate cell swelling and centrifuged at 4° C. for 10 minutes at 2000 RPM. Cells were resuspended in 2 pelleted cell volumes of Buffer A and dounced with a light pestle dounce homogenizer (Wheaton) to release nuclei. The nuclei were then pelleted by centrifugation at 4° C. for 10 minutes at 2000 RPM and the supernatant decanted. The nuclei were subsequently centrifuged at 4° C. for 20 minutes at 25,000 RCF to obtain a crude nuclear fraction. Nuclei were then resuspended in 7.5 mL of Buffer C (20 mM HEPES, pH 7.9, 25% Glycerol, 0.42 M NaCl, 1.5 mM MgCl$_2$, 0.2 mM EDTA, 1 mM PMSF, 4 mM Benzamidine, 1 μM Aprotinin, 100 μM Leupeptin, 1 μM Pepstatin A) by pipetting and with a loose pestle dounce homogenizer and stirred for 30 minutes at 4° C. slowly in a 25 mL glass Erlenmeyer flask with a magnetic stir bar. The resulting suspension was centrifuged at 4° C. for 30 minutes at 25,000 RCF. The supernatant containing the nuclear extraction was dialyzed against Buffer D (20 mM HEPES, pH 7.9, 20% Glycerol, 0.1M KCl, 0.2 mM EDTA, 0.5 mM PMSF, 0.5 mM DTT) and centrifuged at 4° C. for 20 minutes at 25,000 RCF to remove any precipitated material. The supernatant above any precipitated protein pellet was designated as "HeLa Nuclear Extract" and aliquoted in single use tubes, flash frozen in liquid N$_2$, and stored at −80° C. until further use.

ADP-Ribosylation of HeLa Cell Nuclear Extract.

1 μg of PARP protein was incubated for 5 minutes in Automodification Buffer (30 mM HEPES, pH 8.0, 5 mM MgCl$_2$, 5 mM CaCl$_2$, 0.01% NP-40, 1 mM DTT, 100 ng/mL sonicated salmon sperm DNA (Stratagene), 100 ng/mL BSA (SIGMA)), 5 minutes upon addition of 50 micrograms of HeLa nuclear extract, and 15 minutes with 250 μM NAD$^+$ or 250 μM 8-Bu(3-yne)T-NAD$^+$. Reactions were stopped by methanol:chloroform precipitation. The protein pellets were clicked to azido-Rhodamine (Click Chemistry Tools) in Denaturing CC Buffer (100 mM HEPES, pH 8, 4 M Urea, 0.5 M NaCl, 2% CHAPS, 100 μM azido-Rhodamine, 1 mM THPTA (Click Chemistry Tools), 5 mM CuSO$_4$, 5 mM Sodium Ascorbate) with Azido-Rhodamine, THPTA:CuSO$_4$ complex, and Sodium Ascorbate each added sequentially in written order. After 2 hours in dark at room temperature, clicked proteins were isolated by a methanol:chloroform precipitation and resuspended in 1×SDS Loading Buffer (50 mM Tris, pH 6.8, 2% SDS, 10% Glycerol, 1% β-mercaptoethanol, 12.5 mM EDTA, 0.02% Bromophenol Blue) and boiled at 100° C. for 5 minutes in the dark. Clicked proteins in 1×SDS-PAGE buffer were then resolved on a 10% SDS-PAGE gel. The gel was then washed quickly with MilliQ H$_2$O, washed twice with 10% methanol, washed twice with MilliQ H$_2$O and visualized on a Bio-Rad Pharos FX Plus Molecular Imager (excitation: 532 nm, emission: 605 nm).

5. LC-MS/MS Analysis of 8-Bu(3-Yne)T-ADP-Ribosylated Proteins

Preparation of Analog-ADP-Ribosylated Samples.

Twenty μg of analog-sensitive PARP protein was incubated for 5 minutes in Automodification Buffer (30 mM HEPES, pH 8.0, 5 mM MgCl$_2$, 5 mM CaCl$_2$, 0.01% NP-40, 1 mM DTT, 100 ng/mL sonicated salmon sperm DNA (Stratagene), 100 ng/mL BSA (SIGMA)), 5 minutes upon addition of 1000 μg of HeLa nuclear extract, and 15 minutes with 250 μM 8-Bu(3-yne)T-NAD$^+$. Reactions were stopped by methanol:chloroform precipitation (Wessel and Flugge, 1984). The protein pellets were resuspended in 1 mL of Urea Lysis Buffer (200 mM HEPES, pH 8, 8 M Urea, 1 M NaCl, 4% CHAPS) and insoluble proteins were pelleted by centrifugation for 1 minute at max speed in a microcentrifuge. Soluble proteins in Urea Lysis Buffer were combined in a 2 mL tube with 100 μL Azido-Agarose Beads (Click Chemistry Tools), 820 μL MilliQ $H_2O$, 40 μL of a 50 mM THPTA:250 mM $CuSO_4$ pre-formed catalytic complex, 20 μL 500 mM aminoguanidine hydrochloride, 20 μL 500 mM Sodium Ascorbate, with, THPTA:$CuSO_4$ sequentially in written order. After 18 hours of reaction time in the dark with slow mixing in a rotisserie-style mixer, beads were centrifuged at room temperature for 1 minute at 1000 RCF. Reaction supernatant was aspirated and beads were resuspended in 1.8 mL MilliQ $H_2O$ and centrifuged at room temperature for 1 minute at 1000 RCF. Beads were then resuspended in 1 mL SDS Wash Buffer (100 mM Tris.HCl, pH 8.0, 1% SDS, 250 mM NaCl, 5 mM EDTA) supplemented with freshly made 1 mM DTT and heated to 70° C. for 15 minutes and then allowed to cool to room temperature. Resin was pelleted by centrifugation at room temperature for 5 minutes at 1000 RCF and supernatant aspirated. Resin was reusupended in 1 mL of SDS Wash Buffer with 40 mM iodoacetamide at room temperature for 30 minutes in the dark to alkylate cysteine residues. Resin was then transferred to a 2 mL single use column (Bio-Rad) and 10 washes of 2 mL each with SDS Wash Buffer, followed by 10 washes of 2 mL each with Urea Wash Buffer (100 mM Tris, pH 8, 8 M Urea), followed by 10 washes of 2 mL each with 20% acetonitrile were performed.

Following extensive washes, resin was resuspended in 500 μL Trypsin Digestion Buffer (100 mM Tris, pH 8, 2 mM $CaCl_2$, 10% acetonitrile). Trypsin digestion was performed by addition of 1 μg trypsin (Promega) and incubation at room temperature overnight with slow mixing on a rotisserie-style mixer. The tryptic peptide digest was prepared for LC-MS/MS by desalting on a C18 stage tip (Thermo) according to the manufacturers protocol and lyophilized for storage at −20° C. prior to LC-MS/MS run. Post-tryptic digest resin, containing peptides still ligated through 8-Bu (3-yne)T-ADP-ribosylation site were transferred to fresh 2 mL single use column (Bio-Rad) and 10 washes of 2 mL each with SDS Wash Buffer, followed by 10 washes of 2 mL each with Urea Wash Buffer (100 mM Tris, pH 8, 8M Urea), followed by 10 washes of 2 mL each with 20% acetonitrile, followed by 5 washes of Peptide Elution Buffer (100 mM HEPES, pH 8.5). Resin was transferred to microcentrifuge tube and hydroxylamine (Sigma) was added at 0.5 M to elute aspartate- and glutamate-modified 8-Bu(3-yne)T-ADP-ribosylated peptides from resin, a modification of the LC-MS/MS approach previously reported in (Zhang et al., 2013). Eluted peptides were prepared for LC-MS/MS by desalting on a C18 stage tip (Thermo) according to the manufacturers protocol and lyophilized for storage at −20° C. prior to LC-MS/MS run. Samples were prepared for LC-MS/MS and analyzed exactly as described in (Zhang et al., 2013).

Analysis of LC-MS/MS Data.

ADP-ribosylation sites were obtained from initial LC-MS/MS analysis as outlined in (Zhang et al., 2013). All ADP-ribosylation sites identified from both replicates generated were used in proteomic data analysis.

Gene Ontology Analyses.

Gene ontology analyses were performed using the DAVID (Database for Annotation, Visualization, and Integrated Discovery) tool (Huang et al., 2007a; Huang et al., 2007b).

ADP-Ribosylation Relative to Other Post-Translational Modifications.

ADP-ribosylation sites were mapped from IPI accession numbers to Uniprot IDs giving preference to polypeptides matching gene name to IPI database nomenclature, followed by polypeptides with the longest amino acid sequence length. A knowledge base of known post-translational modifications (PTMs) for comparison against ADP-ribosylation sites identified in this study were obtained from the PhosphoSite Plus database (Hornbeck et al., 2012), with additional content for Sumoylation (Hendriks et al., 2014) and ADP-ribosylation (Zhang et al., 2013) which were downloaded and processed from the relevant publications' material. ADP-ribosylation sites identified in this study, as well as an aspartate/glutamate ratio-normalized random control, were analyzed for their amino acid-to-amino acid relationship to other PTMs within the above-mentioned knowledge base. On any given polypeptide, the PTM with the closest spatial relationship to an ADP-ribosylation site identified in this study, or within the random aspartate or glutamate control were retained for analysis and visualization.

ADP-Ribosylation Site Motifs.

Sequence±8 amino acids from all unique ADP-ribosylation sites for PARP-1, PARP-2, and PARP-3 were analyzed for statistically significant enrichment of specific amino acid sequences using the Motif-X server (Chou and Schwartz, 2011; Schwartz and Gygi, 2005), with a significance threshold of 0.005.

6. Click-ChIP-Seq of Chromatin-Associated ADP-Ribosylated Nuclear Proteins

In Nuclei 8-Bu(3-Yne)T-ADP-Ribosylation Reactions.

50% confluent MEF cells expressing asPARP-1 were harvested with cold PBS using a rubber policeman and collected by centrifugation for 5 minutes at 800 RCF at 4° C. Cells were resuspended for 10 minutes to facilitate cell swelling in Nuclear Isolation Buffer (10 mM HEPES, pH 8.0, 2 mM $MgCl_2$, 3 mM $CaCl_2$, 300 mM Sucrose, 1 mM DTT, 1 mM PMSF, 4 mM Benzamidine, 1 μM Aprotinin, 100 μM Leupeptin, 1 μM Pepstatin A, and 1 in 250 parts SIGMA Phosphatase Inhibitor Cocktails 2 and 3). Nuclei were released from cells by addition of NP-40 to 0.65% under medium vortex and immediately collected by centrifugation at 10,000 RCF for 1 minute at 4° C. Nuclei were resuspended at a concentration of 4-6 million nuclei per mL in PARP Reaction Buffer (30 mM Tris-C1, pH 7.5, 10 mM KCl, 5 mM $MgCl_2$, 5 mM $CaCl_2$, 0.01% NP-40, 0.05 mM EDTA, 20% Glycerol, 1 mM DTT, 1 mM PMSF, 4 mM Benzamidine, 1 μM Aprotinin, 100 μM Leupeptin, 1 μM Pepstatin A, and 1 in 250 parts SIGMA Phosphatase Inhibitor Cocktails 2 and 3). 8-Bu(3-yne)T-$NAD^+$ was then added at 250 μM final concentration for 30 minutes at 25° C. with occasional gentle mixing by flicking to allow in nuclei ADP-ribosylation to occur. Nuclei were spun 1 minute at 2000 RCF and resuspended to homogeneity in Nuclei Crosslinking Buffer (10 mM HEPES, pH 8, 10 mM NaCl, 10 mM $MgCl_2$, 0.1% NP-40, 1 mM PMSF, 4 mM Benzamidine, 1 μM Aprotinin, 100 μM Leupeptin, 1 μM Pepstatin A). Nuclei were then crosslinked by the addition of 0.5% methanol-free formaldehyde (Pierce) for 10 minutes while rotating slowly on a rotisserie-style mixer. Crosslinking was then quenched by addition of 275 mM Glycine and placed on ice for 10 minutes. Nuclei were pelleted at 500 RCF for 10 minutes before 8-Bu(3-yne)T-ADP-ribosylated proteins were clicked to either a fluorophore or biotin for subsequent experimentation.

Click Reactions and Purification of 8-Bu(3-Yne)T-ADP-Ribose-Associated Regions of the Genome.

Following in nuclei 8-Bu(3-yne)T-ADP-ribosylation, as outlined above, nuclei were washed three times with 1 mL of Nuclei Clicking Buffer (10 mM HEPES, pH 8, 10 mM NaCl, 10 mM Spermidine, 0.1% NP-40, 1 mM PMSF, 4 mM Benzamidine, 1 µM Aprotinin, 100 µM Leupeptin, 1 µM Pepstatin A) with centrifugation at room temperature for 10 minutes at 500 RCF. Nuclei were then twice resuspended in 1 mL of Nuclei Clicking Buffer and 8-Bu(3-yne)T-ADP-ribosylated proteins clicked to biotin by sequential addition of 100 µM azido-Biotin (Click Chemistry Tools), 1 mM: 5 mM pre-formed complex of THPTA:CuSO4, and 5 mM Sodium Ascorbate. Nuclei were again washed three times with 1 mL of Nuclei Clicking Buffer with centrifugation at room temperature for 10 minutes at 500 RCF to remove unclicked azido-biotin. Nuclei were then resuspended in 1 mL of ChIP Lysis Buffer (50 mM Tris.HCl, pH 7.9, 1% SDS, 10 mM EDTA, 1× Protease Inhibitor (Roche)) and sonicated in a water bath sonicator (diagenode) with a DNA fragment distribution of 200-500 bp. Nuclei were then diluted ten times in ChIP Dilution Buffer (20 mM Tris.HCl, pH 7.9, 2 mM EDTA, 150 mM NaCl, 0.5% Triton X-100, 1 mM DTT, 1×protease inhibitor (Roche), 1% BSA). Biotinylated chromatin was then bound to MyOne T1 Streptaividin-conjugated magnetic beads (Invitrogen) overnight at 4° C. on a nutator. Beads were then separated on a magnetic stand and washed twice with 2% SDS, once with Low Salt Immune Complex Wash Buffer (20 mM Tris.HCl), pH 8.1, 2 mM EDTA, 125 mM NaCl, 0.05% SDS, 1% Triton X-100, 1 µM Aprotinin, and 100 µM Leupeptin), three times with High Salt Immune Complex Wash Buffer (20 mM Tris.HCl, pH 8.1, 2 mM EDTA, 500 mM NaCl, 0.05% SDS, 1% Triton X-100, 1 µM Aprotinin, and 100 µM Leupeptin), once with LiCl Wash Buffer (10 mM Tris.HCl, pH 8.1, 1 mM EDTA, 250 mM LiCl, 1% NP-40, 1% sodium deoxycholate, 1 µM Aprotinin, and 100 µM Leupeptin), and twice with 1× TE (10 mM Tris.HCl, 1 mM EDTA).

Magnetically separated resin was then resuspended in 200 µL of De-crosslinking Buffer (100 mM Sodium Bicarbonate, 1% SDS, 100 mM NaCl) and 8-Bu(3-yne)T-ADP-ribose-associated DNA was released from beads through removing formaldehyde-induced crosslinks overnight by incubation overnight at 65° C. Beads were magnetically separated from solute and supernatant containing eluted DNA was moved into a fresh tube and labeled "eluate". Beads were resuspended in 200 µL 1×TE, separated from solute on a magnetic stand, and the supernatant was added to above-mentioned eluate. Eluate was subjected to 1 hour RNase treatment at 37° C. by RNase (Roche), followed by 1 hour protease treatment at 55° C. with 20 µg of Proteinase K, and subsequently nucleic acids were purified by Phenol:Chloroform:Isoamyl Alcohol extraction (25:24:1). DNA was ethanol precipitated, washed with 70% ethanol, dried, and resuspended in a working volume. For qPCR, this purified DNA was directly compared by quantitative PCR with a Roche LightCycler 480 (Hah et al., 2011) to a retained input fraction (de-crosslinked and purified as above).

Click-Seq Library Preparation.

Streptavidin isolated, eluted, and purified DNA described above, corresponding to 8-Bu(3-yne)T-ADP-ribose-associated sequences were prepared for high throughput sequencing as previously described (Luo et al., 2014). Briefly, 50 ng of DNA was blunted and 5' phosphorylated, a single adenine base was then added using klenow (5' exo-), and adapters ligated to adenine base overhang using T4 DNA Ligase. All enzymes were obtained from Enzymatics, reactions carried out according to manufacturer's protocol, and DNA purified by MinElute Reaction Cleanup Kit (QIAGEN) between each enzymatic reaction. Adapter-ligated DNA was then run on a 2% low-melt agarose (Roche) gel containing 1×Sybr Gold stain, size selected, and purified using a QIAquick Gel Extraction Kit (QIAGEN). DNA was further purified by Phenol:Chloroform:Isoamyl Alcohol extraction (25:24:1), ethanol precipitated, washed with 70% ethanol, dried, and resuspended in a working volume. DNA was amplified by 14 PCR cycles using Phusion DNA polymerase (QIAGEN) and purified with Agencourt Ampure XP beads (Beckman Coulter). DNA was analyzed for size distribution and adapter-dimer contamination using a BioAnalyzer (Agilent) and quantified with a Qubit 2.0 Fluorometer (Invitrogen) prior to high throughput sequencing using an Illumina Hi-seq 2000.

Quality Control.

Quality control for the ChIP- and Click-seq data was performed using the FastQC tool (www.bioinformatics.babraham.ac.uk/projects/fastqc/).

ChIP-Seq Alignment and Visualization.

The ChIP-seq libraries were aligned to the human genome (hg19) using default parameters in BOWTIE (Langmead et al., 2009). Click-seq libraries were prepared for visualization by calculating the odds ratio of click-seq relative to input in 2500 bp windows with 250 bp shifts. Click-seq odds ratios were then converted into bigwig files and visualized in the IGV genome browser (Robinson et al., 2011; Thorvaldsdottir et al., 2013) with a 2-fold cutoff for grey/orange intensity. For H3K4me3 and NELF, uniquely mappable read densities were converted into bigWig files using BEDTools (Quinlan and Hall, 2010), and visualization in the IGV genome browser.

Peak Calling and Genome-Wide Dataset Correlations.

Genome-wide transcription factor binding sites were calculated using SICER (Zang et al., 2009) with a false discovery rate of $1\times10^{-2}$ for all data sets evaluated. Genome-wide binding patterns or histone modification sites for NELF, SA1, SA2, SMC1, SMC3, CTCF, CDK9, and H3K4me3 using SICER was determined with both a window and gap size of 200 bp. Genome-wide binding patterns or histone modification sites for PARP-1, H3K36me3, H3K27me3, and H3K9me3 using SICER was determined with a window size of 200 bp and a gap size of 600 bp. Lamin binding patterns were determined by SICER using a window size of 1000 bp and a gap size of 3000 bp. To determine the correlation of PARP-1 dependent ADP-ribosylation genome-wide to a transcription factor or histone post-translational modification, a Pearson's correlation coefficient was calculated between the normalized read depth for each factor underneath their requisite peaks and input-normalized click-seq levels.

Heatmaps.

The read densities calculated surrounding 10 kb (±5 kb) of the refseq TSS with a custom scripting approach and visualized as heatmaps using Java TreeView (Saldanha, 2004). For GRO-seq heatmaps, sense and anti-sense reads were calculated on adjacent lines for each refseq promoter and colored red and blue, respectively.

Published Datasets Used for Reference.

The following publically available deep sequencing data sets along with their requisite controls were downloaded from GEO Archive using the accession numbers listed here: H3K36me3 ChIP-seq from GSE12241; LaminB1-DamID from GSE17051; NELFb ChIP-seq from GSE24113; SA1, SA2, SMC1, and SMC3 ChIP-seq from GSE32319; CTCF and H3K4me3 ChIP-seq from GSE29218; H3K9me3 and H3K27me3 from GSE22268; CDK9 ChIP-seq from GSE45517.

Antibodies.

The custom rabbit polyclonal antiserum against PARP-1 used for Western blotting and ChIP assays was generated by using an antigen comprising the amino-terminal half of PARP-1 (Kim et al., 2004)(now available from Active Motif; cat. no. 39559). The custom recombinant antibody-like anti-poly-ADP-ribose binding reagent (anti-PAR) and anti-pan-ADP-ribose binding reagent (anti-panADPR) were generated and purified in-house (now available from EMD Millipore; cat. nos. MABE1031 and MABE1016, respectively). Additional antibodies were purchased from commercial sources: M2 anti-FLAG monoclonal (Sigma; F1804), NELF-E (Santa Cruz; H-140), NELF-A (Bethyl; A301), and Pol II (Santa Cruz; N-20). For Western blotting, the primary antibodies were used at a 1:4000 dilution in 5% non-fat milk made in TBST, with subsequent detection using an appropriate HRP-conjugated secondary antibody (Pierce) used at a 1:5000 dilution in 5% non-fat milk made in TBST.

Alignment of $NAD^+$ into the Active Site of the PARP-1 Catalytic Domain.

PDB files from co-crystal structures of Diptheria toxin with $NAD^+$ (PDBID: 1TOX), Tankyrase 2 with EB-47 (PDBID:4BJ9), and PARP-1 with 3-methoxybenzamide (PDBID:3PAX) were downloaded from the RCSB Protein Data Bank for analysis. Using matchmaker in the UCSF Chimera program, the structures of Diptheria toxin, Tankyrase 2, and PARP-1 were aligned to one another. Subsequently, an estimate of $NAD^+$ binding within the PARP-1 active site was obtained in two steps: First, by aligning the nicotinamide-ribose portion of $NAD^+$ from 1TOX with the nicotinamide-based inhibitor, 3-MB. Second, by positioning the adenine-ribose portion of $NAD^+$ according to the atomic coordinates of adenine-ribose from the $NAD+$-like inhibitor EB-47 from 4BJ9.

$NAD^+$ Analogs.

The $NAD^+$ analogs used herein were either purchased from, or synthesized collaboratively with, the BIOLOG Life Science Institute (LSI), Bremen, Germany. The following $NAD^+$ analogs used for initial screening were purchased from the BIOLOG LSI catalog: (1) β-nicotinamide-8-methylaminoadenine dinucleotide (8-MA-NAD+), (2) β-nicotinamide-8-dimethylaminoadenine dinucleotide (8-DMA-$NAD^+$), (3) β-nicotinamide-8-ethylthioadenine dinucleotide (8-ET-$NAD^+$), (4) β-nicotinamide-8-propylthioadenine dinucleotide (8-PrT-$NAD^+$), (5) β-nicotinamide-8-butylthioadenine dinucleotide (8-BuT-$NAD^+$), (6) β-nicotinamide-8-cyclopentylthioadenine dinucleotide (8-cPeT-$NAD^+$), (7) β-nicotinamide-8-piperidinoadenine dinucleotide (8-PIP-$NAD^+$), (8) β-nicotinamide-8-phenylthioaminoadenine dinucleotide (8-PT-$NAD^+$), and (9) β-Nicotinamide-8-(4-chlorophenylthio)adenine dinucleotide (8-pCPT-$NAD^+$).

Synthesis of $NAD^+$ Analogs. General Reagents and Synthetic Methods.

All reagents were analytical grade or the best grade available from commercial suppliers. Dimethyl sulfoxide (DMSO) was stored over activated molecular sieves (3 Å) for at least two weeks before use. Nucleotides were quantified and aliquoted using their extinction coefficient at $\lambda_{max}$ at pH 7.0. Extinction coefficients were determined using a cyanide assay as described (Colowick et al., 1951), with modifications. 8-Br-$NAD^+$ and 8-SH-$NAD^+$ (Kumar and Colman, 1994) were synthesized as described and provided by BIOLOG LSI.

Synthesis of 8-Bu(3-Yne)T-$NAD^+$.

Sixty μmoles of 8-SH-$NAD^+$, triethylammonium salt, were dissolved in 1200 μL of dried DMSO in a 3 mL polypropylene reaction tube with a screw cap. After addition of 468.8 μmoles (44 μL, 7.8 equivalents) of 4-bromo-1-butyne and 120 μmoles (20.4 μL, 2 eq.) of diisopropylethylamine, the reaction mixture was shaken under argon atmosphere in a MHL 20 thermomixer (HLC Biotech), set at 25° C. and 500 rpm. After 8 hours, no further reaction progress was detected by analytical HPLC performed with a LaChrom Elite instrument using an L-2130 pump, a L-2420 variable wavelength UV/Vis detector, a L-2350 column oven (set at 30° C.), and EZChrom software version 3.3.1 SP1 (all VWR-Hitachi) with YMC ODS-A 12 nm, S-11 μm (YMC) resin packed in a 250×4.6 mm stainless steel column. HPLC was run with a mobile phase of 25 mM sodium dihydrogen phosphate, pH 6.8, 10% acetonitrile, and 4 mM tributylammonium hydrogensulfate. The reaction was quenched by the addition of 1,200 μL 1 M sodium dihydrogen phosphate buffer, pH 4.7, and frozen at −70° C. for 1 hour. All volatile components of the reaction mixture were evaporated overnight in a SpeedVac concentrator under reduced pressure with oil pump vacuum. The residue was dissolved in ~30 mL water, passed through a 0.45 μm regenerated cellulose filter, and purified by preparative MPLC at room temperature using a C-605 pump (Büchi), a preparative K 2001 UV-detector (Knauer), and a L200E analog recorder (Linseis) with Merck LiChroprep RP-18 6 nm, 15-25 μm (Merck-Hitachi) resin packed in a 435×25 mm glass column (Kronlab) equilibrated with 20 mM triethylammonium formate (TEAF), pH 7.0. The reaction mixture was applied to the column, washed with the same buffer, and then eluted with 100% water. The product-containing fractions with a purity of >98% (by HPLC) were exchanged to sodium salt via cation exchange MPLC with Toyopearl SP-650M, 65 m, sodium form (Tosoh Bioscience) resin packed in a 125×35 mm glass column (Kronlab). All purified fractions were carefully evaporated under vacuum to yield 36.6 μmoles 8-Bu(3-yne)T-$NAD^+$, sodium salt.

Synthesis of 8-BuT-$NAD^+$.

Synthesis was performed in parallel reactions with 3×100 μmoles 8-Br-$NAD^+$, sodium salt. One hundred moles of the starting material were dissolved in 1,280 μL of $H_2O$ in a 10 mL polypropylene vial with a screw cap. After addition of 2,560 μL of 100 mM sodium tetraborate buffer, pH 9.0, 1,280 μL $CH_3CN$, 580 μL butyl mercaptan (5 mmol, 50 eq.) and 720 μL of 2.5 N NaOH (18 eq.), the reaction tube was closed tightly and placed in a thermomixer, set at 50° C. and 500 rpm. After completion of the reactions (~35 min), the solutions were transferred to a 500 mL separation funnel, 200 mL of water were added, and the pH was rapidly titrated to pH 7.0 with 6 N HCl. The aqueous phase was extracted 3 times with 50 mL dichloromethane, followed by 3×30 mL ethyl acetate. Purification with preparative MPLC (product elution with 0.5% isopropanol) and salt exchange to sodium were performed as described above for 8-Bu(3-yne)T-$NAD^+$. The final product was 180.6 μmoles of 8-BuT-$NAD^+$, sodium salt with a purity of 99.8% (by HPLC) and a yield of 60%.

Synthesis of 8-PrT-$NAD^+$.

Synthesis and workup was performed with propyl mercaptan as described for 8-BuT-$NAD^+$ in parallel reactions with 3×100 μmoles of 8-Br-$NAD^+$, sodium salt. Purification with preparative MPLC (product elution with 0.5% isopropanol) and salt exchange to sodium were performed as described above for 8-Bu(3-yne)T-$NAD^+$. The final product was 200.6 μmoles of 8-PrT-$NAD^+$, sodium salt with as purity of 99.7% (by HPLC) and a yield of 67%.

Synthesis of 8-BnA-$NAD^+$.

Fifty-nine moles of 8-bromo-adenosine-5-monophosphate were mixed in 206 μL of absolute ethanol while under nitrogen, followed by the addition of 117 μL benzylamine (20 eq) and 11.8 mg of calcium carbonate (2.0 eq). The reaction was heated to reflux under nitrogen and carried out overnight. Product formation was detected by LC-MS at 260 nm. The reaction was diluted with ethanol and the insoluble calcium salt was separated by centrifugation. The supernatant was evaporated to obtain dry 8-benzylamine-adenosine-5-monophosphate, which was then purified by preparative HPLC and coupled to nicotinamide mononucleotide as previously described (9) to obtain β-nicotinamide-8-benzylaminoadenine dinucleotide.

Synthesis of 8-iBuA-NAD$^+$.

Fifty-nine moles of 8-bromo-adenosine-5-monophosphate was mixed in 206 μL of absolute ethanol while under nitrogen, followed by the addition of 117 μL isobutylamine (20 eq) and 11.8 mg of calcium carbonate (2.0 eq). The reaction was heated to reflux while under nitrogen and carried out overnight. Product formation was detected by LC-MS at 260 nm. The reaction was diluted with ethanol and the insoluble calcium salt was separated by centrifugation. The supernatant was evaporated to obtain dry 8-isobutylamine-adenosine-5-monophosphate, which was then purified by preparative HPLC and coupled to nicotinamide mononucleotide as previously described (9) to obtain β-nicotinamide-8-isobutylaminoadenine dinucleotide.

Molecular Biology and Cloning. Human and Mouse cDNAs.

cDNA pools from 293T cells (human) or 3T3-L1 cells (mouse) were prepared by extraction of total RNA from the cells using Trizol (Life Technologies), followed by reverse transcription using superscript III reverse transcriptase (Promega) and an oligo(dT) primer according to manufacturer's instructions.

Construction of Bacterial Expression Vectors.

The following expression vectors were constructed for expression of PARP-1 and NELF-E in bacteria.

PARP-1:

Human PARP-1 cDNA in pET19b (Novagen), described previously (6), was subjected to PCR-based site-directed mutagenesis at codons corresponding to amino acid residues 864, 865, 868, 869, 872, 877, 878, 879, 895, and 897 to alter the coding to either glycine or alanine.

NELF-E:

Human NELF-E cDNA was isolated by PCR from the cDNA pools described above and cloned into the pGEX2T bacterial expression vector (GE Life Sciences), allowing expression of GST-tagged NELF-E. An ADP-ribosylation site point mutant human NELF-E cDNA was generated by mutating codons for glutamate at amino acid positions 121, 151, 152, 171, 172, and 374 to codons for glutamine (the mutant includes two glutamate residues adjacent to two the four identified, for a total of six sites). The mutant cDNA was amplified by PCR and cloned into pGEX2T for expression of GST-tagged NELF-E with mutated PARP-1 ADP-ribosylation sites.

Construction of Insect Expression Vectors.

Human PARP-2, mouse PARP-1, and mouse PARP-3 cDNAs were isolated by PCR from the cDNA pools described above, adding sequences encoding an N-terminal FLAG epitope to the cDNAs via the primers during amplification. Leucine to alanine-encoding base pair alterations at "gatekeeper" positions were introduced into the cDNAs using PCR-based site-directed mutagenesis. All constructs were sequenced ensure fidelity of the sequences. Recombinant bacmids were then prepared for Sf9 transfection via transformation into the DH10BAC E. coli strain with subsequent blue/white colony screening using the Bac-to-Bac system (Invitrogen) according to the manufacturer's instructions.

Construction of Mammalian Expression Vectors.

The following expression vectors were constructed for expression of PARP-1, NELF subunits, and GFP in mammalian cells.

PARP-1:
PCR products for mouse PARP-1 and PARP-1 (L877A) were amplified from their cognate cDNAs, adding a sequence encoding an N-terminal FLAG epitope during the amplification process. The PCR products were then cloned into the pTY-U6 plasmid (provided by Yi Zhang, UT Southwestern Medical Center) after removal of an ORF encoding GFP-3×FLAG cDNA NELF Subunits:
Constructs for the expression of NELF subunits were generated using two different mammalian expression vectors: (1) pCDNA3—A cDNA encoding an N-terminal HA epitope-tagged NELF-A protein followed by an IRES2 sequence was amplified using two-step PCR from 293T cDNA and the pIRES2dsRED plasmid (Clontech), respectively, and ligated into a cloning vector. A cDNA encoding N-terminal FLAG epitope-tagged NELF-E was amplified from cDNA and cloned into the NELFA-IRES2 plasmid described above. The resulting HA-NELF-A-IRES2-FLAG-NELF-E construct was then sub-cloned into pCDNA3. (2) pINDUCER—A cDNA encoding wild-type NELF-E or ADP-ribosylation site point mutant NELF-E with an N-terminal FLAG tag was amplified by PCR and cloned into the pINDUCER plasmid (Addgene).

GFP:
Constructs for the expression of GFP were generated using two different mammalian expression vectors: (1) pCDNA3—A cDNA encoding GFP with a C-terminal 3×FLAG epitope tag was sub-cloned from pTY-U6-GFP-3×FLAG into pCDNA3; (2) pINDUCER—A cDNA encoding GFP was amplified by PCR and cloned into the pINDUCER plasmid.

Expression and Purification of Recombinant Proteins. Purification of PARP-1 Expressed in E. coli.

BL21(DE3) E. coli, transformed with a pET19b plasmid encoding wild-type PARP-1 or mutant PARP1, were grown in LB with ampicillin at 37° C. to a density (OD$_{600\ nm}$) of 0.4. Recombinant protein expression was then induced by addition of IPTG to 1 mM for 2 hours at 37° C. The cells were collected by centrifugation, and the bacterial cell pellets were flash frozen in liquid N$_2$ and stored at −80° C.

The cell pellets were thawed on wet ice and lysed by sonication in IMAC Lysis Buffer (10 mM Tris.HCl, pH 7.5, 0.5 M NaCl, 0.1 mM EDTA, 0.1% NP-40, 10% glycerol, 10 mM imidazole, 1 mM PMSF, 1 mM β-mercaptoethanol). The lysates were clarified by centrifugation. Recombinant PARP-1 was purified from the clarified lysate using Ni-NTA affinity chromatography, with washing of the resin using IMAC Wash Buffer (10 mM Tris.HCl, pH 7.5, 1 M NaCl, 0.2% NP-40, 10% glycerol, 10 mM imidazole, 1 mM PMSF) and elution of the PARP-1 protein using IMAC Elution Buffer (10 mM Tris.HCl, pH 7.5, 0.2 M NaCl, 0.1% NP-40, 10% glycerol, 500 mM imidazole, 1 mM PMSF, 1 mM β-mercaptoethanol). The eluates were dialyzed in IMAC Dialysis Buffer (10 mM Tris.HCl, pH 7.5, 0.2 M NaCl, 10% glycerol, 1 mM PMSF, 1 mM β-mercaptoethanol) and concentrated as needed with a centrifugal concentrator. The purified PARP-1 protein was flash frozen in liquid $N_2$ in single-use aliquots, at a final concentration of 1 mg/mL and stored at −80° C.

Purification of PARPs Expressed in Sf9 Insect Cells.

Sf9 insect cells, cultured in SF-II 900 medium (Invitrogen), were transfected with 1 µg of bacmid driving expression of wild-type PARP-1, PARP-1(L877A), wild-type PARP-2, PARP-2(L443A), wild-type PARP-3, or PARP-3 (L394A) using Cellfectin transfection reagent as described by manufacturer (Invitrogen). After three days, the medium was supplemented with 10% FBS, penicillin and streptomycin, and collected as a baculovirus stock. After multiple rounds of amplification of the stock, the resulting high titer baculovirus was used to infect fresh Sf9 cells to induce expression of PARP protein for two days. The PARP-expressing Sf9 cells were then collected by centrifugation, flash frozen in liquid $N_2$, and stored at −80° C.

PARP-1-, PARP-2- or PARP-3-containing Sf9 cell pellets were thawed on wet ice. The cells were resuspended in FLAG Lysis Buffer [20 mM HEPES, pH 7.9, 0.5 M NaCl, 4 mM $MgCl_2$, 0.4 mM EDTA, 20% glycerol, 250 mM nicotinamide, 2 mM β-mercaptoethanol, 2× protease inhibitor cocktail (Roche)] and lysed by Dounce homogenization (Wheaton). The lysate was clarified by centrifugation, mixed with an equal volume of FLAG Dilution Buffer (20 mM HEPES, pH 7.9, 10% glycerol, 0.02% NP-40), sonicated, and then clarified by centrifugation again. The clarified lysate was mixed with anti-FLAG M2 agarose resin (Sigma), washed twice with FLAG Wash Buffer #1 (20 mM HEPES, pH 7.9, 150 mM NaCl, 2 mM $MgCl_2$, 0.2 mM EDTA, 15% glycerol, 0.01% NP-40, 100 mM nicotinamide, 0.2 mM β-mercaptoethanol, 1 mM PMSF, 1 µM aprotinin, 100 µM leupeptin), twice with FLAG Wash Buffer #2 (20 mM HEPES, pH 7.9, 1 M NaCl, 2 mM $MgCl_2$, 0.2 mM EDTA, 15% glycerol, 0.01% NP-40, 100 mM nicotinamide, 0.2 mM β-mercaptoethanol, 1 mM PMSF, 1 µM aprotinin, 100 µM leupeptin), and twice with FLAG Wash Buffer #3 (20 mM HEPES, pH 7.9, 150 mM NaCl, 2 mM $MgCl_2$, 0.2 mM EDTA, 15% glycerol, 0.01% NP-40, 0.2 mM β-mercaptoethanol, 1 mM PMSF). The FLAG-tagged PARP proteins were eluted from the anti-FLAG M2 agarose resin with FLAG Wash Buffer #3 containing with 0.2 mg/mL FLAG peptide (Sigma). The eluted proteins (~0.5 mg/mL) were distributed into single use aliquots, flash frozen in liquid $N_2$, and stored at −80° C. until use.

Purification of NELF-E Expressed in E. coli.

BL21(DE3) Rosetta2 µLysS E. coli, transformed with a pGEX2T plasmid encoding GST-tagged wild-type or ADP-ribosylation site point mutant NELF-E, were grown in LB with ampicillin and chloramphenicol at 37° C. to a density ($OD_{600\ nm}$) of 0.4. The growth temperature was lowered to 18° C. and the expression of the recombinant protein was induced at a density ($OD_{600\ nm}$) of 0.7 by the addition of IPTG to 0.5 mM for 18 hours at 18° C. The cells were collected by centrifugation, and the bacterial cell pellets were flash frozen in liquid $N_2$ and stored at −80° C.

The cell pellets were thawed on wet ice and lysed by sonication in GST Purification Buffer (50 mM Tris.HCl, pH 7.5, 0.15 M NaCl, 1 mM EDTA, 0.1% NP-40, 1 mM PMSF, 5 mM β-mercaptoethanol). The lysates were clarified by centrifugation. Recombinant GST-NELF-E was purified from the clarified lysate using glutathione-agarose (Sigma) affinity chromatography, with washing of the resin using GST Purification Buffer and elution of the purified proteins in GST Purification Buffer supplemented with 15 mg/mL reduced glutathione. The eluates were dialyzed in GST Purification Buffer and flash frozen in liquid $N_2$ in single-use aliquots and stored at −80° C.

Purification of NELF Proteins Expressed in Mammalian Cells.

pCDNA3-based plasmid encoding a bicistronic expression cassette for N-terminal HA epitope-tagged NELF-A and N-terminal FLAG epitope-tagged NELF-E were transfected into 293T cells using GeneJuice transfection reagent (Novagen). Seventy-two hours post-transfection and two hours after vehicle (DMSO), 300 nM Flavopiridol (Sigma), or 20 µM Olaparib (ApexBio) treatment, the cells were collected in ice cold PBS and pelleted by centrifugation. The cells were then resuspended in ice cold Nuclei Isolation Buffer (10 mM HEPES, pH 8.0, 2 mM $MgCl_2$, 3 mM $CaCl_2$, 300 mM sucrose) with freshly added protease inhibitors and 250 nM APD-HPD (Millipore) and allowed to swell for 10 minutes on ice. The nuclei were released from the cells by the addition of NP-40 to 0.65% v/v with vortexing (medium speed) and immediately collected by centrifugation. The supernatant was removed and proteins were extracted from the nuclei by resuspension on ice for 30 minutes in Immunoprecipitation Buffer (25 mM Tris.HCl, pH 7.5, 150 mM NaCl, 1% NP-40, 1 mM EDTA) with freshly added protease inhibitors and 250 nM APD-HPD. The resulting nuclear extract was clarified by two rounds of centrifugation and incubated with equilibrated anti-FLAG M2 agarose resin for 2.5 hours at 4° C. with gentle mixing. The agarose beads were washed thoroughly with IP Wash Buffer (25 mM Tris.HCl, pH 7.5, 250 mM NaCl, 1% NP-40, 1 mM EDTA) with freshly added protease inhibitors and 250 nM APD-HPD and then equilibrated in IP Extraction Buffer (25 mM Tris.HCl, pH 7.5, 25 mM NaCl, 0.1% NP-40, 1 mM EDTA) with freshly added protease inhibitors and 250 nM APD-HPD. The immunoprecipitated NELF complex was eluted from the agarose resin by addition of Imunoprecipitation Buffer containing 0.2 mg/mL FLAG peptide. The eluted proteins were distributed in single use aliquots, flash frozen in liquid $N_2$, and stored at −80° C. until use.

Cell Culture and Generation of Knockdown and Overexpression Cell Lines.

MCF-7, HeLa S3, 3T3-L1, and 293T cell lines were obtained from the ATCC and used for extract preparation, cDNA library generation, and the variety of assays described herein. Wild-type and $Parp1^{-/-}$ mouse embryonic fibroblasts (MEF) cells were a gift from Zhao-Qi Wang, Leibniz Institute for Age Research. MCF-7 cells were maintained in Minimum Essential Medium Eagle supplemented with 5% calf serum. Prior to all experiments, MCF-7 cells were grown for 3 days in phenol red-free MEM Eagle medium supplemented with 5% charcoal-dextran-treated calf serum. MEF, HeLa S3, and 293T cells were cultured in DMEM supplemented with 10% fetal bovine serum, penicillin, and streptomycin.

shRNA-Mediated Knockdown in MCF-7 Cells.

Retroviruses were generated by transfection of pSUPER-.retro vectors, each expressing a different shRNA sequence directed against the cognate target, with an expression vector for the VSV-G envelope protein into Phoenix Ampho cells using the GeneJuice transfection reagent (Novagen) according to the manufacturer's protocol. The resulting viruses were collected, filtered, and used to infect the parental MCF-7 cell line. Stably transduced cells were isolated under appropriate drug selection with 0.5 µg/mL puromycin or 800 µg/mL G418, expanded, and frozen in aliquots for future use.

Ectopic Protein Expression in MEFs, MCF-7 Cells, and 293T Cells.

Lentiviral particles were generated essentially as previously described (10).

MEFs:

Parp1$^{-/-}$ MEFs were infected with lentivirus, with subsequent selection using 1 µg/mL puromycin to enrich for cells expressing GFP, wild-type PARP-1, or PARP-1(L877A). Ectopic expression of the cognate proteins was confirmed by Western blotting.

MCF-7 Cells:

MCF-7 cells were infected with lentivirus, with subsequent selection using 1 mg/mL Geneticin (Life Technologies) to enrich for cells with doxycycline-inducible expression of GFP, NELF-E, or ADP-ribosylation site point mutant NELF-E.

293T Cells:

pCDNA$_3$-based plasmids encoding GFP with a c-terminal 3×FLAG epitope tag or a bicistronic expression cassette for N-terminal HA epitope-tagged NELF-A and N-terminal FLAG epitope-tagged NELF-E were transfected into 293T cells using GeneJuice transfection reagent (Novagen).

PARP-1 Enzyme Kinetics Assays.

The enzyme kinetics of wild-type and analog-sensitive mutants of human PARP-1 were determined essentially as previously described (Jiang et al., 2010). Purified PARP-1 proteins were incubated for 5 minutes in PARP Enzyme Kinetics Buffer (50 mM Tris.HCl, pH 7.9, 4 mM MgCl$_2$) containing 0.5 mg/mL sonicated salmon sperm DNA (Stratagene) at 25° C. with 10, 20, 30, 50, 100, 250, and 500 µM NAD$^+$ or 8-Bu(3-yne)T-NAD$^+$. The concentrations of the purified PARP-1 proteins were (1) 25 nM for PARP-1 with NAD$^+$, (2) 50 nM for PARP-1(L877A) with NAD$^+$, and (Carter-O'Connell et al., 2014) 250 nM for PARP-1 and PARP-1(L877A) with 8-bu(3-yne)T-NAD$^+$. The reactions were brought to 450 mM perchloric acid (HClO$_4$) to stop them, incubated for 5 minutes on ice, and then brought to 26.5 mM potassium carbonate (K$_2$CO$_3$) to quench them. The quenched reactions were centrifuged at maximum speed in a microcentrifuge at 4° C., and the supernatant containing small molecules from the automodification reaction was collected.

The supernatants from the extracted ADP-ribosylation reactions were analyzed using a Shimadzu LCMS-QP8000α with a Phenomenex Kinetex C18 column (150×4.6 mm, 5 µm XB-C18 100A) monitored at 260 nm. The solvents were 50 mM ammonium acetate pH 5.4 (solvent A) and 50% methanol in water (solvent B). The compounds were eluted at a flow rate of 0.3 mL per minute with 0% solvent B for 1 minute, a linear gradient of 0% to 1% solvent B over 5 minutes, a linear gradient of 1% to 50% solvent B for 5 minutes, an equilibration in 50% solvent B for 1 minute, and finishing with an equilibration back to 0% solvent B for 2 minutes. The retention times for ADP-ribose, NAD$^+$, nicotinamide, 8-Bu(3-yne)T-ADP-ribose, and 8-Bu(3-yne)T-NAD$^+$ were 12.7, 16.6, 18.9, 20.6, and 22.0 minutes, respectively. Quantitative values for the small molecules and metabolites were obtained by comparison to a standard curve. The k$_{cat}$ and K$_m$ values were obtained by curve-fitting the V/[E]-[S] plot using KaleidaGraph. ADP-ribosylation activity was derived using the formation of nicotinamide after subtraction of the signals for ADP-ribose or 8-Bu(3-yne)T-ADP-ribose.

In Vitro PARP Automodification Reactions. Automodification Reactions.

Two hundred nanograms of purified recombinant PARP protein (PARP-1, 2, or 3) were incubated in Automodification Buffer [30 mM HEPES, pH 8.0, 5 mM MgCl$_2$, 5 mM CaCl$_2$, 0.01% NP-40, 1 mM DTT, 100 ng/µL sonicated salmon sperm DNA (Stratagene), 100 ng/µL BSA (Sigma)] with 25 µM NAD$^+$ or NAD$^+$ analog at 25° C. for 5 min. for PARP-1 and PARP-2 purified from Sf9 cells, 30 min. for PARP-3 purified from Sf9 cells, or 45 min. for PARP-1 purified from E. coli.

Detection of Automodification by Western Blotting.

The automodification reactions were stopped by the addition of one third of a reaction volume of 4×SDS-PAGE Loading Buffer (200 mM Tris.HCl, pH 6.8, 8% SDS, 40% glycerol, 4% 3-mercaptoethanol, 50 mM EDTA, 0.08% bromophenol blue) followed by heating to 100° C. for 5 min. The reaction products were then resolved on a 10% PAGE-SDS gel, transferred to a nitrocellulose membrane, and blotted with a polyclonal antibody against PARP-1 or an ADP-ribose detection reagent (MABE1016, EMD Millipore). Relative quantification of PARP-1 automodification was performed using densitometry and was expressed as the ratio of the PARylation-induced decrease in PARP-1 mobility relative to non-shifted PARP-1.

Detection of Automodification by in-Gel Fluorescence.

The automodification reactions were stopped by methanol:chloroform precipitation (Wessel and Flugge, 1984), with subsequent collection of the precipitates by centrifugation. The protein pellets were redissolved clicked to azido-rhodamine (Click Chemistry Tools) in Denaturing CC Buffer [100 mM HEPES, pH 8.0, 4 M urea, 0.5 M NaCl, 2% CHAPS, 100 µM azido-rhodamine, 5 mM THPTA (Click Chemistry Tools), 1 mM CuSO$_4$, 5 mM sodium ascorbate] following the step-wise addition of azido-rhodamine, THP-TA:CuSO$_4$ complex, and sodium ascorbate. After a 2 hour reaction in the dark at room temperature, the clicked proteins were collected by a methanol:chloroform precipitation with centrifugation, redissolved in 1×SDS Loading Buffer (50 mM Tris.HCl, pH 6.8, 2% SDS, 10% glycerol, 1% β-mercaptoethanol, 12.5 mM EDTA, 0.02% bromophenol blue), and heated at 100° C. for 5 min. in the dark. The clicked proteins were resolved on a 10% PAGE-SDS gel. The gel was then washed quickly with MilliQ H$_2$O, washed twice with 10% methanol, washed twice with water, and visualized on a Bio-Rad Pharos FX Plus Molecular Imager (excitation: 532 nm, emission: 605 nm).

In Vitro NELF-E ADP-Ribosylation Reactions.

One hundred nM of recombinant PARP-1 protein purified from Sf9 insect cells was (1) incubated in Automodification Buffer, followed by (2) the addition of 1 µM GST, GST-NELF-E, or GST-NELF-E mutant, and (3) the addition of 25 µM NAD$^+$ at 25° C. for 20 min. Detection of ADP-ribosylated GST-tagged NELF-E was performed as described above for the automodification of PARP-1 using ADP-ribose detection reagent (MABE1016; EMD Millipore).

NELF-E/TAR RNA Binding Assays. TAR RNA Folding and End-Labeling.

HIV TAR RNA was ordered from Integrated DNA Technologies (Coralville, Iowa) and resuspended in DEPC-treated 1×TE to a concentration of 100 µM. TAR RNA was folded at a concentration of 10 µM in RNA Folding Buffer (10 mM Tris.HCl, pH 7.5, 100 mM KCl, 10 mM MgCl$_2$) by incubation for 2 minutes at 90° C., followed by rapid cooling on wet ice for 2 minutes, and incubation at room temperature for 30 minutes to equilibrate. The RNA was end-labeled at a concentration of 1 µM in T4 PNK Buffer (70 mM Tris.HCl, pH 7.5, 10 mM MgCl$_2$, 5 mM DTT) using T4 PNK (NEB) and 835 nM γ-$^{32}$P-ATP (3000 Ci/mmol; Perkin-Elmer) for 1 hour at room temperature. TAR RNA was then desalted into 10 mM Tris.HCl, pH 7.5, using an RNase free Micro Bio-Spin P-30 Gel Column (Bio-Rad) according to the manufacturer's instructions prior to use in electrophoretic mobility shift assays.

NELF-E ADP-Ribosylation and Electrophoretic Mobility Shift Assay.

One µM of GST or GST-NELF-E was incubated with or without 100 nM PARP-1 in Gel Shift Buffer (20 mM Tris.HCl, pH 7.5, 37.5 mM NaCl, 0.025% NP-40, 5 mM $MgCl_2$, 5 mM $CaCl_2$, 0.1 mg/mL BSA, 0.1 mg/ml sonicated salmon sperm DNA, 5% Glycerol, 20 nM end-labeled TAR RNA). Then 25 or 100 µM of $NAD^+$ was added to stimulate NELF-E ADP-ribosylation. The reaction was stopped after incubation for 20 minutes at room temperature by the addition of 100 µM Olaparib (Apex Bio). Half of each reaction was then diluted 10-fold in Gel Shift Buffer, followed by a 1 hour incubation at room temperature to equilibrate. The samples were run on 5% polyacrylamide gels in 0.5×TBE for 2 hours at 4° C. The gels were dried and exposed to autoradiographic film overnight.

Preparation and LC-MS/MS Analysis of 8-Bu(3-Yne)T-ADP-Ribosylated HeLa Cell Nuclear Extract Proteins.

The following protocols were used for small-scale and large-scale labeling, with subsequent in-gel fluorescence or mass spectrometry analyses, respectively.

Small-Scale Modification of HeLa Cell Nuclear Extract Proteins and Detection by in-Gel Fluorescence.

HeLa cell nuclear extract was prepared as previously described (Dignam et al., 1983). One microgram of PARP protein (PARP-1, 2, or 3; wild-type or analog sensitive) was incubated in separate reactions as follows: (1) 5 min. in Automodification Buffer, (2) 5 min. with 50 g of HeLa cell nuclear extract, followed by 15 min. with 250 µM $NAD^+$, or (3) 5 min. with 50 µg of HeLa cell nuclear extract, followed by 15 min. with 250 µM 8-Bu(3-yne)T-$NAD^+$. The reactions were stopped by methanol:chloroform precipitation and the precipitates were collected by centrifugation. The protein pellets were clicked to azido-rhodamine (Click Chemistry Tools) in Denaturing CC Buffer, run on an SDS-PAGE gel, and visualized using a Bio-Rad Pharos FX Plus Molecular Imager, as described above.

Large-Scale 8-Bu(3-Yne)T-ADP-Ribosylation of HeLa Cell Nuclear Extract Proteins and LC-MS/MS.

Twenty µg of asPARP protein were incubated sequentially as follows: (1) 5 minutes in Automodification Buffer, (2) 5 minutes upon addition of 1000 µg of HeLa nuclear extract, and then (3) 15 minutes with 250 M 8-Bu(3-yne)T-$NAD^+$. The reactions were stopped by methanol:chloroform precipitation. The protein pellets were resuspended in 1 mL of Urea Solubilization Buffer (200 mM HEPES, pH 8.0, 8 M urea, 1 M NaCl, 4% CHAPS) and the insoluble proteins were pelleted by centrifugation for 1 minute at maximum speed in a microcentrifuge. Soluble proteins in Urea Solubilization Buffer were combined sequentially in a 2 mL tube in the following order with mixing: 100 µL azido-agarose Beads (Click Chemistry Tools), 820 µL water, 40 µL of a 50:250 mM $CuSO_4$:THPTA pre-formed catalytic complex, 20 µL of 500 mM aminoguanidine hydrochloride, and 20 µL of 500 mM sodium ascorbate. After 18 hours of reaction time in the dark with slow mixing in a rotating mixer, the beads were collected by centrifugation at room temperature for 1 minute at 1000 RCF in a microcentrifuge and the reaction supernatant was aspirated. The beads were resuspended in 1.8 mL MilliQ $H_2O$ and were collected by centrifugation at room temperature for 1 minute at 1000 RCF. The beads were then resuspended in 1 mL of SDS Wash Buffer (100 mM Tris.HCl, pH 8.0, 1% SDS, 250 mM NaCl, 5 mM EDTA) supplemented with freshly made 1 mM DTT, heated to 70° C. for 15 minutes, and then allowed to cool to room temperature. The resin was collected by centrifugation at room temperature for 5 minutes at 1000 RCF in a microcentrifuge and the supernatant was aspirated. The resin was then resuspended in 1 mL of SDS Wash Buffer containing 40 mM iodoacetamide and incubated at room temperature for 30 minutes in the dark to alkylate the cysteine residues. The resin was then transferred to a 2 mL single use column (Bio-Rad) and washed as follows: 10 washes of 2 mL each with SDS Wash Buffer, 10 washes of 2 mL each with Urea Wash Buffer (100 mM Tris.HCl, pH 8.0, 8M urea), and 10 washes of 2 mL each with 20% acetonitrile. Following these extensive washes, the resin was resuspended in 500 µL of Trypsin Digestion Buffer (100 mM Tris.HCl, pH 8.0, 2 mM $CaCl_2$, 10% acetonitrile).

Trypsin digestion of bead-bound 8-Bu(3-yne)T-ADP-ribosylated HeLa cell nuclear extract proteins was performed by adding of 1 µg of trypsin (Promega) to the Trypsin Digestion Buffer, with incubation at room temperature overnight with slow mixing on a rotating mixer. The peptides from the tryptic digest were prepared for LC-MS/MS by desalting on a C18 stage tip (Thermo) according to the manufacturer's protocol and lyophilized for storage at −20° C. prior to the LC-MS/MS runs for peptide ID. Post-tryptic digest resin, containing peptides covalently linked to the agarose resin through the azide-clicked 8-Bu(3-yne)T-ADP-ribosylation site, were transferred to a fresh 2 mL single use column (Bio-Rad) and washed as follows: 10 washes of 2 mL each with SDS Wash Buffer, 10 washes of 2 mL each with Urea Wash Buffer, 10 washes of 2 mL each with 20% acetonitrile, and 5 washes of 2 mL each with Peptide Elution Buffer (100 mM HEPES, pH 8.5). The resin was transferred to a microcentrifuge tube and hydroxylamine (Sigma) was added to 0.5 M to elute the glutamate- and aspartate-modified 8-Bu(3-yne)T-ADP-ribosylated peptides from the resin, using a modification of an approach previously described (Zhang et al., 2013). The eluted peptides were prepared for LC-MS/MS by desalting on a C18 stage tip (Thermo) according to the manufacturer's protocol and then lyophilized for storage at −20° C. prior to LC-MS/MS analysis. Samples were prepared for LC-MS/MS exactly as described previously (Zhang et al., 2013).

Analysis of LC-MS/MS Data. LC-MS/MS Peptide and Site Identification.

The sites of ADP-ribosylation were obtained from LC-MS/MS analysis as described previously (Zhang et al., 2013). All ADP-ribosylation sites identified from both replicates were used in the data analysis. The software, scripts, and other information about the analyses can be obtained by contacting the corresponding author (W.L.K.).

Gene Ontology Analyses.

Gene ontology analyses were performed using the DAVID (Database for Annotation, Visualization, and Integrated Discovery) tool (Huang et al., 2007a and Huang et al., 2007b). The input was the PARP target proteins found to be ADP-ribosylated in the LC-MS/MS analysis.

Location of Sites of ADP-Ribosylation Relative to Other Post-Translational Modifications.

ADP-ribosylation sites were mapped from IPI accession numbers to Uniprot IDs giving preference to polypeptides matching gene names to IPI database nomenclature, followed by polypeptides with the longest amino acid sequence length. A knowledge base of known post-translational modifications (PTMs) for comparison versus the ADP-ribosylation sites identified in this study was obtained from the PhosphoSite Plus database (Hornbeck et al., 2012). Additional content for sumoylation (Hendriks et al., 2014) and ADP-ribosylation (Zhang et al., 2013), which was downloaded and processed from the publically available data, was added. The sites of ADP-ribosylation sites identified in this study, as well as an aspartate/glutamate ratio-normalized random control, were analyzed for amino acid-to-amino acid relationships to other PTMs within the assembled PTM knowledge base. On any given polypeptide, the PTM with the closest spatial relationship to an ADP-ribosylation site, or within the random aspartate or glutamate control, were retained for analysis and visualization.

Determination of ADP-Ribosylation Site Motifs.

Sequences±8 amino acids from all unique ADP-ribosylation sites for PARP-1, PARP-2, and PARP-3 were analyzed for statistically significant enrichment of amino acid sequences using the Motif-X server (Chou and Schwartz, 2011 and Schwartz and Gygi, 2005), with a significance threshold of 0.005.

Determination Enriched 7-Mer Amino Acid Sequences Proximal to ADP-Ribosylation Sites.

Amino acid sequences±100 residues from all unique ADP-ribosylation sites for PARP-1, PARP-2, and PARP-3 were analyzed for the relative frequency of all overlapping 7-mer sequences using a custom script.

8-Bu(3-yne)T-ADP-ribosylation Reactions in Intact Nuclei.

MEFs were harvested in cold PBS and collected by centrifugation. The cells were swollen in Nuclei Isolation Buffer (10 mM HEPES, pH 8.0, 2 mM $MgCl_2$, 3 mM $CaCl_2$, 300 mM sucrose, with freshly added 1 mM DTT, protease inhibitors, and phosphatase inhibitors) and the nuclei were released by the addition of 0.65% NP-40 with moderate vortexing. Following collection by centrifugation, the nuclei were resuspended in PARP Reaction Buffer (30 mM Tris.HCl, pH 7.5, 10 mM KCl, 5 mM $MgCl_2$, 5 mM $CaCl_2$, 0.01% NP-40, 0.05 mM EDTA, 20% glycerol, with freshly added 1 mM DTT, protease inhibitors, and phosphatase inhibitors) containing 250 µM 8-Bu(3-yne)T-$NAD^+$ for 30 minutes at 25° C. with occasional gentle mixing to allow ADP-ribosylation to occur in the isolated nuclei.

Confocal Microscopy.

Following 8-Bu(3-yne)T-ADP-ribosylation in intact nuclei from MEFs as described above, the nuclei were washed once with Nuclei Click Reaction Buffer (10 mM HEPES, pH 8.0, 10 mM NaCl, 10 mM spermidine, 0.1% NP-40, with freshly added protease inhibitors) and then clicked twice to Alexa Fluor 488 by the sequential addition of 100 µM azido-Alexa Fluor 488 (Life Technologies), a pre-formed complex of $CuSO_4$:THPTA (1.0 mM:5.0 mM), and 5 mM sodium ascorbate. The nuclei were then washed with Nuclei Clicking Buffer to remove unclicked azido-Alexa Fluor 488. The nuclear DNA was stained by incubating the nuclei with 1 µM To-Pro DNA Stain (Life Technologies) in Nuclei Click Reaction Buffer for 2 minutes, with subsequent washing using Nuclei Click Reaction Buffer to remove unincorporated DNA stain. The nuclei were pipetted onto a glass cover slip, wicked dry with Whatman 3MM filter paper, covered with VectaShield (Vector Laboratories), and adhered to a glass slide. Fluorescence was visualized via confocal microscopy using a Leica TCS SP2 Confocal Microscope.

Click-ChIP-Seq.

The inventors developed a methods based on the analog-sensitive PARP technology for localizing ADP-ribosylation events mediated by a specific nuclear PARP (e.g., PARP-1) to specific sites in the genome. The inventors refer to this as click chemistry-based technology "Click-ChIP-seq," for clicked chromatin interaction and precipitation coupled with deep sequencing, which is similar in many respects to standard ChIP-seq protocols.

Formaldehyde Crosslinking in Intact Nuclei.

Following 8-Bu(3-yne)T-ADP-ribosylation in intact nuclei from MEFs as described above, the nuclei were collected by centrifugation and resuspended to homogeneity in Nuclei Crosslinking Buffer (10 mM HEPES, pH 8.0, 10 mM NaCl, 10 mM $MgCl_2$, 0.1% NP-40, with freshly added protease inhibitors) and crosslinked by addition of 0.5% methanol-free formaldehyde (Pierce) for 10 minutes while mixing slowly on a rotary mixer. Crosslinking was quenched by the addition of glycine to a final concentration of 275 mM with incubation on ice for 10 minutes. The nuclei were centrifuged at 500 RCF for 10 minutes before the 8-Bu(3-yne)T-ADP-ribosylated proteins were clicked to biotin for subsequent analysis.

Enrichment of 8-Bu(3-Yne) T-ADP-Ribose-Associated Regions of the Genome.

Following crosslinking as described above, the nuclei were washed thoroughly with Nuclei Click Reaction Buffer. ADP-ribosylated proteins in the nuclei were then clicked twice to biotin by resuspension of the nuclei in Nuclei Click Reaction Buffer with sequential addition of 100 µM azido-biotin (Click Chemistry Tools), a pre-formed complex of $CuSO_4$:THPTA (1.0 mM:5.0 mM), and 5 mM sodium ascorbate. The nuclei were then washed thoroughly in Nuclei Click Reaction Buffer to remove unclicked azido-biotin and resuspended in ChIP Lysis Buffer (50 mM Tris.HCl, pH 7.9, 1% SDS, 10 mM EDTA, 1× protease inhibitor cocktail (Roche)). The resuspended nuclei were sonicated in a water bath sonicator (Diagenode) to a DNA fragment size distribution of 200 to 500 bp. The biotinylated and sonicated chromatin was diluted ten-fold in ChIP Dilution Buffer (20 mM Tris.HCl, pH 7.9, 2 mM EDTA, 150 mM NaCl, 0.5% Triton X-100, 1 mM DTT, 1× protease inhibitor cocktail, 1% BSA) and bound to MyOne T1 streptavidin-conjugated magnetic beads (Invitrogen) by incubation overnight at 4° C. with gentle mixing.

After the incubation, the beads were collected in a magnetic field and washed by resuspension as specified in the following buffers: (1) twice in with 2% SDS, (2) once with Low Salt Precipitated Complex Wash Buffer (20 mM Tris.HCl, pH 8.1, 2 mM EDTA, 125 mM NaCl, 0.05% SDS, 1% Triton X-100, 1 µM aprotinin, and 100 µM leupeptin), (3) three times with High Salt Immune Complex Wash Buffer (20 mM Tris.HCl, pH 8.1, 2 mM EDTA, 500 mM NaCl, 0.05% SDS, 1% Triton X-100, 1 µM aprotinin, and 100 µM leupeptin), (4) once with LiCl Wash Buffer (10 mM Tris.HCl, pH 8.1, 1 mM EDTA, 250 mM LiCl, 1% NP-40, 1% sodium deoxycholate, 1 µM aprotinin, and 100 µM leupeptin), and (5) twice with 1×TE (10 mM Tris.HCl, 1 mM EDTA). The beads were collected in a magnetic field after the final wash and resuspended in 200 µL of De-crosslinking Buffer (100 mM sodium bicarbonate, 1% SDS, 100 mM NaCl). The 8-Bu(3-yne)T-ADP-ribose-associated DNA was released from beads by incubation in the De-crosslinking Buffer overnight at 65° C. and isolated away from the beads by magnetic separation. The beads were washed with once with 1×TE, which was combined with the initial eluate. The eluted DNA was treated with RNase and then protease, and purified by phenol:chloroform:isoamyl alcohol extraction (25:24:1). The resulting DNA was ethanol precipitated, washed with 70% ethanol, dried, and resuspended in 10 mM Tris.HCl in a volume determined by the subsequent assays. For quantitative PCR, the 8-Bu(3-yne)

T-ADP-ribose-precipitated DNA was analyzed using a Roche LightCycler 480 (Hendriks et al., 2014) and compared to a retained input fraction (de-crosslinked and purified as above).

Preparation of Click-ChIP-Seq and ChIP-Seq Libraries for Deep Sequencing.

Click-ChIP-seq libraries for deep sequencing were prepared from the 8-Bu(3-yne)T-ADP-ribose-precipitated DNA essentially as previously described (Luo, 2014). For ChIP-seq libraries prepared from intact nuclei, the isolated nuclei were subjected to mock ADP-ribosylation and azido-biotin click chemistry reactions, sonicated, and diluted in ChIP Dilution Buffer as described above. PARP-1 bound to chromatin was immunoprecipitated from the sonicated chromatin essentially as described previously (Luo, 2014) using anti-FLAG M2 agarose (Sigma). The ChIP'ed DNA was prepared for high throughput sequencing as previously described (Luo, 2014). The Click-ChIP-seq and ChIP-seq libraries were sequenced using an Illumina HiSeq instrument at the McDermott Center Sequencing Core Facility at UT Southwestern Medical Center.

Analysis of Click-ChIP-Seq and ChIP-Seq Data.

Software, scripts, and other information about the analyses can be obtained by contacting the corresponding author (W.L.K.).

Quality Control.

Quality control for the Click-ChIP-seq and ChIP-seq data was performed using the FastQC tool (world-wide-web at bioinformatics.babraham.ac.uk/projects/fastqc/).

Read Alignment and Visualization.

The deep sequencing reads were aligned to the human genome (hg19) using default parameters in bowtie (Langmead et al., 2009). The Click-ChIP-seq data were prepared for visualization by calculating the odds ratio of Click-ChIP-seq relative to input across the genome in 2500 bp windows with 250 bp steps. The Click-ChIP-seq odds ratios were then converted into bigwig files using BEDTools (Quinlan and Hall, 2010) and visualized using the IGV genome browser (Robinson et al., 2011 and Thorvaldsdottir et al., 2013) with a 2-fold cutoff for color intensity. The H3K4me3 and NELF ChIP-seq data were from published sources (Shen et al., 2012 and Sun et al., 2011). Uniquely mappable ChIP-seq read densities were converted into bigWig files using BED-Tools and visualized using the IGV genome browser.

Peak Calling and Genome-Wide Dataset Correlations.

Genomic sites of enrichment for transcription or chromatin proteins, or histone modifications were calculated using SICER (Zang et al., 2009) with a false discovery rate of $1 \times 10^{-2}$ for all data sets evaluated. Enrichment of NELF-E, SA1, SA2, SMC1, SMC3, CTCF, CDK9, and H3K4me3 was determined using a window and gap size of 200 bp. Enrichment of PARP-1, H3K36me3, H3K27me3, and H3K9me3 was determined using a window size of 200 bp and a gap size of 600 bp. Enrichment of lamins was determined using a window size of 1,000 bp and a gap size of 3000 bp. To determine the correlation of PARP-1-dependent ADP-ribosylation with a transcription or chromatin protein, or a histone modification, a Pearson's correlation coefficient was calculated between the normalized read depth for each factor underneath their requisite peaks and the input-normalized Click-ChIP-seq signals.

Heatmaps.

Read densities in a 10 kb window surrounding the RefSeq TSS (±5 kb) were determined using a custom script in the programming language R and visualized as heatmaps using Java TreeView (Saldanha, 2004).

Analysis of CDK9 Enrichment, PARP-1-Mediated ADP-Ribosylation, and RNA Polymerase Pausing.

For every actively transcribed RefSeq mouse promoter, CDK9 occupancy and ADP-ribosylation enrichment were calculated in a 1 kb window surrounding the TSS (±500 bp). RNA polymerase II pausing indices were then calculated for these promoters as described below. Promoters were binned according to increasing occupancy of CDK9 or enrichment of PARP-1-mediated ADP-ribosylation, and an increase or decrease in RNA polymerase II pausing was calculated for the binned promoters versus all RefSeq promoters. The results of these analyses were plotted according to the absolute value of the increase or decrease in RNA polymerase II pausing and the associated t-test-calculated p-value for this determination.

Analysis of ChIP-Chip Data.

NELF-E ChiP-chip data from MCF-7 cells (Kininis et al., 2009) were downloaded from the GEO database. Probe sequences for the custom chip array, each associated with a log 2 odds ratio value from the NELF-E ChIP-chip experiment, were aligned to the human reference genome (hg19) using the bowtie aligner (Langmead et al., 2009). Statistically significant NELF-E peaks were called as described previously (Krishnakumar et al., 2008) with a 2-fold odds ratio cut-off. NELF-E binding sites were calculated from the called peaks and assigned to a promoter when occurring within the first 500 bp of a RefSeq promoter. Software, scripts, and other information about the analyses can be obtained by contacting the corresponding author (W.L.K.).

Preparation of GRO-Seq Libraries.

Preparation of Nuclei. MCF-7 cells with shRNA-mediated knockdown of luciferase (Luc; as a control) or PARP-1 were described previously (Frizzell et al., 2009). Nuclei were isolated from the Luc and PARP-1 knockdown cell lines were subjected to GRO-seq as described previously (Hah et al., 2011). Briefly, MCF-7 cells were washed three times with ice-cold PBS and then resuspended for swelling in ice-cold Hypotonic Lysis Buffer [10 mM Tris.HCl, pH 7.4, 0.5% NP-40, 10% Glycerol, 3 mM $CaCl_2$, 2 mM $MgCl_2$, and 1 mM DTT containing 1× protease inhibitor cocktail (Sigma-Aldrich) and 4 units/mL SUPERase-In (Ambion)]. The swollen cells were collected by centrifugation at 1000 RCF for 10 min at 4° C. and then resuspended in 1.5 ml of lysis buffer and pipetted up and down through a narrow opening tip 30 to 50 times to lyse the cells and release the nuclei. The nuclei were collected by centrifugation and washed once with 1 mL of Hypotonic Lysis Buffer. After a final collection by centrifugation, the resulting pellets of nuclei were resuspended in 500 µL of Freezing Buffer (50 mM Tris.HCl, pH 8.3, 40% glycerol, 5 mM $MgCl_2$, 0.1 mM EDTA, and 4 units/mL of SUPERase-In per mL), counted, frozen in liquid nitrogen in 100 µL aliquots containing $5 \times 10^6$ nuclei, and stored at −80° C. until use.

Nuclear Run-on and Library Preparation.

Nuclear run-on and GRO-seq library preparation were performed as previously described (Hah et al., 2011 and Core et al., 2008). Briefly, nuclear run-on reactions were performed for ~100 bases in the presence of sarksoyl (to prevent reengagement of RNA polymerases), rNTPs, $\alpha^{32}P$-CTP, and 5-bromo-UTP. The nascent RNAs were isolated, hydrolyzed to ~100 bases, and enriched using α-BrdUTP antibody-conjugated agarose beads (Santa Cruz). The bound RNAs were washed several times and eluted. The 5' RNA cap was removed and the ends were repaired in preparation for adapter ligation. Small RNA adapters were ligated to the 5' end, followed by another bead binding enrichment using α-BrdUTP antibody-conjugated agarose beads. These steps were repeated using a 3' adapter. The resulting RNAs were reverse transcribed, amplified using PCR, and analyzed by high throughput sequencing using an Illumina 1G Genome Analyzer.

Analysis of GRO-Seq Data.

The GRO-seq data were analyzed using software described previously (Hah et al., 2011) and the approaches described below. Software, scripts, and other information about the analyses can be obtained by contacting the corresponding author (W.L.K.).

Quality Control.

Quality control for the GRO-seq data was performed using the FastQC tool (world-wide-web at bioinformatics.babraham.ac.uk/projects/fastqc/). The GRO-seq reads were trimmed to remove adapter contamination using the default parameters of Cutadapt software (Martin, 2011). Reads >32 bp long were retained for alignment.

Read Alignment and Gene Annotations.

Trimmed human GRO-seq reads were aligned to the human reference genome (hg19) using the bwa aligner (Langmead et al., 2009) with default settings (uniquely aligned, 2 mismatches allowed, and 19 bp seed sequence). The 5'-most base pair from each read was used in all analyses, with no more than 2 duplicates allowed at any genomic location. Mouse GRO-seq reads were aligned to the mouse reference genome (mm9) using the bowtie aligner (Langmead et al., 2009) with default settings (uniquely aligned, 2 mismatches allowed, and 19 bp seed sequence). As above, the 5'-most base pair from each read was used in all analyses. For genes with multiple TSSs, the inventors used the TSS with the most GRO-seq reads within the first 150 bp in the genic sense direction.

Determination of Transcription Levels.

Transcription levels were calculated by counting the total GRO-seq reads across the entire transcript and dividing by the length of the transcript in base pairs. Overlaps and redundancies were removed from the combined gene lists to eliminate the possibility of double counting genes.

Analysis of Pausing Indices.

Pausing indices representing the base pair normalized difference in read depth between the promoter proximal region (1-250 bp) and the gene body region (1-13 kb) were calculated as described (Danko et al., 2013). The effect of PARP-1 knockdown on the level of paused RNA polymerase was determined using edgeR (Robinson et al., 2010). Pausing indices was calculated for every RefSeq gene as described above from GRO-seq replicates normalized for read depth by random read subtraction. EdgeR was run without a library read depth adjustment and with a p-value cutoff of 0.001 to determine significant changes in RNA polymerase pausing.

Heatmaps and Metagenes.

The read densities of sense and anti-sense reads were calculated on adjacent lines for a 10 kb window surrounding each RefSeq TSS (+5 kb) of using a custom script in the R programming language. The data were visualized as heatmaps using Java TreeView (Saldanha, 2004), with sense and anti-sense reads for each RefSeq promoter and colored red and blue, respectively. Metagenes were generated as previously described (Hah et al., 2011).

Genomic Datasets.

The new genomic data sets generated for these studies are as follows: (1) MCF-7 GRO-seq (Luc knockdown and PARP-1 knockdown), and (2) MEF PARP-1 ChIP- and Click-ChIP-seq in intact nuclei. They are available from the NCBI's GEO database using accession numbers GSE74141 and GSE74142 respectively.

The following publically available deep sequencing data sets (including their cognate controls) were downloaded from NCBI's GEO archive using the following accession numbers: H3K36me3 ChIP-seq (GSE12241); Lamin B1-DamID (GSE17051); NELF-B ChIP-seq (GSE24113); SA1, SA2, SMC1, and SMC3 ChIP-seq (GSE32319); CTCF and H3K4me3 ChIP-seq (GSE29218); H3K9me3 and H3K27me3 (GSE22268); CDK9 ChIP-seq (GSE45517).

Oligonucleotide Sequences:
shRNAs
(listed 5' to 3)

| Luc #1 | GGAAUCCAGUGUGUGAAGA[dT][dT] |
| Luc #2 | GAGAGAAAAAAUCAACAGC[dT][dT] |
| PARP-1 #1 | GUGUAGACAUCCUCCGUAU[dT][dT] |
| PARP-1 #2 | CAUACUCUAUUCCGAGUAU[dT][dT] |

Primers for Click-ChIP-qPCR
(listed 5' to 3')

FKBP5 Fwd:
GTCCAGCCAGACCAAACAGT

FKBP5 Rev:
AAGGGACACAGGGTGTGAAG

CEBPA Fwd:
CTGGAAGTGGGTGACTTAGAGG

CEBPA Rev:
GAGTGGGGAGCATAGTGCTAG

Example 2—Results

In order to identify the direct and specific targets of PARPs in cells, an analog-sensitive PARP mutant approach was developed, where a specific mutation at a highly conserved residue in the catalytic site of PARPs can facilitate ADP-ribosylation using unnatural analogs of NAD (FIG. 5A). These NAD analogs did not support the catalytic active wild-type PARP proteins, but rather are used in conjunction with the analog-sensitive mutant in what is often called a "bump and hole" approach (FIG. 5A). Two conserved "gatekeeper residues" in human PARP-1 were identified that confer analog sensitivity when mutated to alanine (A)— Leucine 877 and Isoleucine 895, yielding L877A and I895A PARP-1 mutants. These PARP-1 mutants showed NAD analog sensitive catalytic activity to a varying extent with the NAD analogs tested in automodification reactions with purified PARP-1 proteins (FIG. 5E).

Figure 2:
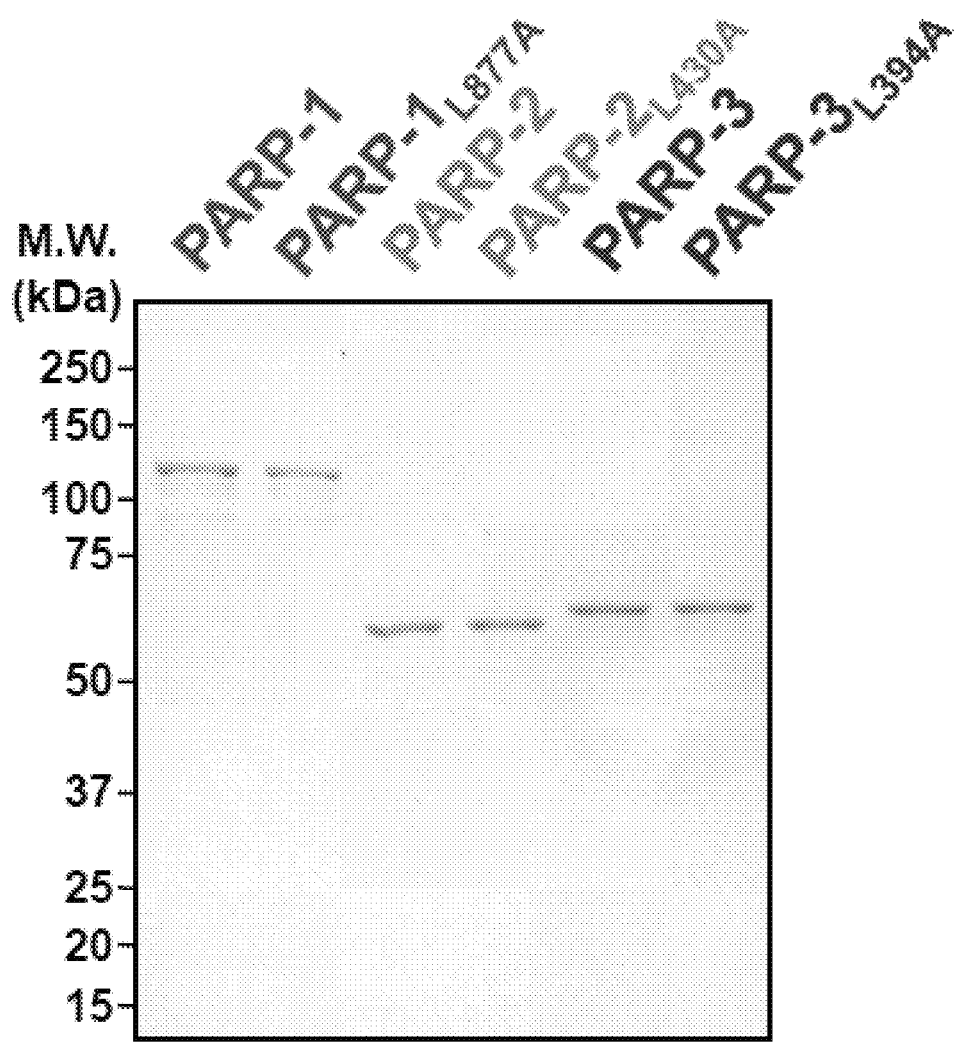
FIG. 2—Purification of analog-sensitive PARP-1, PARP-2, and PARP-3 mutants: Purification of wild-type and analog-sensitive (i.e., PARP-$1_{L877A}$, PARP-$2_{L430A}$, PARP-$3_{L394A}$) PARP proteins expressed in Sf9 cells using a baculovirus expression system. The FLAG-tagged recombinant proteins were purified using FLAG-affinity chromatography. The purified proteins were run on a 10% PAGE-SDS resolving gel, which was stained with Coomassie brilliant blue. The molecular weights (MW) in kilodaltons (kDa) of marker proteins run on the same gels are shown.

Leucine 877 in PARP-1 is conserved positionally and functionally across many members of the PARP family, including PARP-2 (L430) and PARP-3 (L394). Wild-type and analog-sensitive PARP (asPARP) mutants (e.g., PARP-$1_{L877A}$, PARP-$2_{L430A}$, PARP-$3_{L394A}$) were expressed as FLAG epitope-tagged proteins in Sf9 insect cells and purified using anti-FLAG immunoaffinity chromatography (FIG. 2). asPARP-1, asPARP-2, and asPARP-3 were catalytically active with a clickable NAD analog, 8-Bu(3-yne) T-NAD, whereas wild-type PARP-1, PARP-2, and PARP-3 were not (FIG. 5I). The clickable moiety (i.e., alkyne) on 8-Bu(3-yne)T-NAD was transferred by asPARPs to their protein targets in automodification (FIG. 5I) or transmodification reactions (FIG. 3) in vitro as 8-Bu(3-yne)T-ADP-ribose, which was clicked to azido-fluorophores, such as azido-rhodamine (FIGS. 5I & 6A).

Figure 4A:
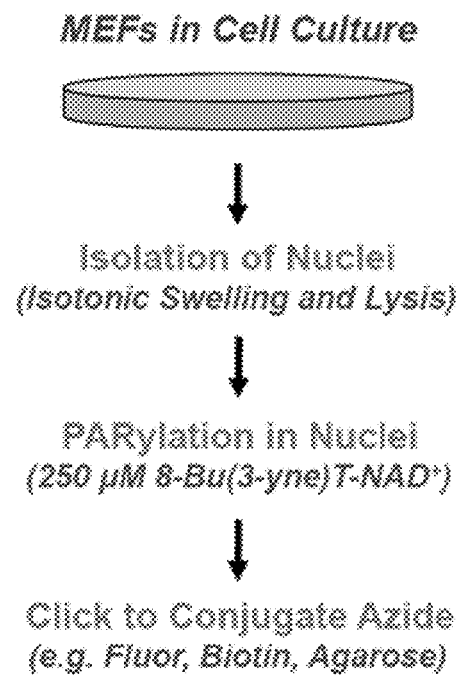
FIGS. 4A & 4B—Direct labeling of PARP-1 substrates in intact nuclei.
Figure 4B:
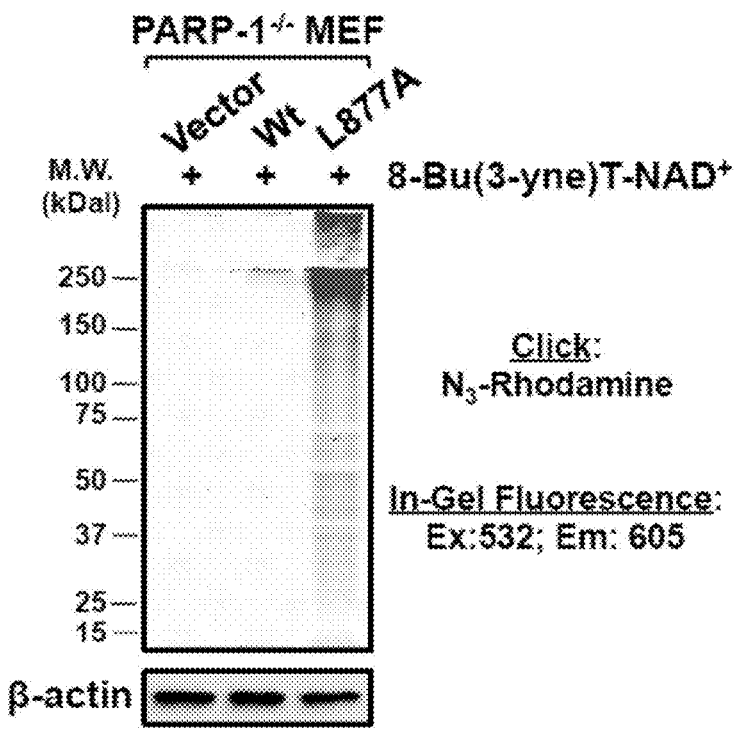
Figure 15:
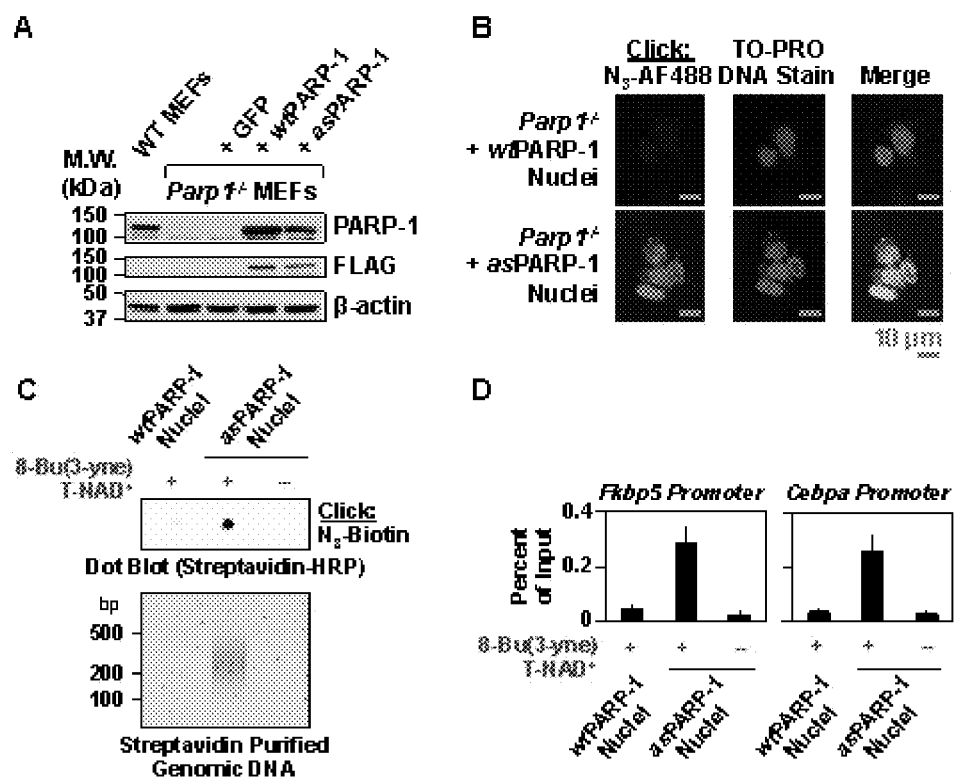
FIGS. 15A-D. Development of Click-ChIP-seq, a nuclei-based assay using asPARP-1 technology to identify sites of PARP-1-mediated ADP-ribosylation genome-wide.

Transmodification in nuclear extracts from mammalian cells using asPARP-1, asPARP-2, or asPARP-3 and 8-Bu(3-yne)T-NAD was used to identify ADP-ribosylated proteins, as well as the specific amino acid residues modified, when coupled with mass spectrometry (FIGS. 6C, 6D and 6H). Nuclear PARPs (e.g., PARPs 1, 2, and 3) are used to modify nuclear proteins involved in transcription, DNA repair, RNA splicing, and chromosome organization (FIGS. 6E-F). The Negative Elongation Factor NELF is a protein complex with two subunits which were ADP-ribosylated by PARP-1 and PARP-3 (FIG. 7B). These sites of modification were first identified using the asPARP approach.

asPARP mutants were also catalytically active with NAD analogs in intact nuclei. In one non-limiting example, ectopically expressed asPARP-1 was catalytically active with 8-Bu(3-yne)T-NAD in nuclei from Parp1$^{-/-}$ mouse embryo fibroblasts (MEFs) (FIGS. 4A-B). The asPARP mutants were also useful for examining ADP-ribosylation events that occur in specific subcellular compartments or on specific subcellular structures. In one non-limiting example, asPARP-1 were used to ADP-ribosylate chromatin-associated proteins in intact nuclei using 8-Bu(3-yne)T-NAD. The 8-Bu(3-yne)T-ADP-ribosylated chromatin-associated proteins were then used to precipitate fragments of the underlying genomic DNA in a Click-ChIP assay (FIG. 15C). With this method, both the 8-Bu(3-yne)T-ADP-ribosylated chromatin-associated proteins and the underlying genomic DNA were readily detected (FIG. 15C). In addition, genomic DNA sequences from specific genomic loci were detected in the precipitated genomic DNA fragments by real time quantitative PCR (qPCR) in a Click-ChIP-qPCR assay (FIG. 15D). This analysis was performed on a global genomic scale by substituting the qPCR assay with next generation sequencing technology in a Click-ChIP-seq assay (FIG. 8D, see "ADP-ribose from PARP-1"). These results showed that PARP-1-dependent ADP-ribosylation of chromatin-associated proteins (as determined by Click-ChIP-seq) overlaps with sites of PARP-1 binding (as determined by in nuclei ChIP-seq), active transcription (as determined by GRO-seq), histone H3 lysine 4 trimethylation (H3K4me3; as determined by ChIP-seq), and NELF-E binding (as determined by ChIP-seq) (FIGS. 8B and 8D).

FIG. 5A shows an NAD$^+$ analog-sensitive approach for PARPs that preserves the natural mono- or poly(ADP-ribosyl) transferase activities of the enzymes and is capable of identifying the specific targets of individual PARP family members. Analog-sensitivity is achieved by mutation of a large "gatekeeper" amino acid in the active site of a protein to a smaller residue, creating a pocket that fits a bulky R group on an engineered substrate whose interactions with the wild-type enzyme are sterically blocked (Wessel and Flugge, 1984). The analog-sensitive strategy, which creates substrate specificity within a class of enzymes that all use the same substrate and generate the same post-translational modification, remains one of the most definitive approaches for identifying direct targets of protein-modifying enzymes.

In order to engineer analog-sensitivity in PARPs, the inventors initially focused on PARP-1, an abundant and ubiquitously expressed PARP protein. To identify a "gatekeeper" residue in PARP-1, they changed 10 large residues buried within the active site and facing the adenine ring of NAD$^+$ to both glycine and alanine based on a molecular model (FIG. 5B and FIGS. 9A-C). The inventors selected the 8 position of the adenine ring of NAD$^+$ as the site for R group addition since its modification precludes ADP-ribosylation with wild-type PARP-1 (wtPARP-1) or other PARPs (Dignam et al., 1983), a feature critical to the analog-sensitive approach. They then synthesized a library of 11 NAD$^+$ analogs, each with a different R group at position 8, from 8-methylamino-NAD$^+$ to 8-benzylamino-NAD$^+$ (FIG. 5C). In a screen of the 20 PARP-1 mutants versus the 11 NAD$^+$ analogs (FIGS. 5D-E; FIGS. 10A-C), the inventors identified two different gatekeeper residues, leucine 877 and isoleucine 895, whose mutation to alanine results in analog-sensitive activity in a PARP-1 automodification assay. PARP-1 (L877A) (i.e., analog-sensitive PARP-1 or asPARP-1) was active with five NAD$^+$ analogs, whereas PARP-1 (I895A) was active with two (FIG. 5E). While L$_{877}$ and I895 are 18 amino acids from one another in the PARP-1 linear sequence, they are adjacent to one another and proximal to the 8 position of the adenine ring in three-dimensional space (FIG. 5F). These results support the inventors' molecular model of PARP-1 interaction with NAD$^+$, as well as the structural basis for our asPARP approach.

To extend the utility of asPARP approach, the inventors functionalized the R group of NAD$^+$ analog 6 (FIG. 5C), 8-Butylthio-NAD$^+$, with an alkyne to generate 8-Bu(3-yne) T-NAD$^+$ (FIG. 5G). 8-Bu(3-yne)T-NAD$^+$ is a "clickable" NAD$^+$ analog with a single bi-functional R group at position 8, facilitating asPARP-selective ADP-ribosylation, as well as alkyne incorporation into the post-translationally modified target for subsequent use in azide-alkyne cycloaddition reactions to label or purify the PARP targets (FIG. 5H). PARP-1 (L877A) with 8-Bu(3-yne)T-NAD$^+$ yields similar activity as previously screened analogs, nearing wild-type enzyme kinetics when compared to PARP-1 and NAD$^+$ (FIGS. 11A-F). Critically, this clickable NAD$^+$ analog also supports activity with asPARP-2 and asPARP-3 mutants (L443A and L394A, respectively), which contain alanine substitutions at residues homologous to L$_{877}$ of PARP-1 (FIG. 5I; FIGS. 11A-B). The ability to transfer this analog-sensitive activity with 8-Bu(3-yne)T-NAD$^+$ by homology at the conserved gatekeeper residue (FIG. 5I; FIGS. 11D-G) suggests broad utility of this approach across the PARP family, for both mono- and poly(ADP-ribosyl) transferases. In subsequent studies, described below, the inventors used the asPARP approach to identify the protein targets of specific PARPs, as well as the sites of PARP-1-mediated ADP-ribosylation across the genome.

The inventors used the asPARP approach to identify site-specific nuclear targets of PARPs 1, 2, and 3 with an approach that focuses on glutamate and aspartate residues. They incubated purified recombinant asPARPs 1, 2, or 3 with HeLa cell nuclear extract in the presence of 8-Bu(3-yne)T-NAD$^+$, which resulted in PARP-specific labeling of extract proteins (FIG. 8A). The inventors then clicked the 8-Bu(3-yne)T-ADP-ribose-labeled proteins to azide-agarose resulting in their covalent attachment to the agarose resin, allowing extensive washing with denaturants, strong detergents, and organic solvents. After isolation of the PARP-specific ADP-ribosylated proteins, they performed trypsin-based peptide identification by LC-MS/MS (Peptide ID), washed extensively again, and eluted the ADP-ribosylated peptides using hydroxylamine to identify the sites of ADP-ribosylation by LC-MS/MS (Site ID), as previously described (Colowick et al., 1951) (FIG. 8B). This approach revealed unique, as well as overlapping, sites of PARP-1-, 2-, and 3-mediated ADP-ribosylation (FIGS. 6C-D). Ontological analyses of the target proteins revealed enrichment of terms related to transcription and DNA-repair, consistent with the known biology of PARPs 1, 2, and 3 (FIG. 6E-F). In addition, the inventors observed an enrichment of terms and specific target proteins related to RNA splicing and processing (all three PARPs), DNA metabolism (PARP-2), and cell cycle regulation (PARP-3) (FIGS. 6E-F), suggesting new functions for these PARPs.

Figure 13:
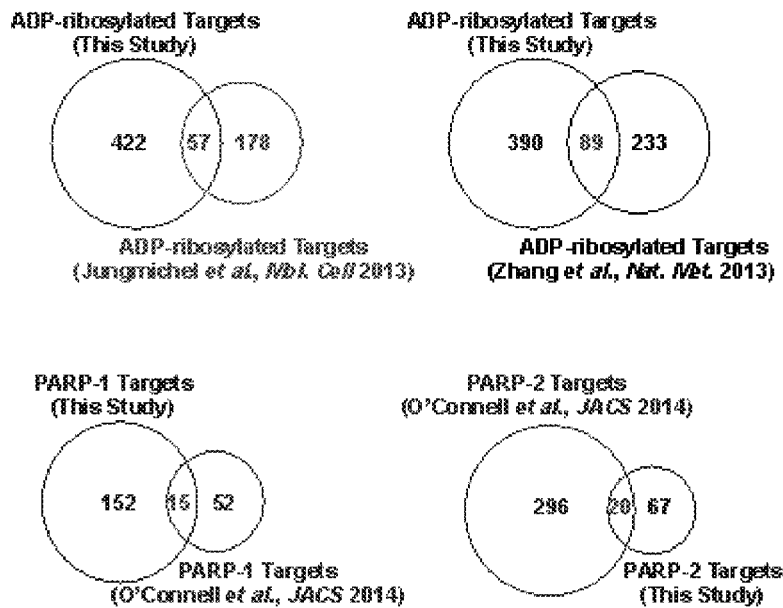
FIG. 13. Overlap of PARP targets with targets reported in the literature. Venn diagram representations of overlap between PARP-1, PARP-2, and PARP-3 targets identified in this study with targets identified using other approaches reported in the literature: ADP-ribosylated targets—Jungmichel et al. (2013) (1) and Zhang et al. (2013) (2); PARP-1 targets and PARP-2 targets—O'Connell et al. (2014) (3).

Motif analyses at the sites of PARP-1-, 2-, and 3-mediated ADP-ribosylation indicate some similarities in sequence preference among the three PARPs (e.g., glutamate proximal to the site of modification, labeled as position "0" in FIG. 6G), but differences as well (e.g., lysine or arginine 6-8 amino acids N-terminal or 4-8 amino acids C-terminal to the site of modification for PARP-3 only; FIG. 6G). PARP-1 modification sites are enriched for proline 1-2 amino acids C-terminal to the ADP-ribosylated glutamates (FIG. 6G). Interestingly, this same preference for proline was observed when profiling bulk ADP-ribosylation sites during a response to oxidative DNA damage (Colowick et al., 1951), which primarily stimulates PARP-1 activity. The sites of PARP-1-, 2-, and 3-mediated ADP-ribosylation that the inventors identified herein partially overlapped and were more numerous than sites of ADP-ribosylation identified using other approaches (FIG. 13), although good agreement for the specific sites of ADP-ribosylation was observed between the results of our asPARP biochemical approach and a previous cell-based bulk ADP-ribosylation assay for common targets (Colowick et al., 1951) (FIG. 6H). Collectively, these results demonstrate the power of our asPARP approach to robustly and faithfully identify sites of ADP-ribosylation mediated by a specific PARP family member.

Figure 14:
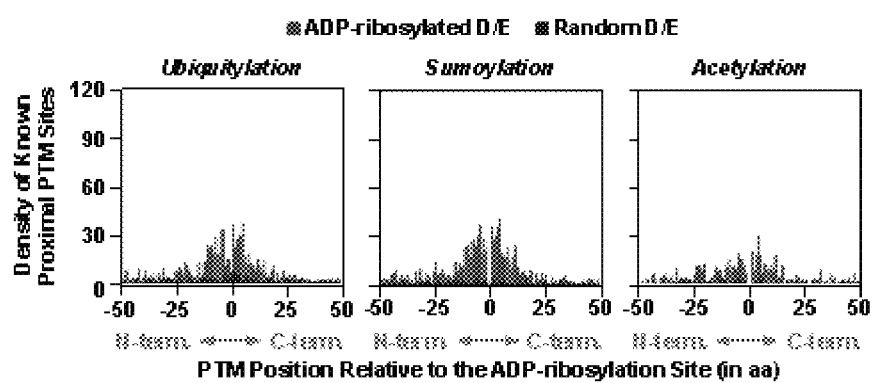
FIG. 14. Other post-translational modifications associated with PARP target modification sites. Histograms of the two-dimensional relationship between ADP-ribosylation sites identified herein and the nearest incidence of any known sites of ubiquitylation (left), sumoylation (middle), and acetylation (right) on PARP target proteins.

To explore in more detail potential sequence-based "rules" for ADP-ribosylation, the inventors determined the enrichment of 7-mer amino acid sequences near sites of PARP-1-, 2-, and 3-mediated ADP-ribosylation. They observed enrichment of a number of different sequences, including RSRSRDR (FIG. 7A). Interestingly, over half of the occurrences of thi 7-mer within the human genome are targets of PARP-1 (not shown), including NELF-E (FIG. 6F and FIG. 7B), a subunit of the NELF complex whose function is to restrict transcriptional elongation and stimulate promoter-proximal pausing by RNA polymerase II (Pol II) (Huang et al., 2007a). In NELF-E, the motif is located near a cluster of PARP-1-mediated ADP-ribosylation sites and is within the previously identified phosphorylation target site for P-TEFb, a complex containing CDK9 and cyclin TI, which coordinates the release of paused Pol II into productive elongation through phosphorylation of Pol II, DSIF, and NELF (Huang et al., 2007b and Hornbeck et al., 2012) (FIG. 7B). Interestingly, phosphorylation sites (FIG. 7C) and, to a lesser extent, sites of other post-translational modifications (FIG. 14), are frequently found at or near ADP-ribosylation sites across the proteome. This suggests a broad role for ADP-ribosylation as a modulator at hubs of regulatory activity, as well as a more specific regulatory role for ADP-ribosylation (and PARPs) in cooperation with phosphorylation (and kinases) across the proteome.

Given previous reports implicating the *D. melanogaster* homolog of PARP-1 as a key modulator of Pol II pause release at heat shock loci (Hendriks et al., 2014 and Chou and Schwartz, 2011), the identification of NELF-E as an ADP-ribosylated PARP-1 target protein led us to explore the functional interplay between these two proteins in more detail. Immunoaffinity purification of NELF from mammalian cells expressing FLAG epitope-tagged NELF-E indicates that PARP-1 interacts with the NELF complex (FIG. 7D), and that NELF-E and NELF-A are ADP-ribosylated in mammalian cells (FIG. 7E).

The inventors confirmed that the four glutamate residues that they identified in our proteomic screen (E122, E151, E172, and E374; FIG. 7B) are indeed major sites of ADP-ribosylation by PARP-1 using an in vitro modification assay with purified PARP-1 and ADP-ribosylation site mutant GST-tagged NELF-E (FIG. 7F). Mutation of these glutamates to glutamines, a structurally similar residue refractory to ADP-ribosylation, resulted in a substantial reduction in NELF-E modification by PARP-1 (FIG. 7F). Using a PARP inhibitor (i.e., PJ34) and a CDK9 inhibitor (i.e., flavopiridol), the inventors observed that ADP-ribosylation of NELF-E in mammalian cells is dependent on phosphorylation by CDK9/P-TEFb (FIG. 7G), a kinase that phosphorylates Pol II, DSIF, and NELF-E. Finally, using an electrophoretic mobility shift assay with a model NELF-E-interacting RNA (i.e., HIV TAR), the inventors found that ADP-ribosylation of NELF-E ablates its ability to bind RNA, a function of NELF-E necessary for the establishment paused Pol II (Schwartz and Gygi, 2005) (FIG. 7H).

PARP-1 is a key regulator of gene expression outcomes in a variety of biological systems, modulating chromatin structure through its nucleosome-binding activity, and regulating components of chromatin and the transcriptional machinery through its catalytic activity (Hah et al., 2011). To define sites of PARP-1-mediated ADP-ribosylation across the genome, the inventors developed an assay, which the inventors call "Click-ChIP-seq" (click chemistry-based chromatin isolation and precipitation with deep sequencing), using the asPARP-1 approach in nuclei. The inventors re-expressed GFP (as a control), wtPARP-1, or asPARP-1 in Parp1$^{-/-}$ mouse embryo fibroblasts (MEFs) (FIG. 8A and FIG. 15A). ADP-ribosylation following addition of 8-Bu(3-yne)T-NAD$^+$ was clearly evident in the nuclei of Parp1$^{-/-}$ MEFs expressing asPARP-1, but not wtPARP-1 (FIG. 15B). They then (i) collected 8-Bu(3-yne)T-NAD+-treated nuclei, (ii) crosslinked them with formaldehyde, (iii) clicked the 8-Bu (3-yne)T-ADP-ribose to biotin, (iv) sheared the chromatin by sonication, (v) affinity purified the 8-Bu(3-yne)T-ADP-ribose-chromatin complexes using streptavidin-agarose, and (vi) purified the genomic DNA from those complexes (FIG. 8A and FIG. 15C). A qPCR-based assay of the enriched genomic DNA revealed asPARP-1-specific ADP-ribosylation at gene promoters in nuclei isolated from MEFs (FIG. 15D). To explore chromatin-associated ADP-ribosylation genome-wide, the inventors subjected the enriched genomic DNA to deep sequencing (FIG. 8A).

Click-ChIP-seq revealed robust enrichment of PARP-1-mediated ADP-ribosylation at the promoters of transcriptionally active genes, which were defined by an enrichment of histone H3 lysine 4 trimethylation (H3K4me3, a mark of active promoters, from ChIP-seq) and actively transcribing Pol II (from GRO-seq) (FIG. 8B). Genome-wide correlation analyses between PARP-1-mediated ADP-ribosylation and a variety of other histone modifications and chromatin/transcription-related factors revealed positive correlations with PARP-1, NELF-B, and CDK9, as well as components of a CTFC-cohesion (SMC1 and SA1/SA2) complex thought to be regulated by PARP-1-mediated ADP-ribosylation (FIG. 8C) (Luo, 2014). Heatmap representations of the genomic data highlight the striking relationships at gene promoters among PARP-1-mediated ADP-ribosylation, Pol II accumulation, and H3K4me3, NELF-B, and PARP-1 enrichment (FIG. 8D). Interestingly, PARP-1-mediated ADP-ribosylation and CDK9 occupancy at promoters strongly correlated with low levels of Pol II pausing (FIG. 8E). These results suggested to us that PARP-1-mediated ADP-ribosylation may act similarly to CDK9/P-TEFb-mediated phosphorylation to promote the release of paused Pol II into productive elongation.

Figure 16:
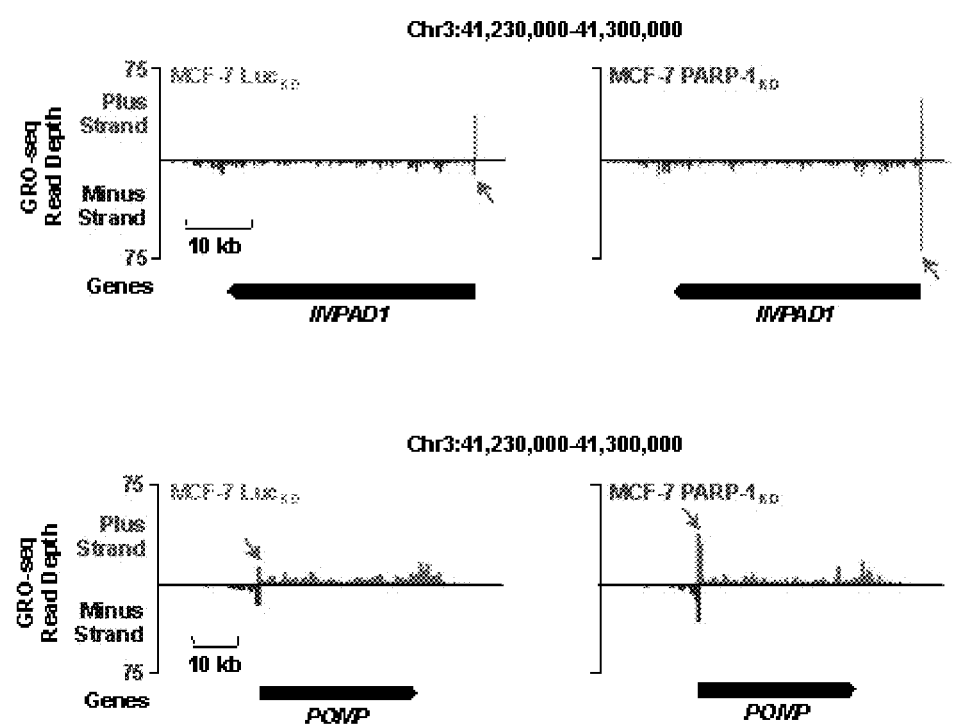
FIG. 16. Altered promoter-proximal RNA polymerase II pausing at specific genes in PARP-1-deficient MCF-7 cells. MCF-7 human breast cancer cells were subjected to knockdown (KD) with control (luciferase; LucKD) or PARP-1 (PARP-1KD) shRNAs, followed by global run-on sequencing (GRO-seq). Genome browser view of two representative loci of the human genome, containing the genes IMPAD1 (top) and POMP (bottom), showing normalized GRO-seq read densities from MCF-7 cells subjected to control (LucKD, left) or PARP-1 (PARP-1K, right) knockdown. Pink arrows indicate the location of the altered peak of paused Pol II.

To test this hypothesis, the inventors performed GRO-seq in MCF-7 breast cancer cells to monitor the effects of shRNA-mediated PARP-1 knockdown on Pol II pausing. They observed a dramatic accumulation of reads in the peaks of paused Pol II upon PARP-1 knockdown (compared to a control luciferase knockdown; Luc) at gene promoters, as determined by GRO-seq (FIG. 8F and FIG. 16). This effect was evident genome-wide (FIG. 8G), with a clear increase in global Pol II pausing indices upon PARP-1 knockdown (FIG. 8H). At active promoters with a significant accumulation of GRO-seq reads in the paused Pol II peak upon PARP-1 knockdown, the inventors observed decreased GRO-seq reads in the gene bodies, lower NELF-E occupancy at the promoters, and lower Pol II pausing prior to PARP-1 depletion (FIGS. 17A-F). These results suggest that PARP-1 modulates NELF activity at these promoters to achieve an efficient release of Pol II into productive elongation. Collectively, these data point to a clear functional link between CDK9-mediated phosphorylation, PARP-1-mediated ADP-ribosylation, and NELF-mediated Pol II pausing (data not shown).

Herein, the inventors have described the development of an $NAD^+$ analog-sensitive approach for PARP proteins that preserves the natural catalytic activities of both mono- and poly(ADP-ribosyl) transferases, in contrast to a previous approach (Liang et al., 2012). This asPARP approach uses a single point mutation buried within the PARP active site in concert with a single alkyne-containing R group on $NAD^+$ to achieve PARP-specific clickable ADP-ribosylation. They have demonstrated the robustness and transferability of this asPARP approach by using it to identify (i) PARP-1, 2, and 3 target proteins, as well as the specific sites of Glu and Asp ADP-ribosylation on those proteins, by mass spectrometry and (ii) PARP-1-mediated sites of ADP-ribosylation across the mammalian genome using deep sequencing. Importantly, this combination of chemical genetics, proteomics, and genomics has allowed us to develop and test new hypotheses about the biology of ADP-ribosylation in gene regulation. This has led to a model, supported by our data, in which PARP-1 (via ADP-ribosylation) and P-TEFb (via phosphorylation) act together to control Pol II pausing and release through the negative elongation factor NELF (data not shown). This integrated approach should have great utility across the family of PARPs, accelerating the discovery of previously unknown biological functions for ADP-ribosylation.

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the disclosure. All variations and modifications apparent to those skilled in the art are deemed to be within the spirit, scope, and concept of the disclosure as defined by the appended claims.

VI. REFERENCES

The following references, to the extent that they provide exemplary procedural or other details supplementary to those set forth herein, are specifically incorporated herein by reference:

Abdallah, et al., European Journal of Biochemistry/FEBS, 50, 475-481, 1975.
Ahel, et al., Nature. 451(7174):81-5, 2008.
Bailey et al., *Molecular Cancer Therapeutics* 13:724, March, 2014.
Buelow, et al., J Biol Chem. 283(36):24571-83, 2008.
Carter-O'Connell et al., Journal of the American Chemical Society 136:5201, Apr. 9, 2014.
Chou and Schwartz, Biological sequence motif discovery using motif-x. Current protocols in bioinformatics/editorial board, Andreas D. Baxevanis . . . [et al.] Chapter 13, Unit 13 15, September, 2011.
Colowick et al., The Journal of Biological Chemistry 191: 447, August, 1951.
Core et al., Science 322:1845, Dec. 19, 2008.
Danko et al., Molecular Cell 50:212, Apr. 25, 2013.
Dignam, et al., Nucleic Acids Research, 11, 1475-1489, 1983.
Egloff, et al., J. Virol. 80(17):8493-502, 2006.
Fahrer, et al., Nucleic Acids Res. 35(21):e143, 2007.
Frizzell et al., The Journal of Biological Chemistry 284: 33926, Dec. 4, 2009.
Hah, et al., Cell, 145, 622-634, 2011.
Hamké, et al., EMBO Reports, 9(11):1094-1100, 2008.
Hendriks, et al., Nature Structural & Molecular Biology, 21, 927-936, 2014.
Hornbeck, et al., Nucleic Acids Research, 40, D261-270, 2012.
Huang et al., Genome Biology 8:R183, 2007.
Huang, et al., Nucleic Acids Research 35:W169-175, 2007b.
Jiang, et al., Journal of the American Chemical Society 132, 9363-9372, 2010.
Jungmichel et al., Molecular Cell 52:272, Oct. 24, 2013.
Karras et al., EMBO J. 24(11):1911-20, 2005.
Kim et al., Cell 119:803, Dec. 17, 2004.
Kininis et al., Molecular and Cellular Biology 29:1123, March, 2009.
Krishnakumar et al., Science 319:819, Feb. 8, 2008.
Kumar and Colman, Archives of biochemistry and biophysics 308, 357-366, 1994.
Langmead et al., Genome Biology 10:R25, 2009.
Liang, et al., Nature Cell Biology 14, 45-466, 2012.
Luo, et al., BMC Genomics, 15:155, 2014.
Martin, EMBnet. Journal 17, 2011.
O'Neil et al., *Trends in Genetics: TIG* 29:290, May, 2013.
Petermann, et al., DNA Repair (Amst), 2(10): 1101-14, 2003.
Pleschke, et al., Biol Chem. 29; 275(52):40974-80, 2000.
Quinlan and Hall, Bioinformatics, 26:841-842, 2010.
Robinson et al., Bioinformatics 26:139, Jan. 1, 2010.
Robinson, Nature Biotechnology, 29:24-26, 2011.
Saldanha, Bioinformatics 20:3246, Nov. 22, 2004.
Schwartz and Gygi, Nature Biotechnology, 23:1391-1398, 2005
Shen et al., Nature 488:116, Aug. 2, 2012.
Sun et al., The Journal of Biological Chemistry 286:36248, Oct. 21, 2011.
Thorvaldsdottir, et al., Briefings in Bioinformatics, 14:178-192, 2013.
Walker, et al., Biochem Biophys Res Commun. 342(1):336-41, 2006.
Wessel and Flugge, Analytical Biochemistry 138:141-143, 1984.
Yu et al., *Nature Genetics* 36:1105, October, 2004.
Zang, et al., Bioinformatics, 25:1952-1958, 2009.
Zhang, et al., Nature Methods, 10:981-984, 2013.

What is claimed is:

1. A compound of the formula:

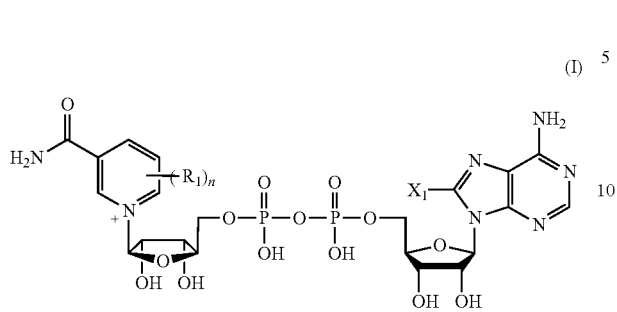

wherein:
- $X_1$ is -$A_1$-$Y_1$, wherein:
  - $A_1$ is —O—, or —S;
  - $Y_1$ is cycloalkyl$_{(C≤12)}$, alkynyl$_{(C≤12)}$, aryl$_{(C≤12)}$, aralkyl$_{(C≤12)}$, heteroaryl$_{(C≤12)}$, acyl$_{(C≤12)}$, alkoxy$_{(C≤12)}$, wherein any of these groups is optionally substituted; or
- $X_1$ is -$A_2$-$L_1$-$Y_2$, wherein:
  - $A_2$ is —O—, or —S;
  - $L_1$ is a linker which comprises a 1,2,3-triazole; and
  - $Y_2$ is a solid support, a biotin, a fluorophore, a protein, an enzyme, a DNA sequence, or an antibody;
- $R_1$ is amino, aminosulfonyl, carboxy, cyano, halo, hydroxy, hydroxysulfonyl, hydroxyamino, mercapto, nitro, or
- alkyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, wherein any of these groups is optionally substituted; and
- n is 0, 1, 2, 3, or 4;

or a salt, a reduced form, or tautomer thereof.

2. The compound of claim 1, wherein the compound is further defined as:

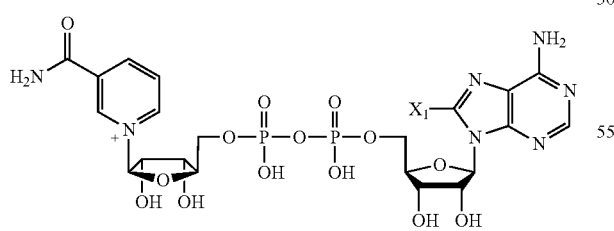

wherein: $X_1$ is as defined in claim 1 or a salt, a reduced form, or tautomer thereof.

3. The compound of claim 1, wherein the compound is further defined as:

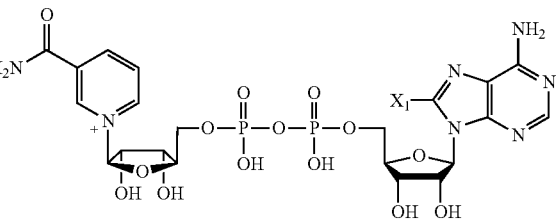

wherein:
- $X_1$ is -$A_1$-$Y_1$, wherein:
  - $A_1$ is —O—, or —S;
  - $Y_1$ is cycloalkyl$_{(C≤12)}$, alkynyl$_{(C≤12)}$, aryl$_{(C≤12)}$, aralkyl$_{(C≤12)}$, heteroaryl$_{(C≤12)}$, acyl$_{(C≤12)}$, alkoxy$_{(C≤12)}$, wherein any of these groups is optionally substituted;

or a salt, a reduced form, or tautomer thereof.

4. The compound according to claim 1, wherein $A_1$ is —S—.

5. The compound according to claim 1, wherein $Y_1$ is cycloalkyl$_{(C≤12)}$ or substituted cycloalkyl$_{(C≤12)}$.

6. The compound according to claim 1, wherein $Y_1$ is alkynyl$_{(C≤12)}$ or substituted alkynyl$_{(C≤12)}$.

7. The compound of claim 6, wherein $Y_1$ is 3-butyn-1-yl.

8. The compound according to claim 1, wherein $Y_1$ is aryl$_{(C≤12)}$ or substituted aryl$_{(C≤12)}$.

9. The compound according to claim 1, wherein $Y_1$ is alkoxy$_{(C≤12)}$ or substituted alkoxy$_{(C≤12)}$.

10. The compound according to claim 1, wherein n is 0.

11. The compound of claim 1, wherein the compound is further defined as:

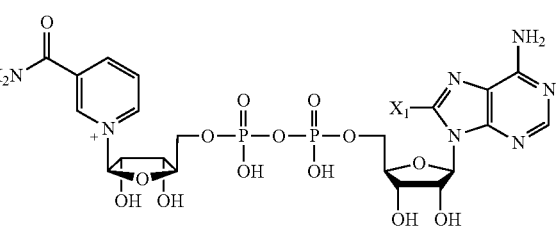

wherein:
- $X_1$ is -$A_2$-$L_1$-$Y_2$, wherein:
  - $A_2$ is —O—, or —S;
  - $L_1$ is a linker which comprises a 1,2,3-triazole; and
  - $Y_2$ is a solid support, a biotin molecule, a fluorophore, a protein, an enzyme, a DNA sequence, or an antibody;

or a salt, a reduced form, or tautomer thereof.

12. The compound according to claim 1, wherein $A_2$ is —S—.

13. The compound of claim 1, wherein $L_1$ is a linker which comprises the group:

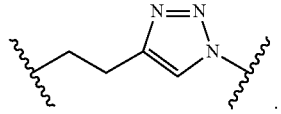 [SMILES: *CCc1cn(*)nn1]

14. The compound according to claim 1, wherein $Y_2$ is a protein.

15. The compound according to claim 1, wherein $Y_2$ is biotin.

16. The compound according to claim 1, wherein $Y_2$ is a fluorophore.

17. The compound according to claim 1, further defined as:

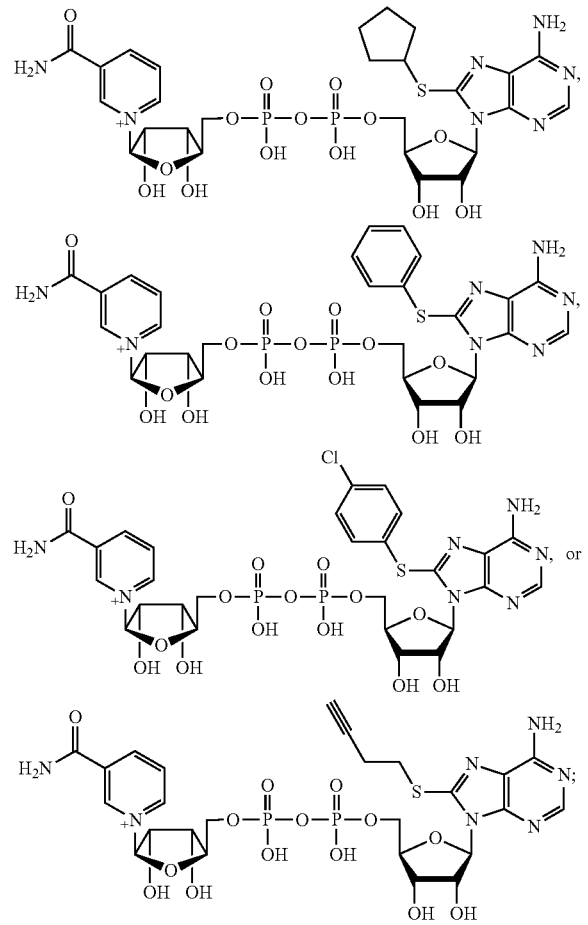

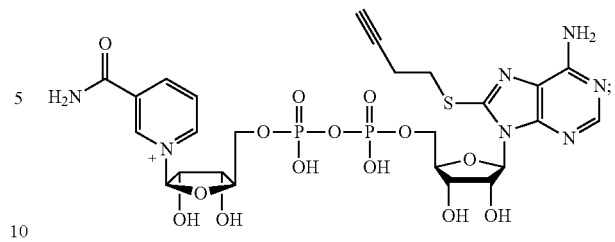

or a salt, a reduced form, or tautomer thereof.

18. The compound of claim 17, wherein the compound is further defined as:

or a salt, a reduced form, or tautomer thereof.

19. The compound according to claim 1, wherein the salt comprises a cation selected from the group consisting of a Group 1 metal cation, Group 2 metal cation, and a compound comprising a protonated ammonium, a protonated monoalkylammonium, a protonated dialkylammonium, a protonated trialkylammonium, or a tetraalkylammonium.

20. The compound of claim 19, wherein the cation is sodium, potassium, lithium, magnesium, calcium, ammonium, tetramethylammonium, choline, or a protonated amino acid.

21. A method of identifying a target protein wherein an amino acid on the target protein is ribosylated by a PARP protein comprising:
 (A) providing a PARP protein comprising a mutation in the NAD binding site;
 (B) incubating the PARP protein with a compound of formula (I) according to claim 1 and a cell or a cellular extract under conditions sufficient to ribosylate the target protein; and
 (C) identifying the target protein ribosylated in step (B).

22. A method of identifying an amino acid ribosylated on a target protein by a PARP protein comprising:
 (A) providing a PARP protein comprising a mutation in the NAD binding site;
 (B) incubating the PARP protein with a compound of formula (I) according to claim 1 and a cell or a cellular extract under conditions sufficient to ribosylate the target protein to form a ribosylated target protein;
 (C) immobilizing the ribosylated target protein by reacting with an immobilizing agent;
 (D) digesting the ribosylated target protein with a protease; and
 (E) analyzing a digest of the ribosylated target protein to identify the ribosylated amino acid.

* * * * *

UNITED STATES PATENT AND TRADEMARK OFFICE
CERTIFICATE OF CORRECTION

PATENT NO. : 9,926,340 B2  
APPLICATION NO. : 15/088561  
DATED : March 27, 2018  
INVENTOR(S) : W. Lee Kraus et al.

Page 1 of 1

It is certified that error appears in the above-identified patent and that said Letters Patent is hereby corrected as shown below:

In the Claims

Claim 1, Column 57, Line 23, delete "–S;" and insert -- –S–; -- therefor.

Claim 1, Column 57, Line 30, delete "–S;" and insert -- –S–; -- therefor.

Claim 3, Column 58, Line 15, delete "–S;" and insert -- –S–; -- therefor.

Claim 11, Column 58, Line 50, delete "–S;" and insert -- –S–; -- therefor.

Signed and Sealed this  
Tenth Day of July, 2018

Andrei Iancu  
*Director of the United States Patent and Trademark Office*